United States Patent
Adams, Jr. et al.

(10) Patent No.: US 7,939,325 B2
(45) Date of Patent: May 10, 2011

(54) METHOD AND APPARATUS FOR SUBSTANTIALLY ISOLATING PLANT TISSUES

(75) Inventors: Whitney R. Adams, Jr., Mystic, CT (US); Brandon Davis, North Stonington, CT (US); Lubomyr Kucher, Waterford, CT (US); Brian Martinell, Mt. Horeb, WI (US); Jyoti Rout, Wildwood, MO (US); Brenda Lowe, Mystic, CT (US)

(73) Assignee: Monsanto Technology LLC, St. Louis, MO (US)

( * ) Notice: Subject to any disclaimer, the term of this patent is extended or adjusted under 35 U.S.C. 154(b) by 137 days.

(21) Appl. No.: 12/201,890

(22) Filed: Aug. 29, 2008

(65) Prior Publication Data

US 2009/0142837 A1 Jun. 4, 2009

Related U.S. Application Data

(60) Provisional application No. 60/969,287, filed on Aug. 31, 2007.

(51) Int. Cl.
*C12N 15/00* (2006.01)
(52) U.S. Cl. ...................................................... 435/440
(58) Field of Classification Search .................. 435/441, 435/422, 420, 415, 431, 440, 410, 430.1; 800/320.1, 278, 287; 47/58.1, 58.1 R, 58.1 SE
See application file for complete search history.

(56) References Cited

U.S. PATENT DOCUMENTS

| 1,849,786 A | 3/1932 | Bloede et al. |
| 3,301,292 A | 1/1967 | O'Connor |
| 4,986,997 A | 1/1991 | Posner et al. ................. 426/622 |
| 5,952,230 A | 9/1999 | Kim et al. ..................... 435/415 |

(Continued)

FOREIGN PATENT DOCUMENTS

EP 0 356 987 3/1990

(Continued)

OTHER PUBLICATIONS

Garin et al., "Effect of sugars, amino acids, and culture technique on maturation of somatic embryos of pinus stobus on medium with two ellan gum concentrations," *Plant Cell Tissue and Organ Culture*, 62: 27-37, 2000.

(Continued)

*Primary Examiner* — Kent L Bell
(74) *Attorney, Agent, or Firm* — SNR Denton US LLP; Thomas P. McBride, Esq.

(57) ABSTRACT

The present invention provides methods and devices for the rapid isolation of monocot plant embryos suitable for transformation or tissue culture. The invention includes mechanical devices for substantially isolating plant embryos for use as transformable explants. Media suitable for isolating plant embryos and methods for their preparation are also provided.

8 Claims, 33 Drawing Sheets

U.S. PATENT DOCUMENTS

| | | | |
|---|---|---|---|
| 6,070,815 A | 6/2000 | Miyatake | 241/47 |
| 6,384,301 B1 | 5/2002 | Martinell et al. | 800/294 |
| 7,057,089 B2 | 6/2006 | Ranch et al. | 800/320.1 |
| 7,150,993 B2 | 12/2006 | Davis et al. | 800/278 |
| 7,402,734 B2 * | 7/2008 | Martinell et al. | 800/287 |
| 7,560,611 B2 | 7/2009 | Adams et al. | 800/278 |
| 7,658,033 B2 | 2/2010 | Martinell et al. | 47/58.1 SE |
| 7,682,829 B2 | 3/2010 | Cai et al. | 435/469 |
| 7,694,457 B2 | 4/2010 | Martinell et al. | 47/58.1 SE |
| 2002/0120961 A1 | 8/2002 | Ranch et al. | 800/320.1 |
| 2004/0244075 A1 | 12/2004 | Cai et al. | 435/469 |
| 2005/0005321 A1 | 1/2005 | Martinell et al. | 800/278 |
| 2005/0246786 A1 | 11/2005 | Adams et al. | 800/278 |
| 2005/0246802 A1 | 11/2005 | Attree et al. | 435/422 |
| 2006/0005273 A1 | 1/2006 | Rudrabhatla et al. | 800/278 |
| 2008/0124727 A1 | 5/2008 | Rout et al. | 800/278 |
| 2008/0179435 A1 | 7/2008 | Martinell et al. | 800/278 |
| 2008/0182330 A1 | 7/2008 | Martinell et al. | 435/420 |
| 2009/0029449 A1 | 1/2009 | Adams et al. | 435/285.1 |

FOREIGN PATENT DOCUMENTS

| | | |
|---|---|---|
| GB | 402848 | 12/1933 |
| GB | 861711 | 2/1961 |
| JP | 017107 | 1/2001 |
| JP | 292717 | 10/2001 |
| JP | 2002-119886 A | 4/2002 |
| WO | WO 2006/022958 | 3/2006 |

OTHER PUBLICATIONS

Green et al., "Plant regeneration from tissue cultures of maize," *Crop Sci.*, 15:417-421, 1975.

Kumlehn et al., "In vivo development of wheat (*Triticum aestivum* L.) from zygote to plant via ovule culture," *Plant Cell Reports*, 16:663-667, 1997.

Laurie et al., "A novel technique for the partial isolation of maize embryo sacs and subsequent regeneration of plants," In Vitro *Cell Dev Biol.—Plant*, 35:320-325, 1999.

* cited by examiner

5A

5B

A

B

C

A. Hinge for cover
B. Cover
C. Cover rest and splash guard
D. Powered drive wheel
E. Powered cob holder
F. Cob
G. Moveable jet
H. Spring loaded retainer
I. Collection trough
J. Embryo separator Mesh holder for seeds or fruits a.

b.

Slotted holder for seeds or fruits fluid jet

Sheet for holding seeds or fruits: outside or inside

Cylinder for holding seeds or fruits: outside or inside fluid jet

Cotton explant purity compared

METHOD AND APPARATUS FOR SUBSTANTIALLY ISOLATING PLANT TISSUES

This application claims the priority of U.S. Provisional Application Ser. No. 60/969,287 filed Aug. 31, 2007, the entire disclosure of which is incorporated herein by reference.

BACKGROUND OF THE INVENTION

1. Field of the Invention

The present invention relates generally to substantially isolating target plant tissues, such as embryos, which are suitable for genetic transformation or tissue culture.

2. Description of Related Art

The preparation of tissues for plant propagation, regeneration and transformation is time consuming and labor intensive, especially as it usually involves manual excision of transformable or culturable plant tissues. For example, in corn (*Zea mays*), individual immature embryos are typically removed manually to provide genetically-transformable explants. The manual excision of embryogenic tissues is laborious and risks ergonomic injury to the worker. Moreover, when larger amounts of transformable plant tissue are required for high-throughput transformation and plant production, more workers must be employed and trained to meet the increased demands. Additionally, there can be significant variability in the quality of plant tissues obtained, depending on the skill level, care, attentiveness, and fatigue of the individual workers.

The tissue variability and lack of amenability to automation in previous techniques for isolating transformable plant tissues is problematic, as poor quality tissues negatively impact subsequent tissue culture, genetic transformation, and plant propagation. Nonetheless, to produce even a single transgenic plant suitable for commercial development and use in agriculture, it may be necessary to produce tens of thousands of individual transformation events in a single species. Thus, there is a great need in the art for improved methods of preparing target plant tissues that are more efficient, reduce the overall ergonomic burden on workers, reduce the amount of labor needed to process the plant materials, and/or that yield plant tissues that are of higher and more consistent quality than manually produced tissues.

SUMMARY OF THE INVENTION

In one aspect, the invention provides a method for obtaining embryos suitable for tissue culture and/or genetic transformation, comprising at least partially excising an embryo from a plant seed in a liquid medium consisting essentially of water and/or an osmotic agent with an osmolality of about 0 mOsm/kg to about 600 mOsm/kg, wherein the embryo remains viable for tissue culture and/or genetic transformation following excision of the embryo from the plant seed. The osmotic agent may further be an inert osmotic agent. In a further embodiment, the method comprises at least partially excising a plurality of embryos from a population of plant seeds or ears in the liquid medium. The osmotic agent may be selected from the group consisting of mannitol, sorbitol, glucose, and sucrose, or other osmotic agents. In particular embodiments, the medium consists essentially of water and mannitol in a concentration of from about 0.05 M to about 0.5 M, or sucrose in a concentration of from about 0.05 M to about 0.5 M. The method may further comprise the step(s) of genetically transforming the embryo, and regenerating a transgenic plant from the transformed embryo.

In certain embodiments of the method, the step of genetically transforming the embryo comprises use of a co-culture medium comprising a bactericide. In particular embodiments the bactericide is carbenicillin. In yet other embodiments, the co-culture medium comprises about 0.5-1.5 mg/L of 2,4-D.

The embryo may be from a member of the Poaceae, such as maize, rice, wheat, or millet. In particular embodiments, the embryo is a maize embryo or a millet embryo. In other embodiments, the embryo may be a soybean embryo, a cotton embryo, or another dicot embryo.

In another embodiment, the method comprises preparing the liquid medium in a media preparation system comprising: (a) an inlet for water; (b) an inlet for the osmotic agent; and (c) a chamber for mixing the water and osmotic agent to produce the liquid medium, wherein the inlet for water and inlet for the osmotic agent are coupled to the chamber for mixing to allow delivery of the water and osmotic agent to the chamber for mixing. In certain embodiments, the inlet for water and/or the inlet for the osmotic agent are coupled to a chamber or chambers for holding the water and/or osmotic agent. The method may further comprise coupling the chamber for mixing to a fluid jet apparatus. In other embodiments, the method further comprises sterilizing the liquid medium with a sterilizer selected from the group consisting of a filter, a UV or gamma radiation source, and a sterilizing heat source. The sterilizer may sterilize the water and/or osmotic agent prior to entering the mixing chamber. Alternatively, the sterilizer sterilizes the liquid medium concurrently with and/or after entering the mixing chamber. In yet another embodiment, the method comprises sterilizing the liquid medium after the liquid medium leaves the mixing chamber.

The method may further comprise measuring the fill level of one or more of the chamber(s) for holding water, the chamber for holding the osmotic agent, or the chamber for mixing the water and the osmotic agent. In further embodiments, the method comprises controlling delivery of the water and the osmotic agent to the chamber for mixing the water and the osmotic agent. In particular embodiments, the method comprises controlling the delivery by electronically sensing the delivery of the water and/or the osmotic agent.

In another aspect, the method for preparing a plant embryo suitable for tissue culture and/or genetic transformation comprises: (a) placing plant seed tissue comprising plant embryos and/or seed coats in an aqueous environment; (b) contacting the tissue with an agent that selectively attaches to the embryos or seed coats; and (c) isolating at least a first embryo based on the selective attachment of the agent to the embryo or seed coat. In certain embodiments, the agent comprises gas bubbles. In particular embodiments, the gas bubbles have a largest average dimension of from about 100 microns to about 1 mm. In certain embodiments the gas bubbles may comprise a gas selected from the group consisting of air, oxygen, nitrogen, and a combination thereof. Further, in certain embodiments, step (c) comprises isolating the first embryo based on the buoyancy of the embryo.

The method may also comprise including in the aqueous environment a surfactant that reduces coalescence of bubbles with one another. In certain embodiments, the surfactant is selected from the group consisting of a polyether, PPG (poly (propylene glycol)), and PEG (poly(ethylene glycol)). In particular embodiments, the PPG has a molecular weight of about 340 to about 3500 daltons, and the PEG has a molecular weight of about 100 daltons to about 9000 daltons.

In yet other embodiments, the agent comprises a second liquid that is immiscible with the aqueous environment. The second liquid may be selected from the group consisting of vegetable oil such as canola oil, mineral oil, or other hydrophobic liquid compatible with survival and transformation of the embryos.

In certain embodiments, the plant seed tissue comprises embryos produced by at least partially excising an embryo from a plant seed in a liquid medium (aqueous environment) consisting essentially of water and/or an osmotic agent with an osmolality of about 0 mOsm/kg to about 600 mOsm/kg, wherein the embryo remains viable for tissue culture and/or genetic transformation following excising the embryo from the plant seed. In particular embodiments, the aqueous environment consists essentially of a medium comprising water and/or an osmotic agent with an osmolality of about 7 mOsm/kg to about 500 mOsm/kg. The method may comprise placing the plant seed tissue in the aqueous environment without first separating embryo from non-embryo tissue. In a particular embodiment, the plant seed tissue is maize plant seed tissue. In other embodiments, the plant seed tissue is soybean plant seed tissue or cotton plant seed tissue.

In another aspect, the invention provides an apparatus for preparing plant embryo tissue suitable for tissue culture and/or genetic transformation comprising (a) a container for holding plant seed tissue comprising a plurality of plant embryos and non-embryo tissue, such as plant seed coats, in an aqueous environment; and (b) at least a first nozzle for delivering to the aqueous environment an agent that selectively attaches to the embryos or seed coats, wherein the nozzle produces gas bubbles with an average diameter of from about 0.1 mm to about 1 mm. In certain embodiments, the invention provides an apparatus, wherein the container is filled with media and plant seed tissue comprising embryo and non-embryo tissue. In particular embodiments the apparatus further comprises a collector for separating embryo tissue based on the buoyancy of the embryos within the aqueous environment. In yet other embodiments, the gas bubbles may comprise a gas selected from the group consisting of air, oxygen, nitrogen, and a combination thereof.

In yet another aspect, the invention provides a method for preparation of plant embryos suitable for tissue culture and/or genetic transformation comprising (a) directing a first stream of liquid medium onto a corn kernel or other tissue comprising a plant embryo to extract endosperm from the kernel or tissue; and (b) directing a second stream of liquid medium onto the kernel or tissue to extract an embryo from the kernel or tissue. In certain embodiments, the liquid medium consists essentially of water or an osmotic agent with an osmolality of about 7 mOsm/kg to about 500 mOsm/kg. In a particular embodiment, the kernel may be comprised on an ear of corn. In certain embodiments the method may further comprise moving the ear of corn relative to the first and second stream to remove the endosperm and embryo from the kernel in succession. In certain embodiments, the first and/or second stream comprises a width less than the width of the corn kernel. In particular embodiments the first and/or second stream comprises a width of about 0.003" and height of about 1", and the first and/or second stream is produced at a pressure of from about 30 PSI to about 75 PSI.

In certain embodiments, the first and/or second stream may be directed from a nozzle that produces a laminar fluid flow stable at a distance of at least 2.5" from the nozzle. In yet other embodiments, the kernel may be positioned about 1¾-2" from the tip of the nozzle. In certain embodiments the first and/or second stream contacts each kernel in a row of kernels found on the ear with substantially the same force.

In another aspect, the invention provides an apparatus for obtaining corn or other plant embryos suitable for tissue culture and/or genetic transformation comprising (a) at least a first fluid jet for directing a medium onto a corn kernel or another tissue comprising a plant embryo; and (b) an apparatus for holding the kernel or other tissue in the path of the medium. The corn kernel may be comprised on an ear of corn. In certain embodiments, the apparatus for holding the kernel or other tissue comprises a sheet or a cylindrical sheet. In other embodiments the apparatus for holding the kernel or other tissue comprises a mesh or a plurality of slots; or a pressure cam or screw that applies force to the tissue being held. Seed or fruit tissue may be held onto the apparatus for holding the kernel or other tissue by a mechanical force, friction, centrifugal force, or a suction force. In particular embodiments the holder may comprise a pressure cam, auger, or screw. In certain embodiments, the apparatus for holding the kernel or other tissue is suspended in a gaseous phase, a liquid phase, or is partially suspended in gaseous and liquid phases. In other embodiments, the apparatus for holding the kernel or other tissue is fixed relative to a fluid force, or is movable relative to a fluid force.

Another aspect of the invention comprises a method for preparation of plant embryos suitable for tissue culture and/or genetic transformation, wherein the apparatus for holding the kernel or other tissue is centrifuged in a container to apply force to the kernel, or other tissue.

The apparatus may be further defined as comprising a first and a second fluid jet. Further, in certain embodiments the apparatus for holding the kernel comprises means for moving the ear of corn relative to the first and second fluid streams to control the angle of contact between the first and second fluid streams and the kernel. In particular embodiments the apparatus further comprises a detector to identify excised endosperm tissue and embryos.

In certain embodiments the apparatus further comprises at least a first separator to isolate embryos from non-embryo tissue. In particular embodiments, the separator separates embryos suitable for tissue culture from non-embryo tissue by a method selected from the group consisting of size exclusion, differential density and differential hydrophobicity. The apparatus may further be defined as comprising a sieve for separating embryo from non-embryo tissue based on size. In a particular embodiment the apparatus for holding the kernel comprises at least a first motor for moving the ear of corn relative to the fluid jet, or vice versa.

BRIEF DESCRIPTION OF THE DRAWINGS

FIG. 5 (top) depicts a cross-sectional view of one embodiment of such a device, showing how the nozzle, optional suction head, and corn ear may be positioned relative to each other. FIG. 5 (bottom) schematically depicts a corn ear positioned in the device. Legend: (A) base, (B) nozzle, C) shaft attached to base of ear, (D) suction head, (E) corn ear, and (F) aperture for guiding fluid flow.

DETAILED DESCRIPTION OF THE INVENTION

Figure 1:
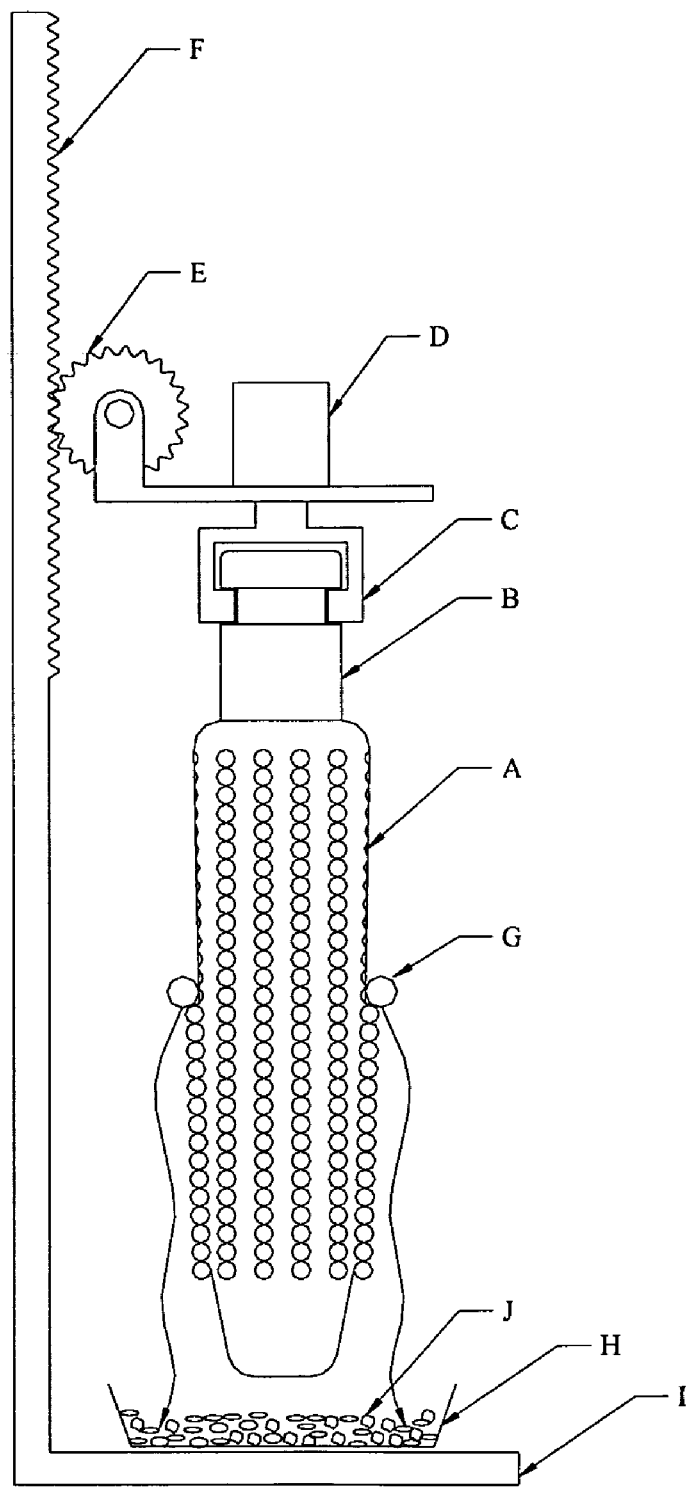
FIG. 1 depicts one embodiment of an apparatus provided by the invention that uses positive mechanical pressure for substantially isolating embryos, as described in Example 4.

Unless defined otherwise, all technical and scientific terms used herein have the same meaning as commonly understood by one of ordinary skill in the art to which this invention belongs, when taken in context of the present specification. Where there are inconsistencies between the text of the specification and the material incorporated by reference, the definitions and meanings provided in the present specification are intended. The nomenclature used herein and the manufacture or laboratory procedures described below are well known and commonly employed by those of skill in the art.

The phrases "substantially isolated" or "extracted" refer to the processing of a target tissue (e.g., an embryo or other tissue explant) that resides in or forms part of a larger tissue complex (e.g., a seed) such that the target tissue is physically separated from at least half of the larger complex. In some embodiments, a substantially isolated target tissue may be physically separated from at least about 20%, 30%, 40%, 50%, 60%, 70%, 85%, 90%, 95%, 97%, 98% r 99% of the larger complex, or any fraction thereof. In other embodiments, the target tissue is physically separated from more than about 80% to about 100%, about 90% to about 100%, or about 99% to about 100% of the larger complex, or any fraction in between. In some embodiments, the target tissue may be physically separated from about 100% of the larger complex.

While a substantially isolated target tissue is physically separated from some percentage of the larger complex, it does not necessarily have to be purified from that complex. In other words, the substantially isolated target tissue may remain in a batch with the larger tissue complex, so long as the target tissue is physically separated from the complex (as described above). In some embodiments, however, it may be desirable to remove some, or all, of the separated complex from the substantially isolated target tissue. All such embodiments are within the scope of the present invention.

The phrase "target plant tissue" refers to a portion of a plant tissue or seed that one seeks to substantially isolate. In the present invention, target plant tissue refers to any portions of a plant or plant seed that can be substantially isolated and used for genetic transformation or tissue culture. In some embodiments, the target plant tissue is an embryo, such as an immature embryo from a monocot such as corn. In other embodiments, the target plant tissue is from a dicotyledonous plant such as soybean (*Glycine* sp. including *Glycine max*) or cotton (*Gossypium* sp. including *G. hirsutum*).

The phrase "suitable for genetic transformation" and "suitable for tissue culture" refer to plant tissues that are competent for transformation or growth in under suitable plant culture conditions, respectively. One of skill in the art can readily determine if a particular target tissue is suitable for genetic transformation or tissue culture by using routine experimentation. For example, a sample from a batch of substantially isolated target tissues may be cultured on suitable plant media (also known to those of skill in the art) to determine if the tissues are capable of growth and regeneration. Similarly, samples of substantially isolated target tissues can be subject to transformation and screened for the presence of a heterologous nucleic acid molecule. Such techniques are routine and can rapidly identify which tissues are competent for transformation or tissue culture and which, if any, are not.

Substantially Isolating Target Plant Tissues

The present invention provides methods of substantially isolating target plant tissues suitable for genetic transformation and/or tissue culture. In some embodiments, the target plant tissue is an embryo. In one embodiment, the embryos are monocot embryos, such as from maize. In some embodiments, the substantially isolated target tissue may be isolated in whole or in part. For example, a batch of substantially isolated immature embryos may include intact embryos, partial embryos, or mixtures thereof. Preferably, the intact and/or partial tissues are suitable for genetic transformation, tissue propagation, plant regeneration and other tissue culture applications.

As tissues are being isolated using, for example, by streams of a selected media, a collection receptacle may be provided. In some embodiments, it is useful to provide a covering for such collection receptacles, in order to improve the efficiency of the apparatus, reduce mess, prevent undesirable splashing from the jet stream, and/or limit any escape of extracted tissues during harvesting. Any suitable receptacle or receptacle covering may be employed. Examples are given elsewhere in this application and are also known to those of skill in the art.

Suitable coverings for the receptacle may include those made of metals, wood, glass, meshes, fabrics, plastics, rubbers, latex, acrylics, and functionally equivalent materials. In some embodiments, the material is flexible so as to allow penetration and removal of an ear of corn while maintaining a substantially water tight seal around the ear during the extraction process. The material may be provided with a suitable opening to allow entry and removal of an ear of corn. In some embodiments, the material is solid and contains a flexible hole for receiving and holding the ear during extraction. In other embodiments, the material is flexible. Such flexible materials may be stretched over the receptacle to form a liquid tight fit, but allows for insertion of an ear either by penetrating the material or by providing an opening to receive the ear of corn. In still other embodiments, the material is a mesh or screen that has a flexible opening.

The coverings may be removable or semi-permanently attached. In some embodiments, the materials are held by an elastic band or equivalent securing means. In other embodiments, the covering is held in place by weights, friction collars, hooks, snaps, or other functionally equivalent securing means.

The covering may be made of a flexible material and have varying thickness. These factors may be varied in order to achieve the desired effects for insertion and extraction of ears of corn. The following table (Table 1) illustrates some hardness and thickness parameters for silicone coverings. The invention, however, is in no way limited to these few choices.

TABLE 1

Hardness and thickness parameters of coverings.

| Durometer hardness | Membrane thickness (in.) |
|---|---|
| 10 A | 1/32 |
| 10 A | 1/16 |
| 20 A | 1/32 |
| 20 A | 1/16 |
| 40 A | 1/32 |
| 40 A | 1/16 |

Figure 8:
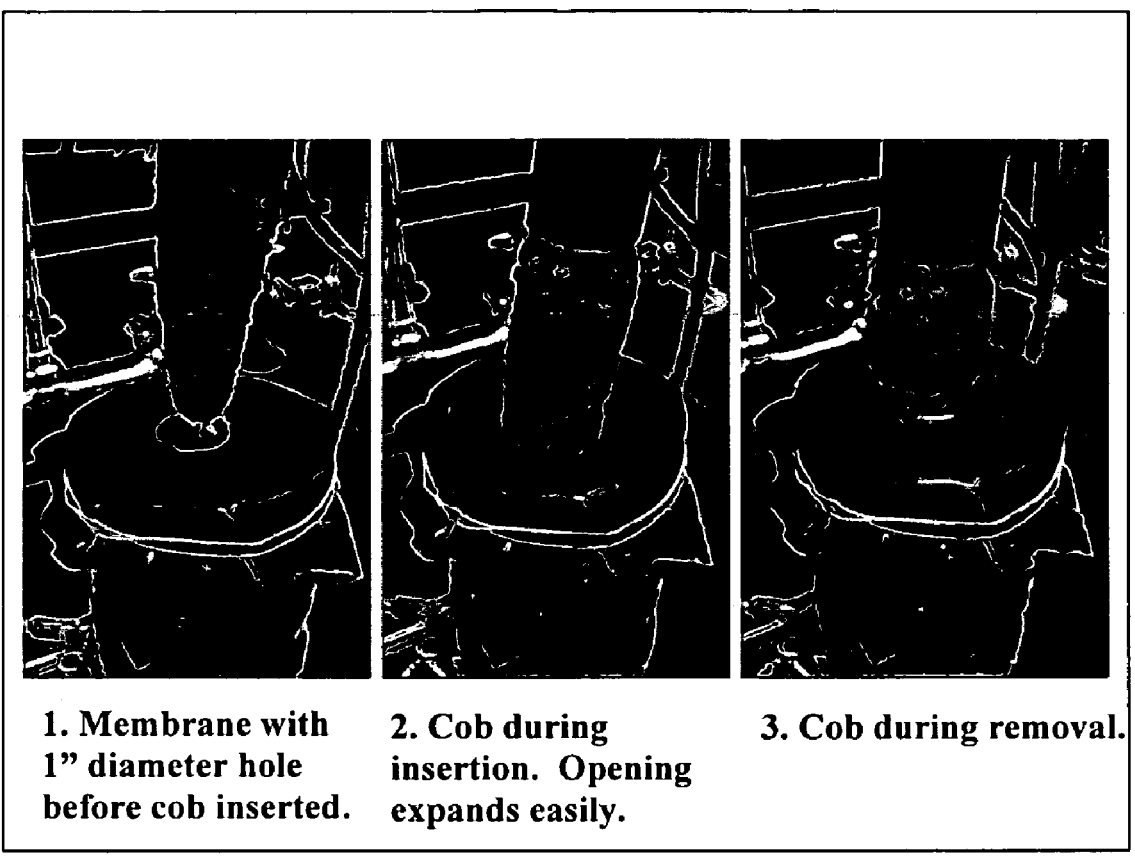
FIG. 8 depicts an embodiment of the invention in which the top of a cylinder is wholly, partially or substantially covered with a membrane or a sheet of soft material that is slightly smaller than the diameter of the corn ear and the handle to which the corn ear is attached. Specifically, a silicone rubber membrane splash guard (1/32" thick) from McMaster-Carr (McMaster-Carr, Atlanta, Ga.; e.g. cat. #9010K11) is shown. A 1" diameter hole was made in the membrane. The corn ear was able to move both down through the opening and also back up through it.

In one embodiment, the collection receptacle is covered with a membrane or sheet of soft material that is slightly smaller than the diameter of the corn ear and handle to which it is attached. In an alternative embodiment, small incisions are made in the membrane to provide more flexibility. The membrane may be attached to the cylinder by a means such as an elastic band or a friction fit collar, or the like. FIG. 8 illustrates an embodiment of the covering and attachment means described above.

In some embodiments, the material is autoclavable. Autoclavable materials are well known to those of skill in the art. For example a soft material such as a soft silicone rubber sheet may be used. One of skill in the art is aware of the possible materials and physical arrangements that will permit extraction while providing a collection vessel that reduces escape of extracted tissue and prevents undesirable splashing.

Suitable procedures for plant tissue culture and regeneration are well known in the art. See, for example, U.S. Pat. No. 5,550,318 to Adams et al., U.S. Pat. No. 5,780,708 to Lundquist et al., United States Patent Application Publication Number 2004/0210958 to Duncan et al., United States Patent Application Publication Number 2004/0016030 to Lowe et al., and United States Patent Application Publication Number 2004/0244075 to Cai et al., which disclose transformation methods useful with corn, and United States Patent Application Publication Number 2003/0024014 to Cheng et al., which disclose transformation methods useful with wheat, all of which are incorporated by reference in their entirety herein. The tissue culture applications can include at least one process selected from transformation, callus formation, formation of differentiated plant tissue, formation of at least one mature plant, formation of at least one fertile mature plant, and combinations of these processes. The plants regenerated from the extracted immature embryos may be regenerated, for example, through differentiation of de-differentiated tissue (calli). Regenerated plants can be grown to maturity to provide mature plants, including fertile mature plants. The extracted immature embryos and extracted non-embryo tissues may also be used for other purposes, such as, but not limited to, genetic or biochemical analysis.

The methods and apparatuses of the present invention can be applied to any monocot plants of interest. Preferred monocots include, but are not limited to, members of the family Poaceae, including grain crops such as corn (maize), wheat, barley, oats, rye, sorghum, millet, and rice. Particularly preferred monocots include Zea species, including corn (*Zea mays*), and millets (e.g. *Pennisetum glaucum, Pennisetum* sp., *Setaria* sp., *Panicum* sp.) which have multiple kernels (seeds) typically held in rows on an ear.

In general, the monocot seeds from which the target tissues are substantially isolated are provided in any suitable manner. For example, seeds may be attached to the ear or head on which the seeds grow; in some embodiments the monocot seeds may be removed from the ear or head prior to substantially purifying the target tissue.

In some embodiments, an opening in the pericarp or seed coat of the monocot seeds is provided. This may be accomplished by any suitable technique, such as, but not limited to, making a hole, puncture, or incision with a needle, awl, blade, or other suitable implement. In some applications of the method, no pericarp tissue need be removed; in other embodiments, the opening of the pericarp may include removal of at least part of the pericarp and possibly of some non-embryo tissue (e.g., endosperm). Preferably, the opening is sufficient to substantially separate the embryo from the seed. In some embodiments it may be necessary only to weaken the pericarp sufficiently (for example, by abrasion, or by other physical, chemical, or enzymatic treatment) so that application of force to the seed results to substantial isolation of the target tissue, such as the embryo.

In such a method force is generally applied to seeds sufficient to substantially isolate the target tissue, such as an immature embryo, wherein the substantially isolated target tissue is suitable for genetic transformation and tissue culture. Force may be applied to multiple seeds consecutively or simultaneously. The applied force can be continuous or non-continuous (for example, pulsed or wave-like force), and is generally mechanically applied, that is, through use of a device or machine rather by human hand. The amount of force applied is preferably sufficient to overcome the adhesion of the target (e.g., embryo) and non-target (e.g., non-embryo tissue such as endosperm) from each other, thus allowing separation of the target and non-target tissues. Any suitable force or forces may be employed for removal of the target tissue from its seed, and multiple forces may be used in combination, sequentially or simultaneously. Suitable forces include, but are not limited to, fluid jet positive pressure, liquid jet positive pressure, mechanical positive pressure, negative pressure, centrifugal force, linear acceleration, linear deceleration, fluid shear, fluid turbulent flow, suction, and fluid laminar flow. Fluid forces can be exerted by any fluid, e.g. gases or liquids, or combinations of both.

Figure 10:
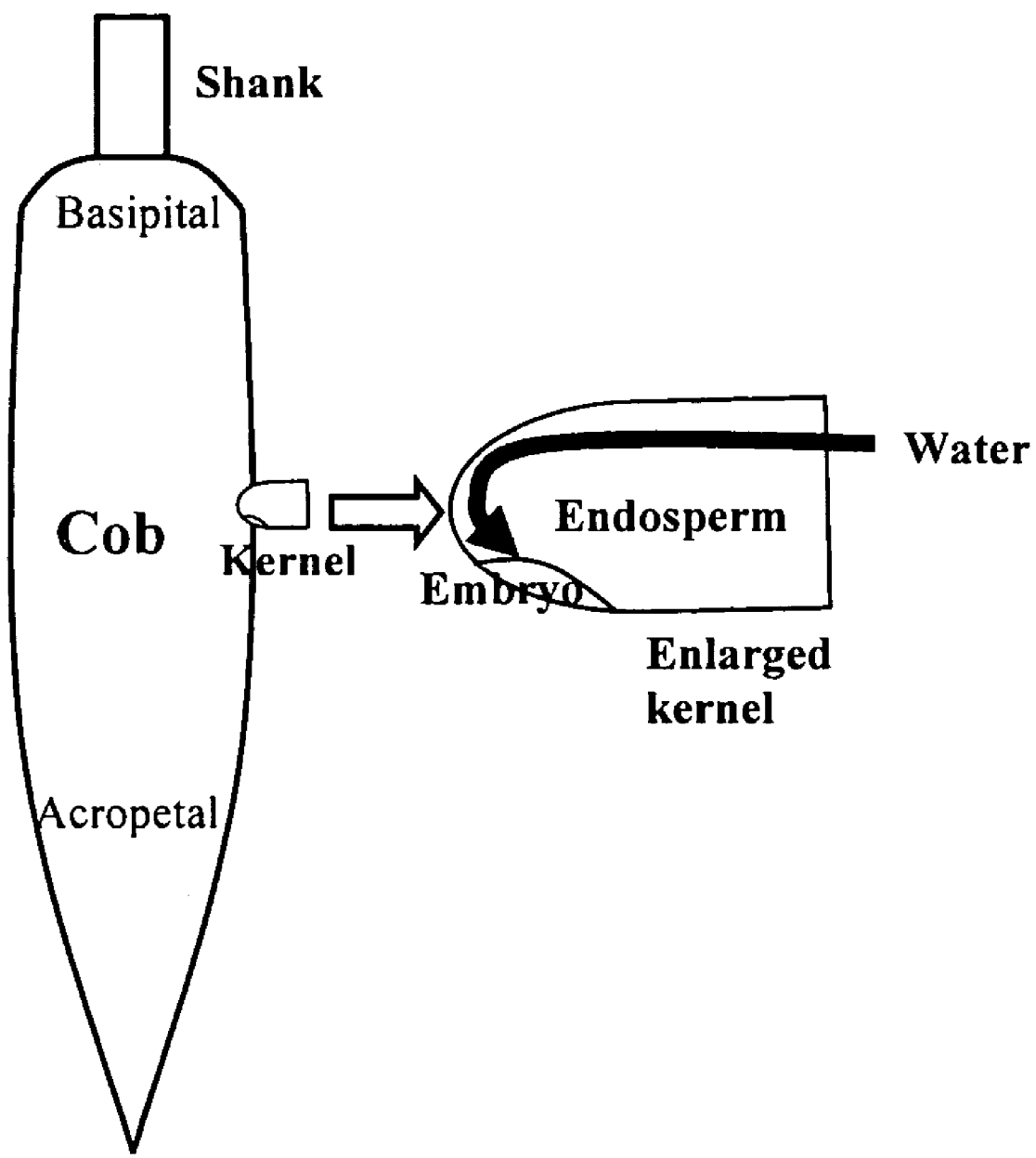
FIG. 10 depicts a corn cob showing the location of the embryo within an individual kernel. Also shown is one embodiment of the invention in which a liquid jet is directed to the basipetal side of the kernel, opposite the acropetal side where the embryo is located.

Since a corn embryo is located on the acropetal side of a kernel, it is possible to direct a liquid jet to the basipetal side of the kernel, if desired, to successfully eject the embryo (See, e.g., FIG. 10). In such an arrangement, the full force of the jet is generally not directly impacting the embryo. Rather, the substantial amount of the force is only indirectly applied to the embryo itself. Thus, stronger forces may be applied in the apparatus to accelerate the removal of embryos without substantially increasing the damage to the embryos being removed.

Higher impact forces can be provided by forcing higher quantities of liquid through the apparatus of the present invention. In some embodiments, however, higher impact forces can be generated without using more liquid. For example, in some embodiments, the size of the jet opening is reduced so that the same volume of liquid can be used at a higher velocity. As the energy of a moving object is proportional to the square of the velocity, a jet with the same volume can have much greater energy. A simple equation for kinetic energy of a moving object is equal to $(\frac{1}{2})(m)(v^2)$. The calculation of the actual impact energy of a liquid jet would also take into account other factors known to those of skill in such art. Additionally, some embodiments may use a combination of increased fluid and changes in the size of the jet openings to achieve the desired force or energy.

Nozzles with gpm ratings of about 0.01 to about 0.25, for example, may be used in the present invention, or about 0.01 to about 0.2, or about 0.01 to about 0.1, or about 0.01 to about 0.09, 0.08, 0.07, 0.06, 0.05, 0.04, 0.03, 0.02, or 0.015, or any whole number or fraction in between these amounts. In some embodiments, using nozzles with low gpm ratings, like 0.033 or 0.021 gpm may be used. When such nozzles are used with higher pressure but directed at the opposite side of the kernel from the embryo, accelerated embryo harvesting may be achieved while avoiding injury to the embryo.

In some embodiments, multiple jets are provided in an apparatus of the present invention. Such an apparatus is useful to equalize the force exerted by the fluid jets while decreasing the time needed to harvest the embryos from an ear of corn.

Figure 9:
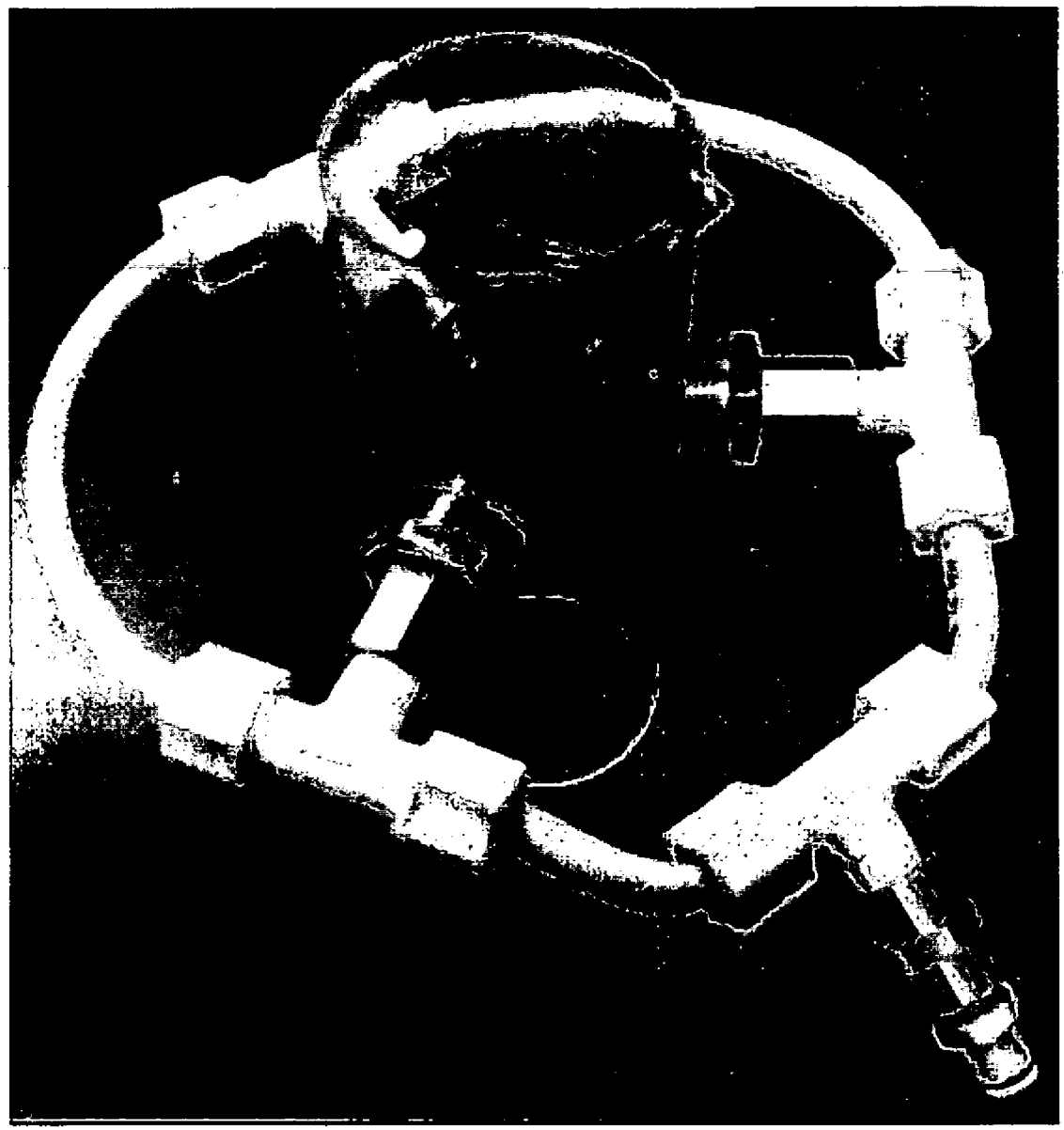
FIG. 9 depicts a 1 liter polymethylpentene graduated cylinder with the bottom cut off. Three fluid jets are threaded into holes cut in the wall of the cylinder. The entire apparatus can be autoclaved prior to use. For operation, the top of the cylinder can be fitted with a splash guard and the corn ear lowered into the cylinder so that the fluid jets dislodge the contents of each kernel. The dislodged material then falls out the bottom of the cylinder for further processing.

In some embodiments, the apparatus may have 2, 3, 4, 6, 8, 10 or more jet openings/nozzles as desired for conveying fluid force. In one embodiment, there are three openings. Such a device is depicted in FIG. 9. In some embodiments, the openings are provided as narrow-angle flat stream jets, oriented horizontally. However, other embodiments of the jet openings are provided elsewhere throughout this application. The stainless steel spray nozzle components connecting directly into the polymethylpentene graduated cylinder depicted in FIG. 9 are shown in Table 2:

TABLE 2

Spray nozzle components.

| Component description | Spraying Systems Cat. No. | Comments |
| --- | --- | --- |
| Wall mount adapter | 4865 SS | Threads into cylinder wall |
| Spray tip, solid stream | TP000067-SS | 0° spray angle, 0.067 gal/min (~253 ml/min) |
| Screen strainer (200 mesh) | 6051-SS-200 | Removes debris that can clog spray tip |
| Female body | CP1321-SS | Provides connection to ¼" male NPT pipe thread |

The remaining components are mostly tubing and fittings with a male quick disconnect fitting at the fluid source to the right of the photo (FIG. 9).

A method and apparatus of the invention can further provide for separating substantially isolated target tissue, such as immature embryos, from associated non-embryo tissue such as endosperm, glumes, and seed coat or pericarp tissues. Separation may be accomplished by one or more suitable techniques, including, but not limited to, separation by size exclusion (for example, by filtration in one or more filtering steps), separation based on hydrophobicity, hydrophilicity, or other forces, and separation by mass or density differentials (for example, separation by centrifugation, settling, and decanting). The separation step or steps can be optional, for example, where no additional isolation of intact or partial embryos is necessary for their use in tissue culture.

The invention is particularly suitable to applications where a large number of target tissues must be provided, for example, in high-throughput processes or screening, or in batch processing for genetic transformation or tissue culture. Automation of the method is possible, for example, by employing robotic or mechanical handling of the corn ears or seeds, opening of the pericarp, application of force to the seed, or the optional separation steps. Such automation may use optical or mechanical sensors to aid in positioning the corn ears or seeds relative to the applied force or forces, or in the separation steps. In one embodiment, the method provides substantially isolated embryos at a rate of between about 250 to 50,000 or more embryos per day, or between about 500 to about 100,000, or about 250 to about 50,000, or about 250 to about 20,000, or about 250 to about 10,000, or about 250 to about 5000, or about 250 to about 3000, or about 250 to about 1000 embryos per day; or between about 1,000 to about 50,000 embryos per day, and the like, including any fraction or whole number in between any of the aforementioned ranges. As noted above, the present invention overcomes the significant output limitations of manual excision of embryos.

Apparatus for Substantially Isolating Target Plant Tissues

The present invention also provides an apparatus for substantially isolating target tissues, such as corn embryos, that are suitable for genetic transformation or tissue culture. In one embodiment for separating corn embryos, such an apparatus may comprise at least one aperture for guiding a fluid stream, wherein the fluid stream contacts kernels on the corn ear and substantially isolates embryos from the kernels. Generally, it is preferred that the fluid stream contact as many of the kernels in a given period of time as is convenient, so as to more rapidly isolate embryos. The aperture can include a single aperture or multiple apertures, for example, single or multiple nozzles, which can include nozzles which produce flat, round, oval, fan-shaped or other patterned jets of fluid, and adjustable, moving, or stationary nozzles, and can generate a fluid flow of any suitable type and medium. Fluids may be gases, such as air, nitrogen, or gas mixtures, liquids, such as water, physiological saline, or various culture media, media as described below, or combinations. Suitable fluid flows include, but are not limited to, fluid jets, such as single or multiple columnar jets; flat, cone-shaped, or fan-shaped jets or sprays; and sheet-like jets, laminar fluid flow, and turbulent fluid flow. Suitable fluid flows can result in a variety of forces to remove the embryo from its kernel, including positive pressure or negative pressure or both; such forces can be uniform or non-uniform, continuous or non-continuous (such as a pulsed or wave-like force), or in any combination thereof.

An apparatus of the invention may further include a means for moving the target tissue being substantially purified and the fluid stream, relative to each other. For example, either the ear of corn containing seeds or the fluid stream, or both, may be moved. Various embodiments of the apparatus can be used with single or multiple, intact or partial ears of corn. For example, the corn ear or ears can be secured to a holder or grasper, which is moved relative to the fluid stream. In other embodiments, however, the corn ear or ears need not be individually secured to a holder but can be freely movable so as to allow multiple kernels to be contacted by the force used to remove the embryos from the kernels. The means for moving at least one corn ear relative to the fluid stream can rotate the corn ear and the aperture relative to each other, or can move the fluid stream along the longitudinal axis of the corn ear, or can provide any suitable three-dimensional movement of the corn ear and the aperture relative to each other, such as a combination of rotation and longitudinal motion.

The invention further provides a separator for separating target tissues from non-target tissues. For example, embryos may be separated from non-embryo tissues, wherein the separated embryos comprise at least some corn embryos suitable for genetic transformation or tissue culture. Separators can work by a mechanism including, but not limited to, separation by size exclusion (for example, using a mesh, screen, perforated surface, or other device capable of excluding objects of a certain size), separation based on hydrophobicity or other attractive forces (for example, using a material, solid or fluid, that can attract or repel the embryos), and separation by mass or density differentials (for example, using a centrifuge, or using solutions for differential settling). In certain embodiments, the separator can be optional, for example, where no additional isolation of intact or partial embryos is necessary for their use in genetic transformation or tissue culture.

The substantially isolated immature embryos include at least some embryos, such as immature intact or partial embryos, suitable for tissue culture applications, transformation, callus formation, direct embryogenesis, formation of differentiated plant tissue, formation of at least one mature plant, formation of at least one fertile mature plant, and combinations of these processes, as described above. The substantially isolated immature embryos and non-embryo tissues may also be used for other purposes, such as, but not limited to, genetic or biochemical analysis.

The present invention further provides an apparatus for substantially isolating in a mechanical process multiple corn embryos suitable for genetic transformation or tissue culture from at least one immature corn ear. In one embodiment the device comprises at least one component selected from (a) at least one solid surface for applying mechanical positive pressure to the exterior of kernels on an immature corn ear; (b) an aperture for guiding a fluid flow, wherein the fluid flow contacts kernels on the corn ear; and (c) an aperture for applying negative fluid pressure that contacts kernels on the ear; wherein the component applies force sufficient to substantially isolate embryos from the kernels suitable for genetic transformation or tissue culture. The forces may be applied to multiple seeds consecutively or simultaneously, in a continuous or non-continuous manner, and are generally applied mechanically and not manually. Multiple forces may be used in combination, sequentially, or simultaneously. Suitable forces include, but are not limited to, fluid jet positive pressure, liquid jet positive pressure, mechanical positive pressure, negative pressure, centrifugal force, linear acceleration, linear deceleration, fluid shear, fluid turbulent flow, and fluid laminar flow. Fluid forces can be exerted by any fluid, gases or liquids or combinations of both.

Combination apparatuses of the invention can optionally include a means for moving the at least one corn ear relative to the source or sources of force for isolating embryos or parts thereof. The ear or ears may be moved relative to the source of force so that the force or forces contact as many of the kernels in a given period of time as is convenient, so as to more rapidly isolate embryos.

Combination apparatuses of the invention can further include at least one means for further separation of the substantially isolated immature embryos suitable for genetic transformation or tissue culture. Separators may function by a mechanism, including, but not limited to, separation by size exclusion, separation based on attractive forces, and separation by mass or density differentials.

Liquid Media for Excising Corn or Other Plant Embryos

The present invention provides in one embodiment media and methods for substantially isolating target plant tissues suitable for genetic transformation or tissue culture. For example, a fluid jet apparatus utilizes liquid for excising embryos, requiring substantial quantities of liquid for excision. Thus, for instance, about 20 L of a liquid medium may be needed for excising embryos from one ear of corn. The medium is therefore preferably easily prepared (consisting essentially of one or two ingredients), sterilizable, for instance through an in-line filtration unit, and can flow through a fluid jet apparatus operating at a pressure of about 30-75 psi, for instance about 40-60 psi. Further, it preferably does not require pH adjustment prior to use. To save resources and expense, it is also, preferably, reusable.

Culture media such as Lynx #1013 inoculation medium and Lynx #1902 (half-strength Lynx #1013) have been successfully used in an automated method and apparatus for excising corn embryos for use in tissue culture. However, these media have multiple ingredients, and require pH adjustment prior to use. Thus, the current inventors have developed media that can be used to optimize efficiency of an automated embryo excision method for tissue culture. Surprisingly, the inventors found in particular that a media consisting essentially of water and/or an osmotic agent with an osmolality of about 0 mOsm/kg to about 600 mOsm/kg to be useful.

In certain embodiments, an osmolality of about 0 mOsm/kg to about 600 mOsm/kg for the osmotic agent is preferred, including about 7 mOsm/kg to about 500 mOsm/kg, about 13 mOsm/kg to about 300 mOsm/kg, about 25 mOsm/kg to about 300 mOsm/kg, about 50 mOsm/kg to about 300 mOsm/kg, about 13 mOsm/kg to about 200 mOsm/kg, about 13 mOsm/kg to about 100 mOsm/kg, or about 100 mOsm/kg to about 300 mOsm/kg. In specific embodiments, a media provided consists essentially of sterile distilled water, dilute calcium chloride (e.g. about 10 ppm), 0.05% MES, pH 5.4-5.8, about 5% sucrose+/−MS salts, or about 0.05-0.5 M mannitol, including 0.1-0.2 M mannitol solutions. Although the transformation frequency (TF) of plant embryos excised by use of some such liquid media may be somewhat reduced from that found when using, for instance, the Lynx #1013 Inoculation Medium, the significant time and cost efficiencies arising from use of simpler media can outweigh any reduction in TF by allowing production of more explants using the same amount of resources.

In specific embodiments of the invention, an excision medium comprises as an osmotic agent mannitol and/sucrose, such as media consisting essentially of 0.05-0.5M mannitol. Such media was found capable of producing viable explants. In particular embodiments, an excision medium consists essentially of about 0.1-0.2 M mannitol. The osmolality of a 0.2 M solution of mannitol in water is, for instance, about 225 mOsm/kg. In other embodiments, sterile distilled water, as well as 5% sucrose (w/v) were also found to be simple, yet effective, media for use with the invention.

Media Preparation System

A Media Preparation System (MPS) for use with a fluid jet apparatus is another embodiment of this invention. The MPS, for instance, may be used to supply an excision medium described above. The MPS may consist of a housing (MPSH) and a mixing chamber (MC). The MPS may be made from a suitable material, such as aluminum (e.g. 7075 aircraft grade aluminum) or steel. The mixing chamber generally comprises a tank with an upper and a lower end, and may comprise a flange and a cover plate. The cover plate was generally provided with one or more o-ring(s) or other sealing means which seal the mixing chamber. The cover plate comprises openings for inserting and removing liquid and other media ingredients. Liquid and other media ingredients may be added via one or more inlets, comprised in the mixing chamber, which may communicate with a chamber and/or supply line that holds and/or delivers a supply of the ingredients. The cover plate may also comprise an electronic sensor for sensing a specified volume of medium that is being prepared. The mixing chamber may be oriented on a supporting plate and held in a working position by holding means, such as mounting pins and positioning brackets. The supporting plate may be slidably connected to the MPSH. In certain embodiments, the mixing chamber is connectable to a fluid jet apparatus, for instance via steel or polycarbonate tubing.

A mixer assembly may be attached to the cover plate or other part of the mixing chamber. The assembly may comprise an impeller and shaft mounted on a means for suspension such as a high temperature ball bearing. The mixer may be autoclaved prior to use. The MPS may further comprise a Programmable Logic Controller (PLC) in communication with sensors to monitor ingress of components, media preparation, and subsequent removal of media, for instance via a fluid outflow tube to the fluid jet apparatus. One or more fluid inflow and outflow tubes may comprise an inline filtration unit to sterilize the prepared media.

Apparatus for Phased Excision of Embryos

Methods and apparatuses for preparing multiple embryos suitable for tissue culture are embodiments of the invention, wherein the methods comprise use of at least two fluid streams for substantially extracting an embryo and endosperm from a seed kernel, and the apparatuses comprise at least one aperture for guiding a first fluid stream and a second fluid stream, for substantially extracting an embryo from a seed kernel. The apparatus may further comprise means for moving at least one seed ear relative to the first and second fluid streams. In certain embodiments, the seed ear or seed kernel is a corn ear or corn kernel.

The fluid streams may be gas streams or liquid streams. In certain embodiments, the fluid streams comprise liquid, and in particular embodiments the liquid consists essentially of distilled water, about 5% sucrose, or about 0.05 M-0.5 M mannitol, for instance about 0.1-0.2 M mannitol. The fluid stream may exert a force for substantially extracting an embryo, comprising one or more forces selected from the group consisting of fluid jet positive pressure, liquid jet positive pressure, mechanical positive pressure, negative pressure, centrifugal force, linear acceleration, linear deceleration, fluid shear, fluid turbulent flow, and fluid laminar flow. The fluid stream may be continuous or pulsed. In particular embodiments the fluid stream is sterile.

An apparatus of the invention may further comprise a means for detecting excised endosperm and embryo tissue, and a means for channeling endosperms or embryos for automation. The means for detecting and the means for channeling may be linked, for instance electronically, to assist in automation. The apparatus may also comprise at least one separator for separating embryos from non-embryo tissue, wherein the separated embryos are embryos suitable for tissue culture. The separator may separate embryos from non-embryo tissues by differential hydrophobicity, by size-exclusion, or by density differential. The embryo tissue may be cultured, transformed, and/or regenerated to yield at least one fertile plant. In particular embodiments, the embryo is a corn embryo, and the plant is a corn plant.

Separation of Embryos by Flotation

The invention further provides an apparatus and methods for separation of embryos based on differential affinity of a selected agent relative to non-embryo seed tissue. In certain embodiments, embryos, such as corn embryos produced by a fluid jet excision process, are contacted by, and attach to, bubbles via hydrophobic interactions. In other embodiments, seed coats are contacted by, and attach to, bubbles. The bubbles may comprise one or more gases selected from the group consisting of an inorganic gas such as argon, air, $O_2$, $N_2$; and a covalent organic gas such as methane, ethane, or propane, that do not seriously affect the viability and transformability of the excised embryos.

Bubble size was found to play an important role in the efficiency of the separation process. In practice, (gas) bubbles displaying a range of sizes may be generated. However, any bubble size that is suitable for attaching to the embryos or seed coats and raising them to the surface of the fluid is within the scope of this invention.

The size distribution of bubbles may vary with a number of factors such as:

Frit uniformity: The openings between particles composing a frit may be variable, allowing various size bubbles to form.

Gas flow rate: The flow rate of gas through the bubble-generating frit also affects bubble size—e.g. fast gas flow results in larger bubbles.

Surfactants and their concentrations: Media additives such as mannitol and PEG as well as proteins and other substances with surfactant properties released from the disrupted corn kernels may affect bubble size.

Bubble merging: As bubbles rise toward the top of the tank some of them merge with other bubbles.

Hydrostatic pressure: Bubbles near the bottom of a flotation tank will on average be slightly smaller because of the higher pressure at the bottom of the tank, although this effect would be minor in view of the size of the flotation tank.

Further, it is not necessary for a single bubble to carry a single embryo or seed coat all the way to the surface. Instead, an embryo or seed coat may be only partially carried to the surface by one bubble only to be carried further by sequential attachment of other bubbles. Also, an embryo or seed coat may not reach the surface and become embedded in the froth the first time around, but may circulate a number of times before arriving at the interface of the air and liquid phases (e.g. the "froth").

Large bubbles, for example, about 1 mm in diameter (i.e. if spherical; or largest dimension if non-spherical), or greater, do not achieve good separation for several reasons. For instance, such bubbles move fast enough that they hydrodynamically push embryos as well as debris out of their way. Thus such large bubbles tend to not adequately contact the embryos. Such bubbles also do not have sufficient contact time with the embryos or seed coats to allow efficient bubble attachment. Finally, such bubbles generate a high enough shear force while rising to the fluid surface that any embryos that are adhering to the bubbles tend to be detached before reaching the surface.

Small bubbles, e.g., bubbles around 100 micron diameter, or less, attach to debris as well as embryos. This is because the bubbles move slowly enough through the fluid that they do not push smaller material (e.g. endosperm fragments) out of the way. Thus, such bubbles contact with and attach to both embryos as well as other smaller debris. Finally, such bubbles do not generate enough shear force to efficiently dislodge attached debris.

Mid-sized bubbles (between 100 µm and 1 mm in size) were comparatively more effective in achieving embryo purification. Such bubbles apparently produce a low enough hydrodynamic displacement to allow bubble contact with embryos, thus allowing attachment to occur. Additionally, such bubbles do not generate enough shear force to dislodge attached embryos.

Another aspect of the separation process relates to the physical nature of the gas present in the bubbles, i.e., the selectivity of the gas bubbles for the embryos or seed coats. Air is approximately 21% oxygen and 78% nitrogen. Oxygen and nitrogen are both covalently bonded diatomic molecules and have a strong affinity for the similarly covalent (nonpolar) waxy portions of the embryos, such as cotton embryos. In contrast, such gases are less efficient in attaching to the relatively polar endosperm debris, which remain floating in the medium. In short, the bubbles compete with the aqueous fluid (e.g. water or mannitol/water) to attach to the waxy surface of the embryos. Since both oxygen and nitrogen molecules exceed water molecules in their covalent character, they attach preferentially to the embryo surface. Thus, the relatively lipophilic nature of oxygen and nitrogen and the relatively hydrophilic nature of the aqueous medium explains the binding of bubbles to lipophilic portions of, for instance, the cotton embryo surface. Alternatively, bubbles were found to efficiently attach to soybean seed coats which rose to the "froth" at the liquid-air interface, while soybean embryos, including soybean embryonic axes and cotyledons, were found to remain in the liquid phase. Thus, agents that differentially attach to various seed components and direct them to distinct locations, phases, or fractions may be utilized to enrich a given location, phase, or fraction for a seed component, such as an embryo or a portion of an embryo.

In one embodiment, air is used for preparing bubbles. Other useful gases in practicing this invention include $O_2$ or $N_2$, as well as covalent inorganic gases other than $O_2$ or $N_2$ including noble gases, such as argon. Covalent organic gases such as methane, ethane, and propane and other lipophilic gases or gas mixtures that do not seriously affect the viability and transformability of the corn embryos may also be used.

In the broadest sense, the "bubbles" may be made of any material that displays preferential binding to the embryos, including solids or liquids or mixtures thereof that selectively attach to embryo surfaces. Shapes such as a moving plane surface, e.g., a belt or disk to which embryos would selectively attach may be utilized. In one embodiment, embryos floating on the surface of liquid medium were preferentially attached to a sheet of hydrophobic filter paper (Whatman PS water repellent phase separating paper, impregnated with silicone). In another embodiment, canola oil mixed with a suspension of embryo and debris preferentially attached to the embryos, and carried them to the surface as the oil rose to the surface.

Bubbles coming into contact with each other can merge in milliseconds. Stabilizing the bubbles as they rise preserves an appropriate bubble size distribution as well as promotes a stable froth at the top of the flotation liquid. Several surfactants were shown to be useful in preventing coalescence and stabilizing bubbles. Preferably, the surfactant is an ionic or non-ionic surfactant, such as a polyether. The polyether may be PEG. The PEG can have an average molecular weight of about 100, 300, 400, 600, 900, 1000, 1450, 3350, 4500, 8000, and 9000. Preferably, the PEG has a molecular weight of about 8000. The PEG is used at a water soluble concentration sufficient to prevent premature coalescing of bubbles. Another suitable polyether is PPG. The PPG has a molecular weight of about 340 to about 3500. Preferably, the PPG has a molecular weight of 340. The PPG can be used at a water soluble concentration sufficient to prevent coalescing of bubbles.

In one embodiment, bubbles may be produced by a fritted fine pore glass dispersion tube (Chemglass, NJ, USA) connected to an aquarium pump for pumping air through a sterile filter and into the glass dispersion tube for creating bubbles. The dispersion tube can be placed into a container such as a graduated cylinder or a beaker containing a mixture of embryos and debris in a suspension. However, the strong convection currents created by the large population of bubbles generated by this device produced enough shear force to reduce its effectiveness in separating embryos from debris. Alternatively, the bubbles may be produced by another method, such as a multiple point source bubble generator (e.g. a bubble dispersion device utilizing limewood splinters, or a ceramic surface with pores).

In some embodiments, a surfactant may be used to stabilize the bubbles and prevent their coalescence. The surfactant may be an ionic or a non-ionic surfactant. The surfactant is used at a water soluble concentration sufficient to prevent coalescence of the bubbles. In certain embodiments the surfactant is a polyether. In particular embodiments, the surfactant may be PEG or PPG. The molecular weight of the PEG surfactant may be from about 100 to about 9000 daltons, for instance about 100, 300, 400, 600, 900 1000, 1450, 3350, 4500, 8000 or 9000 daltons. Alternatively, the surfactant may be PPG, and the molecular weight of the PPG may be about 340 to about 3500 daltons, for instance about 340 daltons.

The bubbles may be produced by a means for creating and dispersing bubbles. For instance, a fine pore glass dispersion tube or sparger may be connected to an aquarium pump and placed in a container holding a mixture of embryos and debris in suspension. In certain embodiments, the bubble production and dispersion device comprises multiple point sources of bubbles, such as individual splinter of limewood. The splinters may be inserted into a matrix, such as a length of silicone tubing, and optionally coiled into a spiral and secured.

When embryos have been carried to a liquid interface by the bubbles, they may be removed from the surface froth by a suitable means, such as overflow by gravity, or a skimmer or vacuum device. The device may be automated.

Combination Device and Methods for Extracting and Separating Embryos

In further embodiments, the invention provides a combination device for extracting and separating embryos suitable for tissue culture. The extractor may be in communication with the separator, or they may be operated separately. The extractor comprises one or more fluid jets for extracting an embryo, such as a corn embryo, from a seed. The seed may be a kernel on a corn cob. More than one fluid jet may be directed at a single cob, and more than one cob may be simultaneously placed in the extractor.

After extraction of embryos from kernels, embryos and debris may fall into or be conveyed to an embryo separator comprising, for instance, a flotation chamber. The means for conveying to and from the flotation chamber may be a screened conveyor belt or belts, or mesh that may separate debris from embryos via size-exclusion. The belt or mesh may be a woven or molded thermoplastic. Upon adding embryos to the flotation chamber, embryos are preferentially separated from other debris, for instance via the described bubble method, and float to the surface where they may be removed via an opening or chute.

Thus, corn ears may be harvested, and embryos may be excised using a fluid jet. The top of the kernel may be removed in order to facilitate embryo excision by the fluid jet, and the kernel contents are substantially removed from the ear by the jet. The fluid jet may be a liquid jet comprising the described excision media with an osmolality of about 0-600 mOsm/kg. In particular embodiments, the excision medium is a sterile solution, for instance 0.1-0.2 M mannitol. Embryo as well as non-embryo (e.g. endosperm) tissue may be extracted from the cob and kernel by the jet. Subsequently, embryos may be substantially separated from non-embryo tissue, for instance by the disclosed separation methods, and apparati, using shear forces including flotation of embryos, by sieving, or the like. However, even embryos, or groups of embryos, that are not separated from other tissue comprising a kernel may be of use for subsequent tissue culture, including transformation and regeneration of transgenic plants.

If a flotation method is used for separation, a surfactant may be added to the media in which the embryos are separated. The surfactant, such as PEG or PPG, reduces coalescence of bubbles, maintaining an effective average bubble size to promote efficient separation of embryos from non-embryo tissue, and the deposition of embryos at an air-liquid interface where they may be harvested by fluid flow, by a skimmer, by a vacuum device, or the like. By such methods, substantially excised and separated plant embryos may be obtained, suitable for production of transformed tissue and transformed plants.

Transformed Plants and Methods of their Production

The present invention also provides a transformed plant, such as a corn, cotton, or soybean plant, produced by the steps including (a) providing at least one transformable target tissue using one or all of the methods or apparatuses described herein; (b) introducing a selected nucleic acid molecule into the transformable target tissue to produce a transformed explant; and (c) growing a transformed monocot plant from the transformed explant. Preferred plants of the invention include transformed members of the family Poaceae, including grain crops such as corn (maize), millet, wheat, and rice; as well as transformed dicot plants such as cotton or soybean plants.

Particularly preferred monocot plants include transformed *Zea* species, such as *Zea mays*. Transformed corn preferably contains at least one heterologous nucleic acid molecule capable of conferring a desired trait to the transformed corn, such as herbicide resistance, pest resistance, cold germination tolerance, water deficit tolerance, increased productivity, increased yield, and the like. Practical transformation methods and materials for making transgenic monocot plants of this invention (for example, various media and recipient target cells, transformation of immature embryos, and subsequent regeneration of fertile transgenic plants) are disclosed, for example, in U.S. Pat. No. 6,194,636 to McElroy et al., U.S. Pat. No. 6,232,526 to McElroy et al., United States Patent Application Publication Number 2004/0216189 to Houmard et al., United States Patent Application Publication Number 2004/0244075 to Cai et al., which disclose methods useful with corn, and United States Patent Application Publication Number 2003/0024014 to Cheng et al., which discloses methods useful with wheat, all of which are incorporated by reference herein. Single or multiple heterologous nucleic acid molecules may be used for transforming the monocot plants of the invention; for example, constructs for coordinated decrease and increase of gene expression are disclosed in United States Patent Application Publication Number 2004/0126845 to Van Eenennaam et al., which is incorporated by reference herein. Numerous methods for transforming other plants, including dicot plants, are well known in the art. For instance, methods for transforming soybean and cotton plants are described in U.S. patent application Ser. No. 12/045,502 or U.S. Pat. No. 7,002,058, each of which are herein incorporated by reference.

In certain embodiments, for instance when an *Agrobacterium*- or other bacterially-mediated genetic transformation method is utilized, the culture response or transformation frequency of embryogenic tissue isolated by the methods of the present invention may be enhanced by use of a co-culture medium comprising a bactericide such as carbenicillin, and/or 2,4-D at a concentration of about 0.5-1.5 mg/L. In a particular embodiment, the co-culture medium comprises the ingredients of Medium 1898 of Table 9.

The seeds of resulting transgenic, fertile plants of the invention can be harvested and used to grow progeny generations, including hybrid generations, of transformed plants that include the heterologous nucleic acid molecule in their genome. Thus, the present invention includes both primary transformed plants ("R0" plants, produced by transforming embryos provided by a method of invention) and their progeny carrying the heterologous nucleic acid molecule. Such progeny transgenic plants can be prepared by crossing a transformed monocot plant of the invention having the heterologous nucleic acid molecule with a second plant lacking the construct. Also, a transformed monocot plant of the invention can be crossed with a plant line having other heterologous nucleic acid molecules that confers another trait to produce progeny plants having heterologous nucleic acid molecules that confer multiple traits.

In order to provide a clear and consistent understanding of the specification and the claims, including the scope given to such terms, the following definitions are provided.

"Embryo" is a part of a seed, consisting of precursor tissues (meristematic tissues) for the leaves, stem, and root, as well as one or more cotyledons. Once the embryo begins to grow (germinate), it becomes a seedling plant.

"Meristem" or "meristematic tissue" consists of undifferentiated cells, the meristematic cells, which differentiate to produce multiple plant structures including stem, roots, leaves, germline tissue and seeds. The meristematic cells are the targets for transformation to obtain transgenic plants.

"Explant" is a term used to refer to target material for transformation. Therefore, it is used interchangeably with "meristematic tissue" or "embryo" in the embodiments herein.

EXAMPLES

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Method to Extrude Multiple Corn Embryos

This example describes a method using mechanical positive pressure from an extruder device to produce embryos suitable for tissue culture or genetic transformation.

The tops of kernels were sterilely removed from an immature ear of corn (Zea mays) with a vegetable peeler. The peeler was pushed from the basal end of the corn ear to the apical end using a slight sawing motion to obtain a quick, sharp truncation of the kernels. While in this instance the individual kernels are truncated to expose the interior tissues, in other embodiments, it may be necessary only to ensure that an opening (such as a puncture or incision or abrasion) is made in the pericarp without actual removal of pericarp material. Where intact embryos are desired (for example, intact embryos for transformation), the size of any opening is preferably sufficient to allow removal of the embryo without damaging it. Opening of the pericarp can be accomplished by using any suitable device, including, but not limited to, blades and abrasive materials. For example, a vegetable peeler is designed to be relatively safe and fast to use; it has a regulated cutting depth and also requires less skill to use than a scalpel. Other tools with similar functions can be employed. The devices for opening the pericarp are preferably sterilizable, for example, by autoclaving or heating or by chemical sterilization. These pericarp treatment processes can be automated; for example, a blade or blades or abrader can be motorized.

A sterile extruder (in this case, a 4 millimeter diameter rod) was pushed against the base of the truncated kernels. Other suitable extruding devices may be employed. Preferably, such devices should have a size and shape capable of applying a relatively localized force to the base of the truncated kernels to eject the embryos and endosperms. Preferably, the force applied is of sufficient magnitude and is applied in a suitable direction such that the advancing extruder does not "ride up" over the forward kernels. The trailing edge of the extruder preferably also provides a surface on which the ejected embryos and endosperms accumulate; for example, a flat piece of stainless steel with a rounded front edge could be used. In this example, the embryos were gently squeezed out from the pericarp, followed by the endosperms. The extruded embryos and endosperms came to rest on the top of the advancing extruder rod, and were not crushed during the process.

The mixture of embryos and endosperms was washed with an aqueous fluid medium (e.g. water, liquid medium, or saline) onto a sterile mesh having diamond-shaped openings (about 2×3 millimeters). The endosperms were observed to be largely retained, and the smaller embryos and some smaller endosperm debris were washed through the screen into a collecting receptacle. The collected embryos were washed twice to remove small debris.

The washed embryos were further purified by a flotation process. In the first step of the floatation process, the aqueous fluid medium was thoroughly withdrawn from the collecting receptacle, which was allowed to dry briefly (for example, about a minute), such that remaining aqueous medium withdrew from the waxy surface of the embryos, exposing them directly to the air. New aqueous medium was added, and the majority of the embryos floated because their waxy surface was not rewetted by the fluid. Non-embryo tissues such as endosperm debris remained submerged in the medium, and a clear separation of embryos and non-embryo tissues was obtained. The floatation of the extruded embryos could be improved by more rapid, complete, or reproducible withdrawal of the aqueous medium, such as through the use of aspiration, or by capillary action (e.g., use of a sterile absorbent placed in the collecting receptacle to absorb the fluid away from the extruded embryos).

A yield of approximately 100 embryos was isolated in this preliminary experiment, wherein only a portion of the embryo-endosperm material from the entire ear was processed. These results demonstrate that methods of the present invention are practical and convenient for harvesting large numbers of immature embryos from corn cobs.

The embryos isolated by a method of the invention may then be used in tissue culture procedures, for example, regeneration methods to generate transgenic corn plants. Transfer of the isolated embryos to culture medium was easily done by placing forceps, with the tips closed together, underneath the floating embryos, lifting them free of the liquid with the forceps and placing them on culture medium. Another technique could be to pick the isolated embryos up with an instrument that has a hydrophobic surface. An additional technique would be to transfer embryos by hydrophobicity, for example, transferring them to the medium surface by a small puff of air or sudden mechanical movement, such that their kinetic energy exceeds the hydrophobic force that holds them to the instrument.

Example 2

Visual Confirmation of Embryo Size

This example describes an improvement to one embodiment of the method of the present invention, as described in Example 1. Using the approach described in Example 1, immature corn embryos need to be as close to the truncated part of the kernel in order to be ejected in the greatest numbers. Variation in immature corn embryo size is an important consideration in gauging the amount of kernel top to remove. Embryos tend to be largest in the mid-section of the ear, with somewhat smaller embryos towards the ends. Smaller embryos, e.g., smaller than about 1.5 millimeters in length are more difficult to remove unless they are close to the truncation.

One way to ensure that enough of the kernel has been decapitated above embryos of varying sizes is to observe the cob during the decapitation process under low magnification. For example, low magnification goggles (e.g. Donegan Opti-VISOR headband binocular magnifier equipped with a No. 7 lens, which provides a 2.75× magnification) were used to aid visual confirmation of embryo size and suitable truncation of the pericarp. If the first cut did not remove enough of the kernel apex, a second cut could be made. Other low magnification devices, using the same or similar magnifications could be used. For example, available lenses for the Opti-VISOR provide magnification ranging from 1.5 to 3.5×.

Example 3

Extrusion of Embryos and Endosperms

This example describes an improvement to one embodiment of the method of the present invention, as described in Example 1. Powered devices may be used to assist in the extrusion of embryos and endosperm. For example, a power chisel such as a WeCheer 320 power chisel (WeCheer Industrial Co., Taichung Hsien, Taiwan, R.O.C), fitted with a rounded extruder device, can be used to reduce the force a person needs to exert to eject the embryos and endosperms. Other powered devices are available and can be similarly used. Preferably, the "chisel" portion of such a tool (or any part of the tool that might come into contact with the embryos) can be conveniently sterilized, for example, by insertion into a bead sterilizer.

In one experiment, the blade of a stainless steel weighing spatula was bent back on itself to provide an extruder device having a rounded leading edge. After insertion into a WeCheer 320 power chisel, a portion about 10 centimeters long extended out from the power chisel's chuck. This assembly was used to eject the embryos and endosperms from individual rows of decapitated kernels. As the extruder device (modified spatula) moved down a row of kernels, a slight tendency for the spatula to slide off center to the left or right was observed; however, this tendency could be corrected by including a small keel-like extension of the spatula on each outer edge.

Example 4

Mechanized Embryo Extrusion

This example describes an improvement to one embodiment of the method of the present invention, as described in Example 1. Mechanization of the embryo extrusion process can be achieved by use of a suitable device, such as, but not limited to, the device described herein and schematically diagrammed in FIG. 1. This device includes two motors. The first motor (D) is a stepper motor that can rotate the corn ear (A) so that new rows of kernels are exposed to the two extrusion rods (G), which apply force to squeeze the embryos and endosperms out of their pericarps.

Rods (G) are conveniently located on opposite sides of the ear in order to balance the pressure applied to the ear relative to the ear's longitudinal axis. However a single rod can be used, or more than two rods; where multiple rods are used, it is preferable that they are positioned so as to evenly distribute the resulting mechanical pressure around the ear. The rod need not be a straight rod; in one embodiment of the device, a flexible "collar" encircling the circumference of the ear is used instead of a rigid rod. In another embodiment, multiple short rods or rollers are arranged in a flexible, circular configuration that can be slid along the ear's longitudinal axis, applying mechanical pressure to many or all rows of kernels simultaneously.

The second motor is connected to the pinion gear (E) connecting to a rack (F) so that up and down linear motion of the ear occurs. The base of the ear is held firmly to a handle (B) by means of a screw extending from the handle down into the base of the ear. The narrowed middle portion of the handle is square so that it will not rotate unless the holder (C) to which it is attached is rotated by the stepper motor (D).

Before insertion into the machine, the tops of the kernels are decapitated as in Example 1 so that the embryos and endosperms can be squeezed out. To start the process, the ear is lowered until the two rods (G) are near the base of the ear just below the handle (B). Then the rods are pressed against both sides of the ear and the rack and pinion assembly draws the ear upward. As this happens, the embryos and endosperms are removed from a couple of rows, fall downward into the collection dish (H) resting on the base (I), and collect in a pile (J). When the rods approach the apical end of the cob, the cob is withdrawn upward to its original starting position and rotated slightly by the stepper motor until new rows of kernels come into position.

Various degrees of automation of this machine are possible, including sensors to automatically adjust the vertical starting and finishing positions as well as the rotary start and finish positions. A rack and pinion is not the only method by which linear motion can be obtained. Pneumatics or hydraulics may be preferred for some applications. Rods (G) can be automatically opened by a suitable mechanism. When a new ear is loaded, it may be preferable to raise the ear to a position high enough to clear the rods.

Example 5

Hydrophobic Separation of Embryos

This example describes a modification to one embodiment of the method of the present invention, as described in Example 1. In separation applications the material of interest frequently appeared at the interface of dissimilar phases (for example, between aqueous and lipophilic solvents). Removing the material of interest from such an interface can pose problems, and has in the past been a manual process involving close contact with the extractant and the material to be extracted. Often the only way to successfully separate out a component is to use a material of the same polarity or hydrophobicity/hydrophilicity. In the case of immature corn embryos extruded by a method of the invention, the embryos are found at the aqueous/air interface. The corn embryos' surface is waxy, i.e., lipophilic or hydrophobic, and when an embryo cuticle is contacted with a substance of similar hydrophobicity, the embryo will tend to stick to the hydrophobic surface. The embryo's hydrophobicity reduces the surface tension of the water around it, which helps the embryo to "float" at the surface of the aqueous/air interface.

One approach that takes advantage of these physical characteristics would be to touch the floating embryos with a hydrophobic material such as hydrophobic filter paper, e.g., Whatman No. 1 PS paper, which is a water-repellant phase separating paper impregnated with silicone (Whatman plc, Brentford, Middlesex, U.K.). In one example, a piece of sterile hydrophobic filter paper can be lowered onto an entire container of floating embryos and pick them all up at once. In another example, a small piece of the hydrophobic paper can be used to successively pick up a number of embryos and transfer them to the next container. In a third example, either a small piece of the hydrophobic paper or a hydrophobic pipette tip would be used to contact and pick up individual embryos and then dispense them with a puff of air from the pipettor. Ordinary pipette tips could also be modified for such use by inserting a pipette tip into a short length of hydrophobic tubing (for example, silicone tubing); the embryo could then be picked up by hydrophobic attraction to the distal end of the hydrophobic tubing, and then released by dispensing a puff of air from the pipette. Reduced surface tension around the hydrophobic embryos helps them float on an aqueous surface, and the floating embryos could also be transported by moving them on the aqueous surface (for example, by an air jet directed at the embryos). Picking up and dispensing of embryos can be automated using modifications of existing devices, such as machines designed for colony picking or for retrieving protein spots on stained 2-dimensional protein gels.

Example 6

Further Methods of Ejecting or Extruding Embryos

The method of the present invention encompasses the use of various types of force, or combination of forces, for separating the embryo from its seed. This example describes further embodiments. In one basic method as described in Example 1, mechanical positive pressure is applied to the base of a truncated seed (such as a corn kernel) to eject the embryo out through the truncated top of the seed.

In another embodiment, centrifugal force can be used to eject the embryo. For example, a corn ear (the kernels of which have previously been truncated) could be spun about its longitudinal axis at a speed sufficient to eject the embryos and/or endosperms in a radial trajectory. Spinning could be achieved by any suitable technique, such as, but not limited to, contacting the apical end of a corn ear with a freely rotating cone, wherein the rotation of the ear is kept within a limited longitudinal range, for example, by attaching the basal end of the ear to a handle which is then inserted in a holder within which it can rotate. In one exemplary embodiment using centrifugal force, about a third of the top of each kernel on a corn ear was removed with a scalpel, and the ear rolled on a surface to loosen the embryo and endosperm within the kernels. The ear was snapped into two pieces, each about 750 millimeters in length. Each piece was placed in a 250-milliliter centrifuge bottle with about 100 milliliters of water. These were centrifuged 15 minutes at 5000 rpm to eject the embryos. Examination of the ears after centrifugation showed that, in some portions of the ear, all the embryos had been removed by the centrifugation, whereas in other areas, few or no embryos were removed. The ejected material was centrifuged and the supernatant removed to leave a slurry, which contained intact embryos (estimated to include about 20 percent of the total number of embryos). In another example, an immature ear of corn is harvested (typically between about 10 to about 14 days post-pollination). The ear is disinfested, and under sterile conditions the top of each kernel is cut off. The ear is mounted on a drill bit on an electric drill (or a similar device) and the ear is surrounded by a large sterile collection vessel (e.g., a large glass beaker). The ear is spun at a rotation sufficient to eject the immature embryos, and the ejected tissues are collected from the sterile container. Immature embryos are collected, for example, by manual collection, or by rinsing the container with sterile tissue culture medium and recovering an enriched fraction containing the embryos (e.g., by sieving, by the use of a liquid density gradient, or by other methods to separate embryos from non-embryo tissues as described elsewhere in this disclosure). The immature embryos (or callus derived from the immature embryos) can be used subsequently for transformation. Improved results using these and other centrifugation methods can be obtained by determining preferred centrifugation times and speeds by routine testing.

Another embodiment employs bulk maceration of kernels. An immature ear of corn is harvested (typically between about 10 to about 14 days post-pollination). The ear is disinfected. The pericarp can be opened under sterile conditions or the kernels can be left intact. The kernels are removed from the cob by any suitable procedure, including, but not limited to, using a scalpel or other bladed tool. The kernels, once separated from the cob, are placed in tissue culture medium. The kernel-medium mixture can be subjected to further tissue disruption using a suitable cutting device, such as, but not limited to, a blender. Immature embryos are collected, for example, by manual collection, or by rinsing the container with sterile tissue culture medium and recovering an enriched fraction containing the embryos (e.g., by sieving, by the use of a liquid density gradient, or by other methods to separate embryos from non-embryo tissues as described elsewhere in this disclosure). Immature embryos (or callus derived from the immature embryos) can be used subsequently for transformation.

In a further embodiment, fluid jets (of gases or liquids or combinations thereof) could be used to dislodge embryos. One example of this approach is to automatically rotate a corn ear in a stepwise or continuous (helical) manner past a stationary jet, collecting the ejected material containing the embryos and further isolating the embryos if necessary, for example, by size separation on a mesh or screen or the like. Where the corn ear is vertically orientated (with respect to its longitudinal axis), it may be preferred to rotate the ear in an upward helical direction, or otherwise move the ear relative to the jet so that extracted embryos tend to wash downward.

In yet another embodiment, linear deceleration or linear acceleration could be employed to dislodge or eject the embryos. For example, a corn ear could be administered a shock parallel to the ear's longitudinal axis and of sufficient force to eject the embryos and endosperms. A corn ear could be enclosed in a suitable sterile, high impact-resistant holder, which could be subjected to sudden acceleration or deceleration, for example, by a sharp impact (e.g., as from a mallet).

Another improvement to the method would be to facilitate ejection or extrusion of the embryo from the truncated seed. For example, embryos could be loosened or dislodged within their native position within the seed by applying a force to the tops of intact seeds (e.g., by applying a roller or other means of applying pressure to the tops of rows of corn kernels in an intact ear or rolling or pressing the ears themselves on a surface prior to decapitating the tops of the kernels). Embryos may also be loosened within the seed by application of vibration, for example, by ultrasound. Another approach would be to remove additional non-embryo tissue, such as additional lateral wall (pericarp) material, before embryo ejection or extrusion. For example, a V-shaped knife or other instrument could be used to remove some of the lateral walls of corn kernels in rows in the ear.

Example 7

Automated Embryo Isolation Using Fluid Jet Positive Pressure

Figure 2:
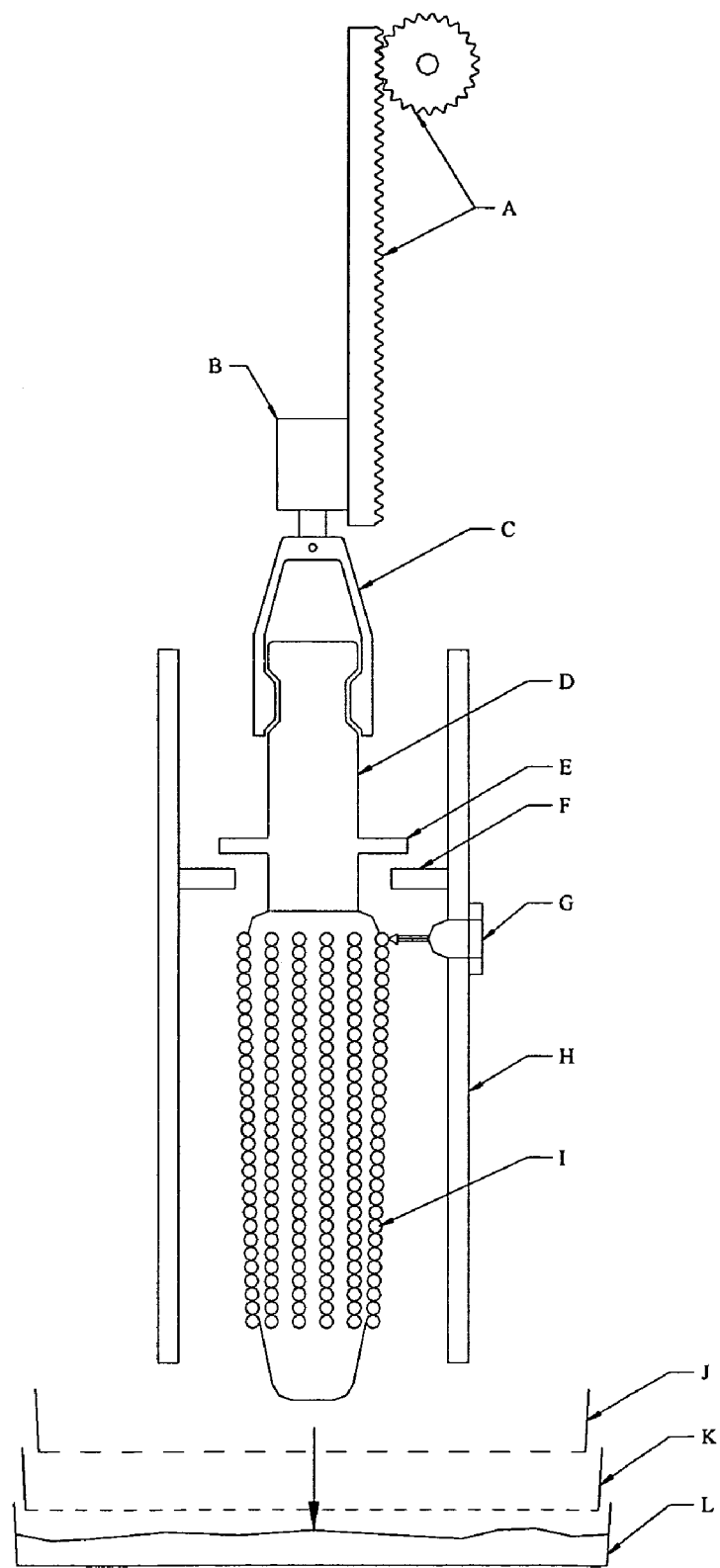
FIG. 2 depicts one embodiment of an apparatus provided by the invention that uses fluid jet positive pressure to dislodge embryos from seeds as described in Example 7. Legend: (A) robot with motion in X, Y and Z dimensions, (B) motor to rotate corn ear, (C) grasper, (D) handle to hold corn ear, (E), baffle to prevent material from splattering upwards, (F) flange to prevent material splattering upwards, (G) aperture for guiding fluid, (H) transparent tube, (I) corn ear, (J) shaking screen, (K) cheesecloth or other porous material, and (L) waste container.

This example describes a further embodiment of the present invention. In this example, an automated device uses fluid jet positive pressure to dislodge embryos from seeds. With reference to FIG. 2, a robotic grasper C (preferably capable of motion in three dimensions by means of robot A and motor B, or by an equivalent means) picks up a corn ear I (by a handle D having a baffle E) in a defined position for a rack on the robot deck. The robot inserts the corn ear into tube H (optionally made of transparent material for ease of visual observation) at a starting position below flange F. Fluid jet positive pressure is introduced through aperture G and the ear is simultaneously raised (in the Y dimension) and rotated by robot A and motor B respectively, preferably resulting in each kernel being struck by the fluid jet, causing the embryo and endosperm to be dislodged. The fluid passing through aperture G can be at least one gas, at least one liquid or any combination thereof. The fluid jet can exert force continuously or non-continuously, for example, as in pulses. As the embryos and endosperms are dislodged by fluid jet positive pressure from aperture G, they fall down to the shaking screen J, which retains the endosperms while permitting the embryos to fall through to the collecting surface K (for example, sterile cheesecloth) below. Excess fluid can be optionally collected in waste or recycling receptacle L. After completion of the embryo removal process for each corn ear, the interior of the tube can be briefly washed down manually or by automated jet above or below the flange F.

Example 8

Methods of Processing Crude Embryo Preparations

The embryo preparations obtained by methods such as those described in Examples 1 through 7 may include both intact embryos and partial embryos, which may be accompanied by non-embryo tissues, such as endosperm and glumes. Some applications may not require further treatment or separation steps, for example, in a mass transformation of such a "crude" embryo preparation where embryos (intact or partial) need not be separated from non-embryo tissue. For example, callus derived from either intact or partial immature corn embryos can be used for transformation, regeneration, and production of fertile, transgenic plants. Thus, both intact and partial embryos may serve as transformable explants and need not be separated from each other. However, in other cases it may be desirable to further purify embryos from a crude embryo preparation.

Procedures wherein some difficulties may be encountered in processing crude embryo preparations include: (1) rinsing away of non-embryo tissue (e.g., cell debris, starch grains, undesirable proteins), (2) efficiently removing excess liquid from embryos after extrusion or rinsing using liquid, and (3) adding liquid with minimal turbulence so that the embryos float and do not become submerged.

A porous material is useful for separating non-embryo tissue from embryos. Any suitable porous material can be employed, preferably having a mesh or hole size small enough to retain embryos but let smaller, non-embryo tissues or debris pass through, and capable of being sterilized (e.g., by autoclaving, heat, irradiation, or chemical sterilization). Suitability of materials is easily judged or tested by simple experimentation by one skilled in the art. Examples of suitable materials include cheesecloth or other woven material, and other meshes or screens. In some embodiments, perforated solid materials can be used, including perforated ceramics, polymers, metals, or glasses (for example, in the form of a Büchner or similar separatory funnel). Cheesecloth of appropriate gauge, for example, has a mesh size small enough to retain embryos but allows smaller debris to pass through, and is autoclavable. Cheesecloth can be attached to a frame or collar (for example, the frame holding embryo collecting surface K in FIG. 2 and described in Example 7) to allow the cheesecloth and all the retained embryos to be simultaneously submerged for easy rinsing. For example, cheesecloth can easily be attached to the frame by means of an elastic band or the like (e.g., silicone tubing); such frames are easily manufactured, for example, from a beaker or graduated cylinder made of autoclavable material (e.g., polypropylene, polymethylpentene, polycarbonate, or autoclavable glass) cut into sections. Cheesecloth has strong capillarity, allowing liquid to be efficiently pulled away from the embryos, thus exposing their waxy epidermis to air prior to flotation. In the flotation step, the cheesecloth is simply submerged in aqueous liquid, allowing the embryos to float off.

Example 9

Substantial Isolation of Embryos Using a Fluid Jet

This example describes a further embodiment of the present invention. In this example, multiple embryos were dislodged from seeds by fluid jet positive pressure.

In the simplest example, a 200-microliter pipette tip was attached to a vertical sink nozzle with Parafilm®. When the tap water was turned on a jet emerges from the pipette tip with considerable force. The tap water pressure was estimated to be about 60 pounds per square inch. This fluid (liquid) jet was trained on an immature corn ear (contained in a beaker) wherein the kernels had been decapitated as described in Example 1. As the jet stuck each kernel, the endosperm and embryo were ejected, and collected in the beaker. Since the endosperm at this stage is a relatively soft tissue it was fragmented into many smaller pieces by the jet, whereas the embryos appeared to remain intact.

The endosperm and embryo tissue dislodged by the jet was poured directly onto a No. 60 cheesecloth (other suitable porous material, such as hydrophilic mesh of the appropriate mesh size, could be substituted). Different "grades" of cheesecloth are available (for example, grades 10, 20, 30, 40, 50, 60, 70, 80, and 90, where the mesh openings decrease with higher grades), and the grade or mesh size appropriate to the average size and shape of a given type of embryo is easily selected by simple experimentation. The embryos and larger fragments of the endosperm were retained on the upper surface of the cheesecloth. Prior to the next step, the cheesecloth was allowed to partially dry by wicking away excess liquid. This pulled liquid away from the tissues and exposed the surfaces of the embryos to air. When the cheesecloth was lowered into aqueous liquid, the embryos floated because their waxy epidermis did not rewet.

In a simple set up, the cheesecloth (or other suitable porous material) can be manually stretched or held over a receptacle or waste container as the liquid holding the crude embryo preparations is poured through the cheesecloth. For sterile work, the cheesecloth can be attached to rigid frames, which can be autoclaved before use. Snap-together sieves with handles, such as those available in kitchen supply stores, could also be used in the method.

Example 10

Devices for Embryo Extraction Using a Fluid Jet

This example describes various embodiments of an apparatus for mechanically preparing multiple corn embryos suitable for tissue culture.

One embodiment includes an apparatus for preparing multiple corn embryos using a fluid jet, generally similar to the device depicted in FIG. 2. A transparent, open-ended cylinder was made by cutting the ends off a 1-liter autoclavable polymethylpentene (PMP) graduated cylinder. A pipette tip (e.g. 1250-microliter Gilson DistriTip®, tapered to avoid back-pressure build-up) was secured to the side of the cylinder and served as an aperture for guiding a fluid stream as a jet through a hole made in the cylinder's wall. Fluid (in this case, water) was fed through the pipette tip from PharMed® high pressure autoclavable peristaltic pump tubing. The water was delivered from a laboratory sink tap, but could be an aqueous fluid delivered from a pump or other source. Using a pump capable of delivering a sterile fluid is preferable when, for example, sterile culture medium or a sterile salt solution is found to be superior to water as a liquid for substantial isolation of embryos. An example of a suitable pump is a Masterflex® pump with the high pressure L/S pump head (Cole-Parmer Instrument Co., Vernon Hills, Ill.), which can deliver sterile liquid at up to 100 psi when used with high pressure tubing.

A corn ear with previously decapitated kernels was manually positioned within the cylinder. Once the ear was positioned appropriately within the cylinder, each kernel was subjected to positive pressure from the water jet. This resulted in the embryos and non-embryo tissues being extruded from the kernels. Examination of the ear after this treatment indicated efficient removal of the embryos from the kernels. The extruded material was washed down the cylinder's interior walls to an embryo collector positioned beneath the cylinder. The embryo collector included: (1) a coarse plastic screen (onto which larger debris was trapped), heat-fused to the cut-off top of a Tri-Pour™ plastic beaker and stacked above (2) a finer screen (Grade 60 cheesecloth, onto which the extruded embryos were trapped), secured with an elastic band to the cut-off top of a second Tri-Pour™ plastic beaker and stacked above (3) a waste collection beaker or other container (in which the fine debris, non-embryo tissues, and waste liquid was collected).

Figure 3:
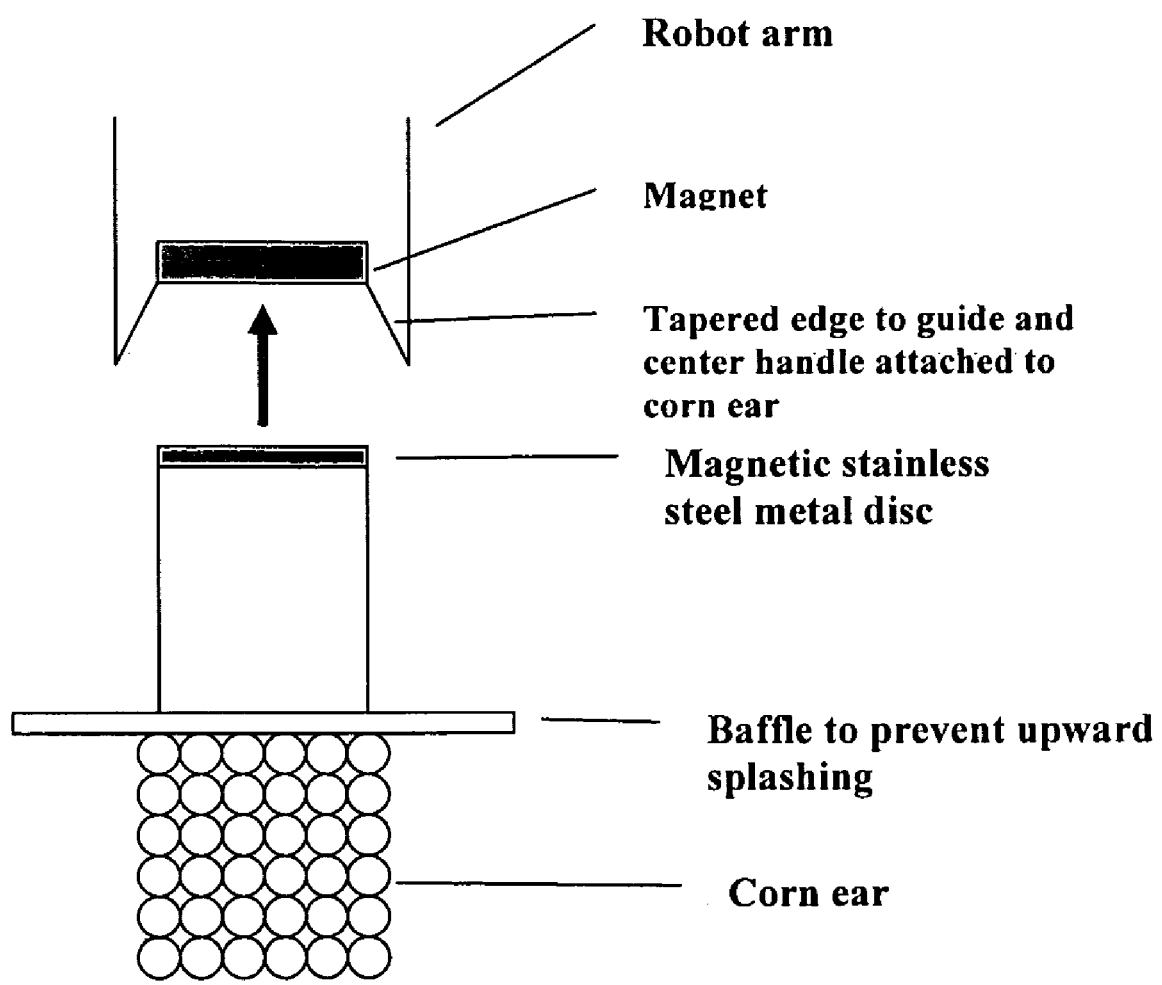
FIG. 3 depicts one embodiment of a mounting mechanism using a magnetic "handle" by which a corn ear can be secured to a robot arm, as described in Example 7.

Modifications to these and similar embodiments are easily made by one versed in the art. For example, with regard to positioning the corn ear or seed for application of the fluid jet, the ear could be held manually in place, or preferably, mounted securely within the cylinder by a movable support capable of moving the ear in three dimensions. For example, the ear could be mounted to a threaded metal or polymer rod, such as a polypropylene rod, which could be used to move the ear along its longitudinal axis as well as to rotate the ear). Another example of a mounting mechanism is depicted in FIG. 3, which illustrates a magnetic "handle" by which an ear can be secured to a robot arm.

In other embodiments, however, the corn ear or ears need not be individually secured to a holder but can be freely movable so as to allow multiple kernels to be contacted by the force used to remove the embryos from the kernels. For example, at least one ear, or multiple ears, can be borne on or held between at least one support, such as, but not limited to, at least one plane, frame, grid, screen, mesh, platform, roller, guide wire or rod, and belt, wheel, or roller conveyor. Such a support could be movable or could cause the ear or ears to move, for example, by vibration, rolling motion, gravity, or other mechanisms. Substantially isolated embryos could pass through the platform itself if the platform was porous (e.g., made of mesh). The ear or ear can also be floated on a fluid in a manner allowing each ear to rotate or otherwise move freely while afloat. The fluid, such as a liquid containing the substantially isolated embryos, could be continually drained off, optionally through a filtering or sedimenting device, or collected for centrifugation.

Devices for obtaining motion along the longitudinal axis of a corn ear include, but are not limited to, ball screw-driven slides or belt-driven slides, such as those commercially available from various manufacturers such as Techno, Inc. (New Hyde Park, N.Y.; techno-isel.com). To obtain rotary motion for rotating a corn ear, a stepper motor can be used, for example, a stepper motor attached to a slide plate. Rotary motion can also be provided by rolling devices, for example, by parallel round or tubular rollers between which the corn ear is held and rotated.

The shape of the fluid jet can be advantageously modified according to the desired application. For example, a narrow column-shaped jet of uniform diameter is useful for removal of embryos from one seed at a time. Where it is desirable to increase the rate at which embryos are substantially isolated, multiple embryos can be simultaneously removed from their seed by a fluid jet; this can be achieved, for example, by using at least one single fluid jet that covers a larger area, or by using multiple jets simultaneously. In one embodiment, multiple jets, such as multiple parallel, narrow, column-shaped jets (for example, produced by multiple nozzles similar to that used in Example 9 and optionally connected to each other by a manifold) are used to direct fluid jet positive pressure on multiple seeds to substantially isolate their embryos substantially simultaneously. Automation of these and other devices can further include optical or mass sensors to aid in positioning the ear and fluid jet relative to each other.

In another embodiment, at least one fluid jet that covers a larger area (for example, wherein the fluid jet simultaneously impacts multiple kernels, or multiple rows of kernels on a corn ear) can be used. The dimensions of such a jet preferably allow the jet to enter the kernels and wash out the embryo. Typically, corn embryos used in genetic experiments are immature and generally in the size range of about 1.8 to about 2.2 millimeters in length; the kernels holding these immature embryos are generally in the size range of between about 4 and about 5 millimeters in width. For embryos of this size, an appropriate fluid jet can be, for example, between about 0.5 to about 1 millimeter in width.

Figure 4:
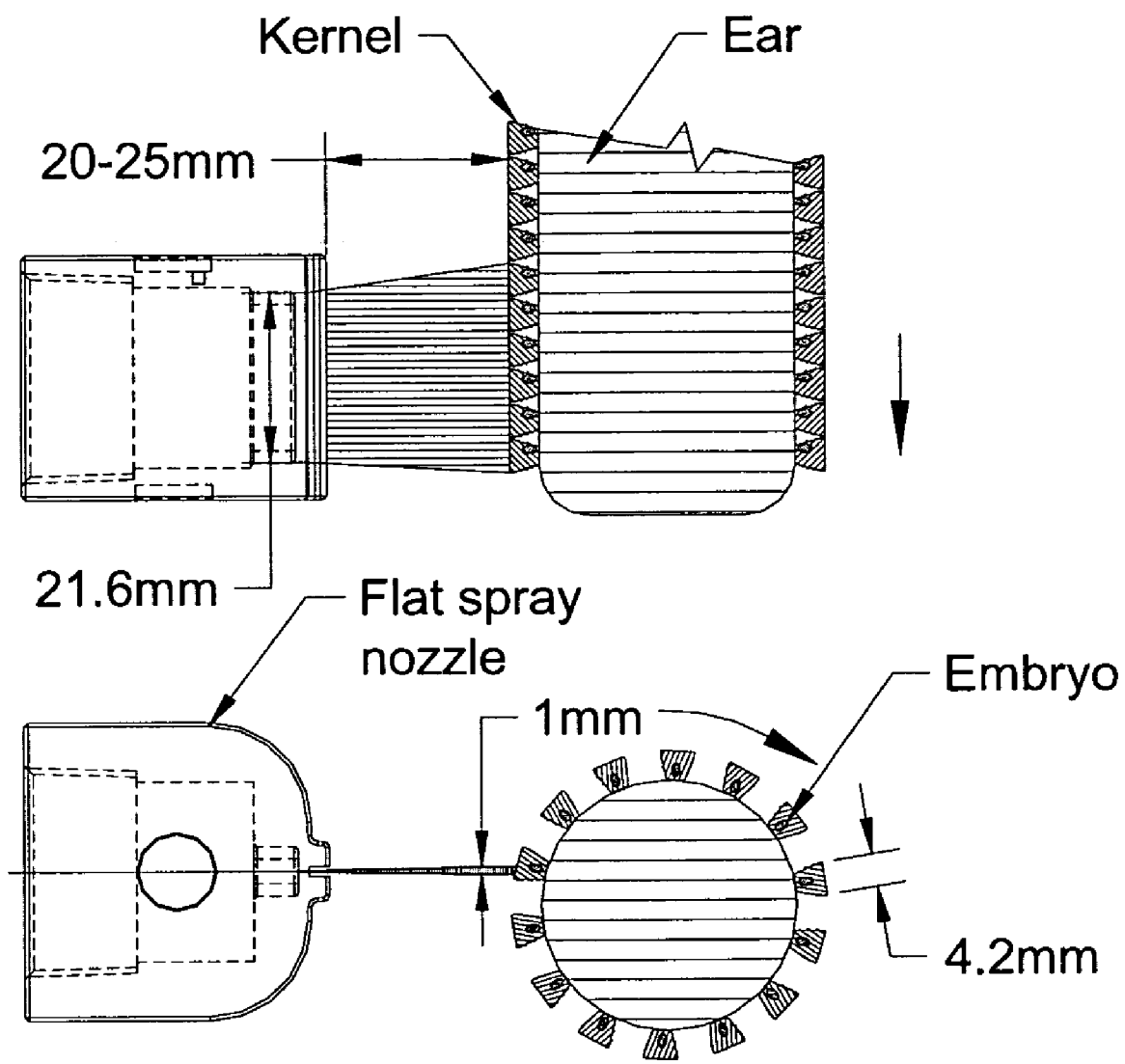
FIG. 4 depicts one embodiment of a nozzle useful in certain aspects of the invention, as described in Example 7. This nozzle generates a substantially uniform, flat sheet-like jet of fluid.

Any suitable means for producing such a larger fluid jet may be used, such as, but not limited to nozzles that generate non-columnar fluid jets. Examples of suitable nozzles include, but are not limited to, nozzles that generate a flat spray pattern and nozzles that generate a fan- or a cone-shaped spray pattern. In one example, a commercially available flat spray nozzle (number 23990-1/4-04, Spraying Systems Co., Dillburg, Pa.) was used with a Masterflex® L/S pump (model 77250-62) to pump liquid at 1 liter per minute and 30 psi; embryos were excised from a corn ear under these conditions. Another example of a preferred nozzle is a nozzle that generates a fluid jet in the form of a flat "sheet" of fluid, such as is depicted in FIG. 4. Such a nozzle preferably is capable of generating a uniform, flat fluid jet that maintains a coherent, uniform sheet-like flow for at least a distance sufficient to allow the flow to contact more than one seed (and preferably several seeds) at the same time. The novel nozzle depicted in FIG. 4 is designed to generate a uniform, flat sheet-like jet that is about 0.5 to about 1 millimeter in thickness, greater than about 20 millimeters in width, and maintains the sheet-like flow over a distance of about 15 to about 30 millimeters from the nozzle's aperture. This latter distance permits the jet to be moved along the rows of kernels with minimal adjustment needed for differences in distance between the surface of the kernels and the nozzle's aperture.

Regardless of the area or shape of the jet or spray pattern generated by the nozzle or aperture through which the liquid flows, nozzles or apertures are preferably used with flow rates and pressures sufficient to generate enough fluid force to dislodge the embryo from its seed, without damage to the embryo. In some embodiments, it is preferable to use a lower flow rate and possibly a higher pressure, to minimize consumption of fluid (such as medium) as well as to minimize the waste generated.

Example 11

Using a Gas Jet to Substantially Isolate Embryos

This example describes further embodiments of methods and devices for mechanically preparing multiple corn embryos suitable for genetic transformation or tissue culture. As described in Example 6, gas jets can also be used for the substantial isolation of multiple embryos. An apparatus similar to that described in Example 10 was modified for use with gas. A 1-milliliter pipette tip (Marsh Bio Products—ABGene, Rochester, N.Y.; catalogue number TN1300RS) was secured to the side of the one liter polymethylpentene graduated cylinder and served as an aperture for guiding a stream of air as a jet through a hole made in the cylinder's wall. Air was supplied from a compressor pressurized to between about 60 to about 100 psi. An air valve for convenience was positioned in line between the compressor and the pipette tip. The air jet emerging from this pipette tip was used to dislodge the embryos from a prepared corn ear. Examination of the kernels after they had been subjected to the air jet showed that the thick pericarp remained in place and surrounded by papery glumes, and the pericarp contents (embryo and endosperm) had been removed. Examination of the tissue retained by the grade 60 cheesecloth showed that this included dislodged embryos as well as some glumes dislodged by the high-pressure air jet. The glumes of corn have a waxy surface like the embryos and also float following the flotation procedure. Using lower air pressures can reduce glume contamination.

Example 12

Substantial Isolation of Embryos Using Other Fluid Forces

This example describes further embodiments of methods and devices for mechanically preparing multiple corn embryos suitable for genetic transformation or tissue culture. Forces exerted by fluids, other than positive fluid pressure from a fluid jet, can be used to substantially isolate embryos. In one experiment, the tops of kernels were removed from a corn ear, which was placed inside a bottle containing sterile distilled water and shaken vigorously by hand. This resulted in the substantial isolation of 90 out of the ear's 200 embryos. Another experiment repeated the preceding procedure except that the shaking was carried out in a mechanical paint shaker. In this experiment, 56 embryos were substantially isolated out of the ear's 190 embryos. In a third experiment, a similar procedure was carried out, except that the corn ear was pre-soaked in 211 medium (1 liter: N6 Basal Salt Mixture from Duchefa: 1 pkg (i.e. 3.952 g) (Gold Biotechnology Inc, St. Louis, Mo., U.S.A.); 2,4-D (1 mg/ml): 1 ml; Thiamine (0.5 mg/ml): 2 ml; Nicotinic Acid (0.5 mg/ml): 1 ml; L-Asparagine monohydrate: 0.91 g; Myo-inositol: 100 mg; MES: 0.5 g; $MgCl_2 6H_2O$: 1.6 g; Casein Hydrolysate: 100 mg; Proline: 0.69 g; Sucrose: 20 g; Agar: 2 g, pH 5.8), and the shaking was carried out in a paint shaker. In this experiment, 109 embryos were substantially isolated out of the ear's 210 embryos. In these cases, non-jet fluid force from movement of the liquid around the corn ear resulted in the substantial isolation of the embryos; the fluid force could include fluid turbulent flow, fluid laminar flow, shear from fluid flow, negative fluid pressure (for example, resulting in cavitation), or combinations thereof. Forces can also include forces generated by acoustic techniques, such as by an acoustic wave or waves (pulsed or continuous) in either gas or fluid phase.

The preceding examples (including Examples 9-11) described use of a fluid jet to remove embryos from an immature ear. During these procedures, it was observed that the fluid jet generally also caused at least part of the endosperm to be released from the kernel. The endosperm tissue was observed to be softer and more friable than the embryos, and tended to disintegrate to varying degrees (in contrast to the embryos, which tended to remain intact). It is possible that the endosperms disintegrate upon exposure to shear caused by the fluid jet. This shear is believed to be non-uniform, resulting in the variability in disintegration observed; nonetheless, a large proportion of the endosperm material that was sufficiently disintegrated to pass through the cheesecloth, leaving a retentate made up of a semi-pure preparation of embryos.

When a low-pressure jet from an ordinary laboratory squirt bottle was directed at the cheesecloth retentate, more of the remaining endosperm tissue was disintegrated further and washed through the cheesecloth, leaving behind a relatively more pure preparation of embryos. Thus it is reasonable to predict that if the retentate is uniformly exposed to a shear force of the correct intensity, all or substantially all of the remaining endosperm should disintegrate and pass through the cheesecloth. Such a shear force could be generated by any suitable means, such as, but not limited to, a single jet, multiple jets, a sheet-like or curtain-like jet, rapidly moving jets, and acceleration or deceleration of the endosperms. Additionally, if the jet used to initially release the kernel contents is designed to expose a higher proportion of the endosperms to shear during ejection, an initial higher purity embryo preparation could be obtained.

A non-limiting embodiment for applying shear to further purify embryos follows. Once the embryos and partially disintegrated endosperms are released from a cob, the remainder of the endosperm can be rapidly fragmented by fluid flow, for example, from a spray nozzle, that strikes the endosperm uniformly and simultaneously. One suitable type of nozzle is a full cone nozzle. Full cone nozzles generate a spray pattern completely filled with drops. An internal vane within the nozzle imparts controlled turbulence to the liquid prior exiting to the orifice, allowing formation of the spray pattern. Commercially available nozzles have spray patterns that are round, square, or oval. An example of a suitable full cone nozzle is known as "UniJet® Spray Nozzle, Standard Spray, Small Capacity" (Spraying Systems Co., Wheaton, Ill.; part number TG-SS0.3).

Example 13

Devices Using a Combination of Forces

This example describes several additional embodiments of the method of the invention, which use a combination of forces to substantially isolate multiple embryos from seeds.

Figure 5:
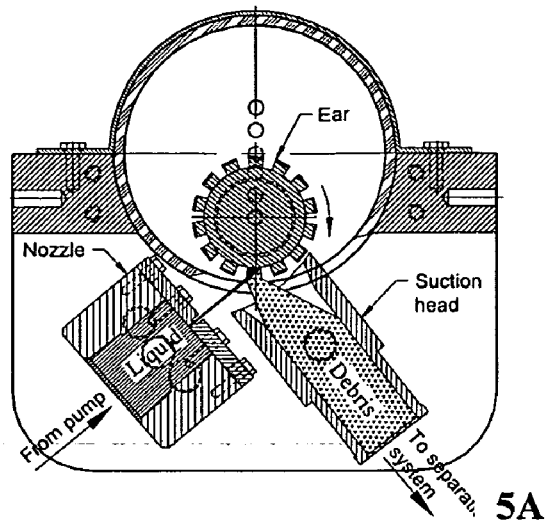
FIG. 5 depicts one embodiment of an apparatus useful in methods of the invention, as described in Example 13. This device includes a nozzle for generating a substantially flat fluid jet and an optional suction head.
Figure 5:
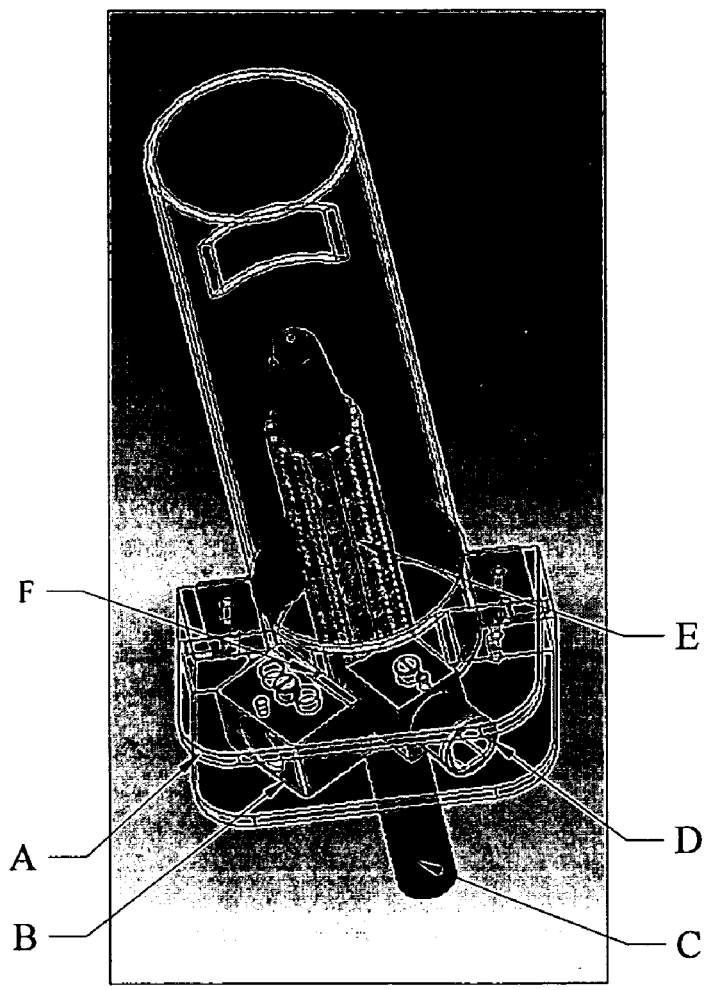

FIG. 5 illustrates a device using a larger fluid jet (as described in Example 10). This device includes a nozzle for generating a fluid flow such as a larger fluid jet (for example a flat fluid jet), and, optionally, a suction head, or component for applying negative fluid pressure (e.g., by vacuum or suction), for dislodging embryos and/or for collecting the dislodged embryos. FIG. 5A (top) depicts a cross-sectional view of an example of such a device, showing how the nozzle, optional suction head, and corn ear can be positioned relative to each other. The corn ear, nozzle, and optional suction head can be moved relative to each other; for example, the corn ear may be stationary while the nozzle and optional suction head are moved, or the nozzle and suction head may be stationary while the corn ear is moved. FIG. 5B (bottom) schematically depicts a corn ear positioned in the device, and shows the nozzle positioned to generate a flat fluid jet wherein the jet impacts multiple kernels in a row.

Figure 6:
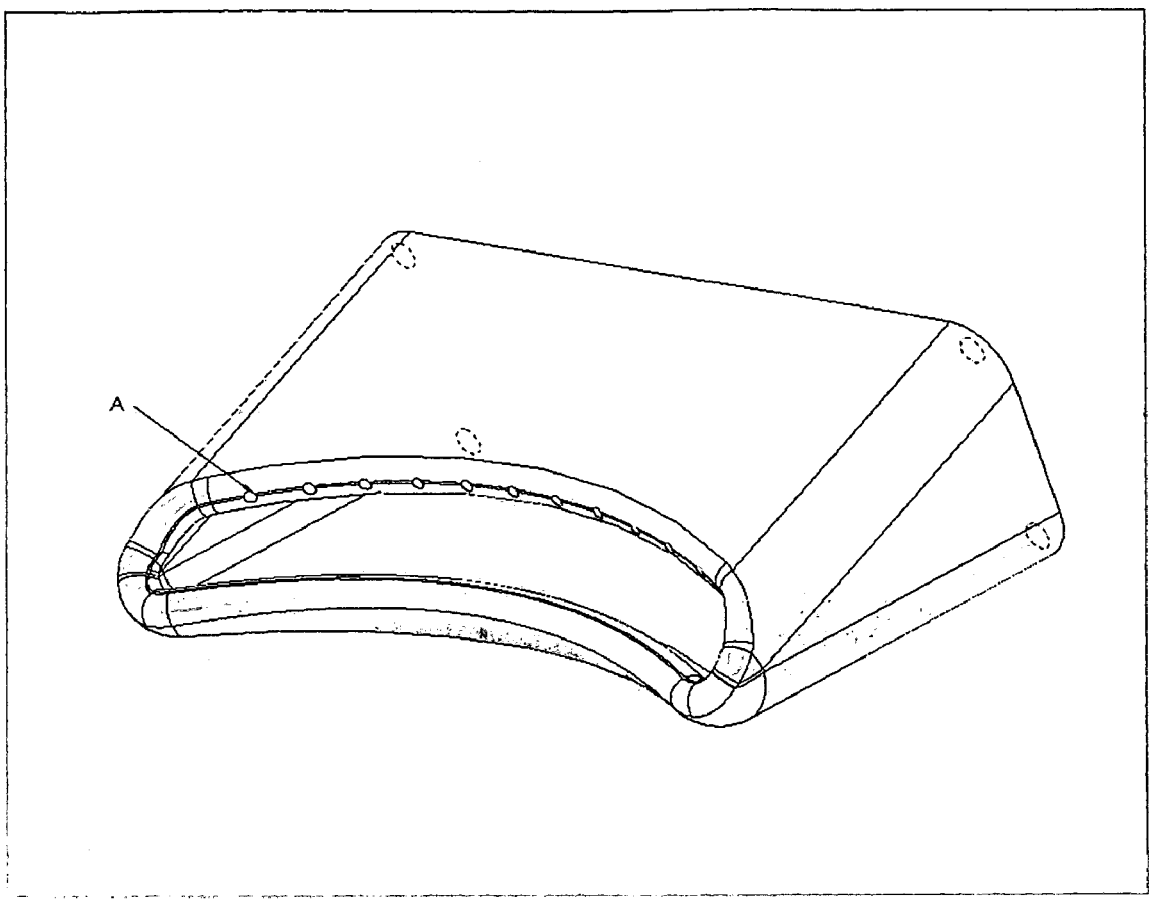
FIG. 6 depicts one embodiment of a component useful for applying negative pressure useful in methods of the invention, as described in detail in Example 13. Legend: (A) one or more apertures for guiding fluid flow.

FIG. 6 depicts an embodiment of a suitable suction head or component for applying negative fluid pressure (e.g., by vacuum or suction), such as is optionally used in the device of FIG. 5, and which can also be used on its own to substantially isolate embryos. The suction head can include one or more apertures through which negative fluid pressure can be applied. The suction head can also include a means for dispensing fluid (such as gas or liquid, e.g., water or medium), for example, multiple apertures in the suction head. For use with corn, the suction head is preferably shaped to follow the contours of a typical corn ear, and is preferably capable of entrapping embryos from multiple kernels or from multiple rows of kernels. It is envisioned that the suction head can be manufactured of a rigid material (such as stainless steel or other metals), or of a flexible material to allow easier conformation of the suction head to the contours of a corn ear, or of combinations thereof. Embryos can be substantially isolated by any combination of mechanical positive pressure (exerted, for example, by a leading edge of the suction head), negative fluid pressure (e.g., suction or vacuum), and fluid force (such as, but not limited to, positive pressure from a fluid jet, fluid turbulent flow, and fluid laminar flow entrapping material from the interior of the kernel)

Devices for applying force for substantially isolating embryos, such as are described in Examples 1, 3, 4, 6, 7, 9, 10, and the present example (including, but not limited to the devices illustrated in FIGS. 5 and 6) can be moved relative to the corn ear. The ear may be stationary, or the device may be stationary, or both can be moved. Because corn seed typically occurs in relatively uniform rows arranged parallel to the longitudinal axis of the corn ear, the device is typically moved (relative to the ear) so that the device passes parallel to the longitudinal axis of the corn ear and following a row or multiple rows of kernels. However the motion of such devices relative to the ear can follow the circumference of the ear, or can be random, or can be any combination of suitable motions.

FIG. 7A through 7C depict different views of an embodiment of a device that uses a combination of forces to substantially isolate multiple embryos from seed (in this example, corn). This device includes a head with a leading edge capable of applying a predefined amount of mechanical pressure to the base of kernels that previously have had the pericarp opened or truncated, so that the embryos are extruded from the kernels in a manner similar to those described in Examples 1, 3, and 4. The device further includes a component for applying negative fluid pressure (e.g., by vacuum or suction) for dislodging embryos and/or for collecting the dislodged embryos. The extruded embryos (and accompanying non-embryo tissues) are thus separated from the corn ear and can be collected by application of negative fluid pressure. The collected embryos and non-embryo tissues can be further separated, if desired, by suitable means, such as by size-separation, hydrophobic separation, or differential centrifugation. A variation of this device could include a means for dispensing fluid (such as liquid, e.g., water or medium), for example, multiple apertures in the suction head.

Figure 7:
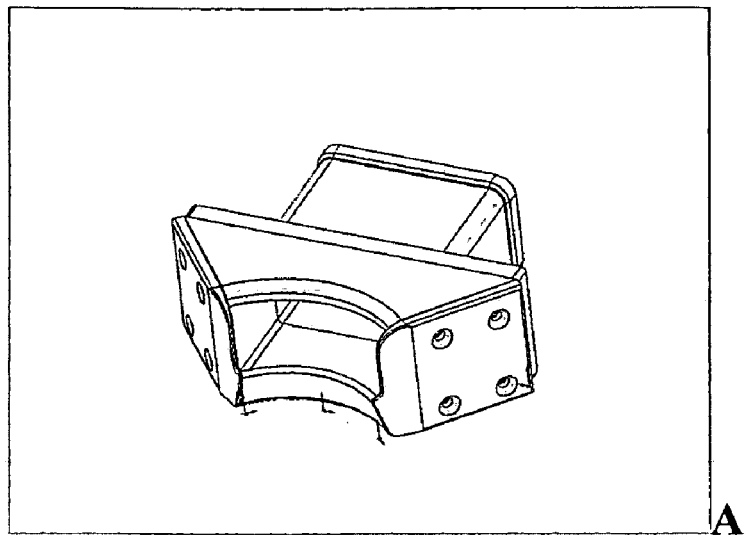
FIG. 7A-C depict different views of an embodiment of a device that uses a combination of forces and is useful in certain aspects of the invention, as described in detail in Example 13. This device includes a head with a leading edge capable of applying a predefined amount of mechanical pressure to the base of kernels that previously have had the pericarp opened or truncated and a component for applying negative fluid pressure. This device can further include a means for dispensing fluid or for guiding fluid flow.
Figure 7:
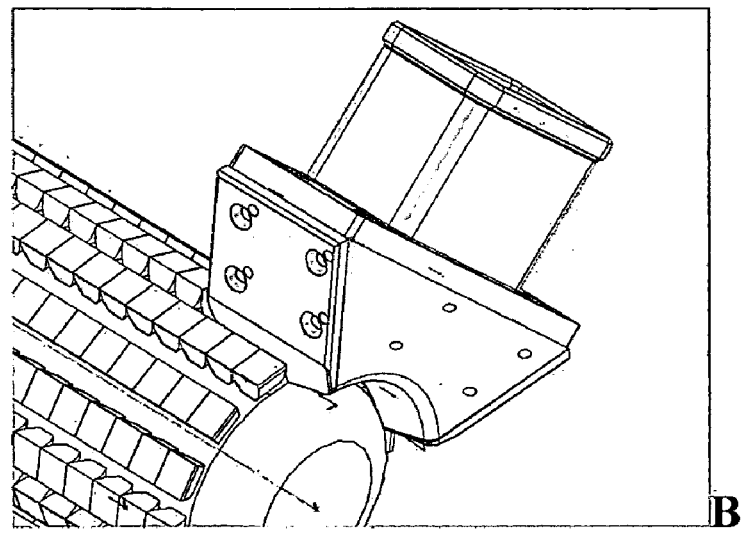
Figure 7:
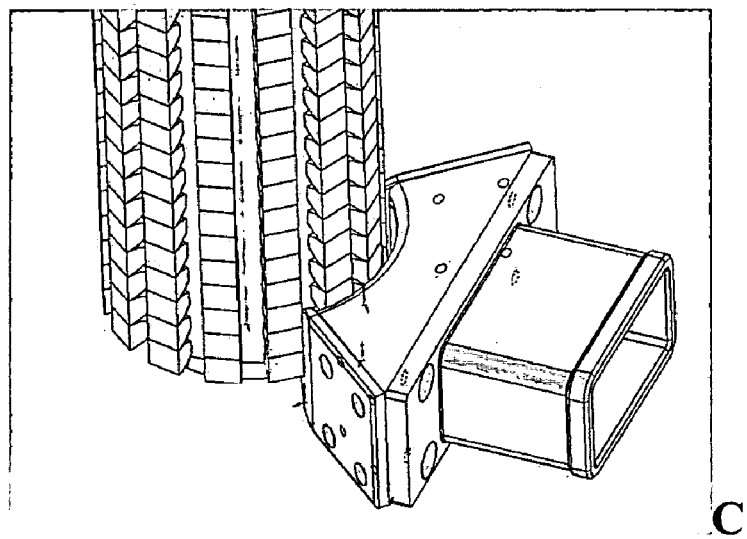

The embryo extraction devices depicted in FIGS. 5, 6, and 7 are described as illustrative examples that are not intended to be limiting. These and other such devices can include additional components, for example, means for separating the embryos from non-embryo tissues or from fluids used in the substantially isolation process.

Example 14

Viability Data

The multiple monocot embryos provided by use of the methods and devices of the present invention are most preferably embryos suitable for genetic transformation or tissue culture application such as transformation and regeneration of plants. This example further illustrates the utility of methods of the invention in providing multiple monocot embryos that are viable and suitable for genetic transformation or tissue culture. In this example, the quality of immature corn embryos obtained by different excision methods was compared in their response to transformation by *Agrobacterium tumefaciens*.

Corn embryos excised using this apparatus and method were transformed using standard methods known in the art of corn transformation. (e.g. Cai et al; U.S. Patent Application Publication 2004/0244075). Four experiments (designated A, B, C, and D respectively) were performed. Each experiment compared embryos obtained by manual excision to embryos obtained by a method of the present invention: excision by a liquid jet (experiments A, B, and D) or excision by a gas jet (experiment C). The liquid jet in experiments A and B used ordinary tap water and a nozzle made of a pipette tip. Experiment C tested a gas jet using air from a compressed-air pump and a nozzle made of a pipette tip. The liquid jet in experiment D used ½ strength MSPL medium (see Table 1 of United State Patent Application Publication Number 2004/0244075 to Cai et al.) as the liquid and a solid stream nozzle with an equivalent orifice diameter of 0.020 inches (catalogue number TP000050-SS, Agricultural Division of Spraying Systems Co., Wheaton, Ill.).

Corn ears were harvested twelve days after pollination and sterilized by soaking in a 1-liter bottle of 80% ethanol for 3 minutes. Embryos were manually excised by cutting off the top third of the kernel with a scalpel and removing the embryo from the kernel using a narrow spatula. The collected embryos were excised into 1 milliliter of ½ MSPL medium in a single microcentrifuge (Eppendorf) tube. The medium was removed and replaced with 1 milliliter of *Agrobacterium tumefaciens* prepared as described below Embryos were also substantially isolated using a fluid (liquid or gas) jet, following procedures similar to those described in Examples 10 and 11. The fluid jet was used to excise the remaining embryos on the ears after removing the top third of the kernel with a scalpel. The ear was positioned so that the fluid jet was aimed into individual cut kernels in succession to dislodge both the embryo and non-embryo tissue (endosperm). The kernel contents removed from the ear were passed through a coarse screen to remove large pieces of endosperm, and the embryos were collected on sterile cheesecloth. Embryos were transferred using a small spatula from the cheesecloth into a microcentrifuge tube containing 1 milliliter of ½ MSPL medium. After all of the embryos were collected, ½ MSPL medium was removed and replaced by 1 milliliter of *Agrobacterium tumefaciens* inoculant.

Embryos prepared by the various excision methods were subjected to the same inoculation, selection, and regeneration procedures. Suitable procedures, including descriptions of media and reagents, for transformation of plants using glyphosate selection and GFP as a reporter have been disclosed in United State Patent Application Publication Number 2004/0244075 to Cai et al.

Embryos were inoculated with 1.0 milliliters of *Agrobacterium* for 5 minutes. The contents of the microcentrifuge tube were poured onto a plate of co-culture medium, excess *Agrobacterium* was removed by pipette, and the contents were co-cultured for 18 hours at 23 degrees Celsius. Embryos were transferred next to induction MS medium, and cultured at 30 degrees Celsius for 13 days. Calli derived from the transformation were cultured at 27 degrees Celsius for 11 days prior to regeneration. At this time, GFP positive sectors were counted using a fluorescence microscope. For regeneration, calli derived from each embryo were individually transferred to MS/6 BA medium and cultured in a light room for 7 days, after which each greening callus was transferred to MSOD medium and returned to the light room for 17 additional days. Resulting shoots were transferred to Phytatrays™ containing regeneration medium (consisting of 2.165 g MS basal salts, 5 milliliters 100× MS vitamins, and 20 grams sucrose made up to 1 liter in water and autoclaved, pH adjusted with KOH to 5.8, solidified by autoclaving with 3 g Phytagel™, and with 0.75 milliliters of 1 milligram per milliliter indole-3-butyric acid, 0.5 milliliters of 1 milligram per milliliter 1-naphthaleneacetic acid, and 0.2 milliliters 0.5 molar glyphosate added). After about 3 weeks, transgenic plants were hardened off by transplanting rooted shoots in peat pots containing soil mix and grown at 26 degrees Celsius.

The results of these experiments are summarized in Table 3. The number of embryos that were transformable is estimated from the number of GFP-positive embryos.

TABLE 3

Viability and transformation frequency of excised embryos.

| experiment | excision method | number of embryos inoculated | number of GFP-positive embryos | transformation frequency | number of plants to soil | transformation/regeneration frequency |
|---|---|---|---|---|---|---|
| A | manual | 56 | 23 | 41% | 6 | 11% |
|   | liquid jet | 44 | 8 | 18% | 3 | 6.8% |
| B | manual | 22 | 11 | 50% | 6 | 27% |
|   | liquid jet | 23 | 4 | 17% | 1 | 4% |
| C | manual | 33 | 27 | 82% | n/a | n/a |
|   | gas jet | 61 | 19 | 31% | n/a | n/a |
| D | manual | 36 | 17 | 47% | n/a | n/a |
|   | liquid jet | 166 | 51 | 31% | n/a | n/a | n/a: data not available

Overall transformation and regeneration frequency is given as the percentage of GFP-positive plants regenerated from the inoculated embryos. These results demonstrate that various methods and devices of the present invention are useful for providing multiple monocot embryos suitable for genetic transformation or tissue culture.

Example 15

Development of Liquid Media for Excising Corn Embryos

The fluid jet apparatus required about 20 L of liquid for excising embryos from one ear, necessitating the development of an excision medium that is simple to prepare (i.e., contains only about one or two ingredients), can be easily prepared, is filter sterilizable preferably through an in line filtration unit, can flow through the fluid jet apparatus at a preferred operating pressure of 40-60 psi, and does not require adjustment in pH prior to use. Such media and its preparation would lower cost, reduce media preparation time, and allow automation. This example provides several such media.

Culture media such as Lynx 1013 (inoculation medium) and Lynx 1902 (half strength Lynx 1013) were successfully used for excising corn embryos useful for transformation using a fluid jet apparatus. The Lynx 1013 comprises (per liter): MS Basal Salts (Phytotech; PhytoTechnology Laboratories, Shawnee Mission, Kans.): 2.165 g; MS Vitamins (100X; Phytotech): 10 ml; Glucose (Phytotech): 36 g; Sucrose (Phytotech): 68.5 g; Proline (Fisher): 0.115 g. The medium was adjusted to pH 5.4 with KOH then filter sterilized. Although these media worked well, they contained a number of ingredients, some of which must be filter sterilized. These media also require pH adjustment prior to use.

Several other liquid media (Table 4) were tested for excising transformable corn embryos from corn ears. Excised embryos were then used for transformation according to methods described elsewhere in the description, and the transformation frequency (TF) was determined for each tested excision medium. TF was defined as the number of unique transformation events regenerated into plants divided by the number of embryos inoculated with *Agrobacterium*.

All media tested, including water, were able to produce corn embryos that were transformable (see Table 4). However, media comprising mannitol produced comparable TF to control medium Lynx 1902. The mannitol medium is a simple medium with only two ingredients (mannitol and water), does not require pH adjustment prior to use, and is filter sterilizable, making it significantly more cost effective and convenient to use.

The mannitol concentration in the medium is from about 0.05 M to about 0.5M. Preferably, the mannitol concentration in the medium is about 0.1 M. Most preferably, the mannitol concentration in the medium is about 0.2 M. A suitable concentration of mannitol for the excision medium, however, can be determined by those skilled in the art of plant tissue culture, by simply varying the mannitol concentration.

Representative osmotic potential measurements of selected media are found in Table 4. Readings were taken using Wecor 5100C Vapor Pressure Osmometer (Wecor, Logan, Utah, USA), with calibration using standard solutions of 100, 290, and 1000 mOsm/kg. A medium with an osmotic potential (i.e. molality) from about 0 mOsm/kg to about 500 mOsm/kg is suitable for excising corn embryos for tissue culture, including for instance about 7 mOsm/kg to about 300 mOsm/kg. For instance, a 0.2 M solution of mannitol in water has an osmolality of about 222-230 mOsm/kg, while a solution of 0.05% MES in water has an osmolality of about 7 mOsm/kg. This range of osmotic potential is preferably obtained by adding one or two compounds to make the medium, such as Lynx media #1937, #1932, and #1162. Preferably, such compounds have no significant adverse effect on tissue culturability and transformability of the excised embryos.

TABLE 4

Osmotic potential measurements of exemplary solutions for use in isolating embryos.

| Identifier and composition | Mean Osmolality mOsm/kg | STD Osmolality | % TF |
|---|---|---|---|
| Lynx #1118 - Sterile distilled water | 7.00 | 8.89 | 3.0 |
| Lynx #1013 - Inoculation Medium | 503.67 | 9.07 | 20.6 |
| Calcium chloride - 10 ppm $CaCl_2$ | n/a | n/a | 4.2 |
| Lynx #1902 - Half Strength Lynx #1013 | 262.67 | 4.04 | 9.5 |
| Lynx #1932 - 0.2M Mannitol, autoclaved | 222.33 | 9.29 | 15.6 |
| Lynx #1986 - 0.2M Mannitol, filter sterilized | 230.00 | 28.83 | 11 |
| Lynx #1987 - 0.1M Mannitol, filter sterilized | 117.33 | 27.15 | 9.7 |
| Lynx #1162 - 5% Sucrose (w/v) | 258.33 | 4.51 | 4.5 |

TABLE 4-continued

Osmotic potential measurements of exemplary solutions for use in isolating embryos.

| Identifier and composition | Mean Osmolality mOsm/kg | STD Osmolality | % TF |
|---|---|---|---|
| Lynx #1953 - 5% Sucrose + MS Salts (same amount as in Lynx #1013) | 313.33 | 3.51 | 1.6 |
| Lynx #1937 - 0.05% MES, pH 5.4, autoclaved | 7.00 | 3.61 | 0.3 |
| Lynx #1964 - 0.05% MES, pH 5.8, filter sterilized with 0.2 micron filter | 13.33 | 11.50 | 0 | n/a = not done

Example 16

Construction of a Media Preparation System for Fluid Jet Excision

This example describes a media preparation system (MPS) for use with a fluid jet apparatus. The fluid jet apparatuses tested required about 20 liters of medium, which requires time and effort to make and use. The MPS of the present invention can prepare large amount of media quickly. It also allows for the preparation of a specified volume of media for a particular size corn ear.

Figure 11:
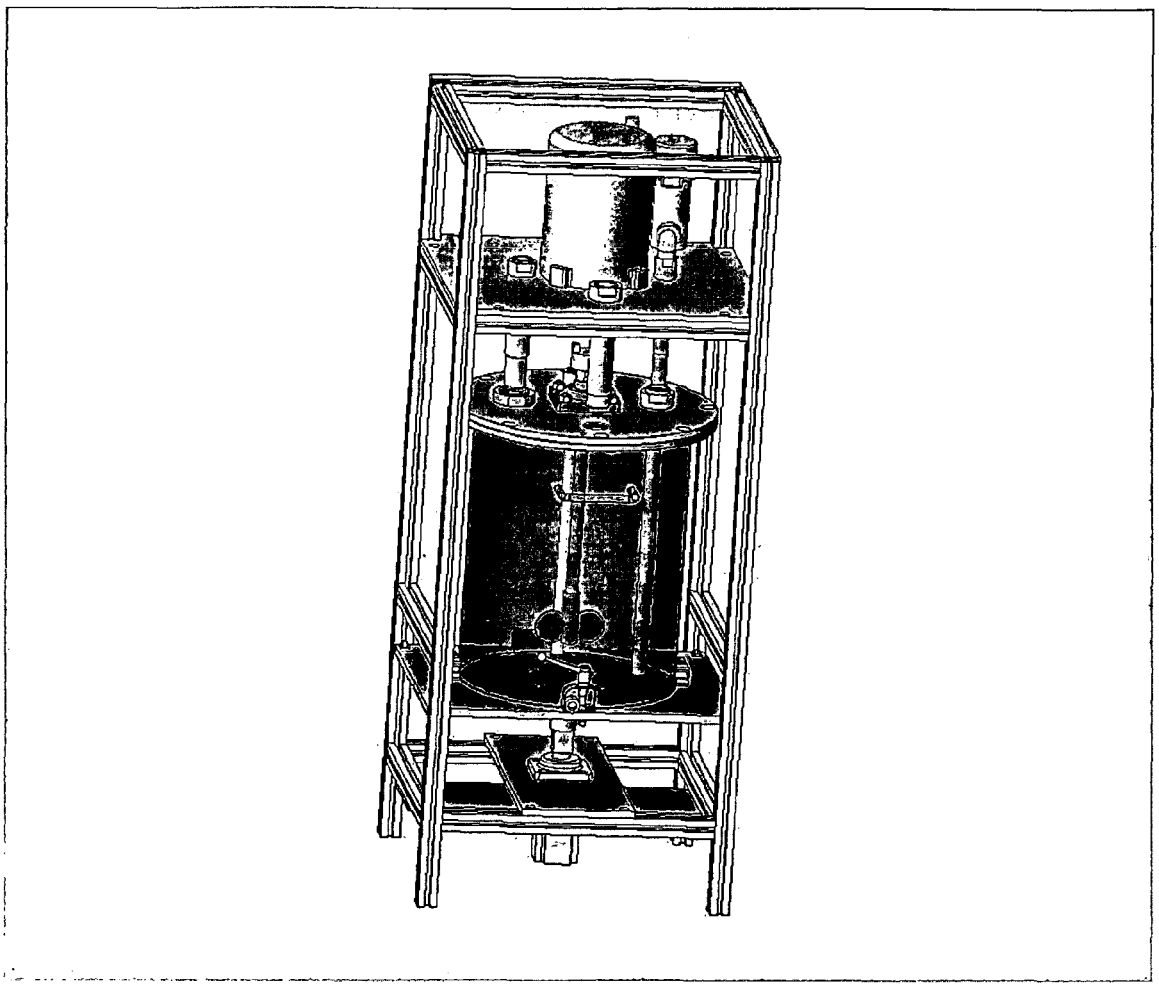
FIG. 11 illustrates an embodiment of a Media Preparation System provided by the invention.
Figure 12:
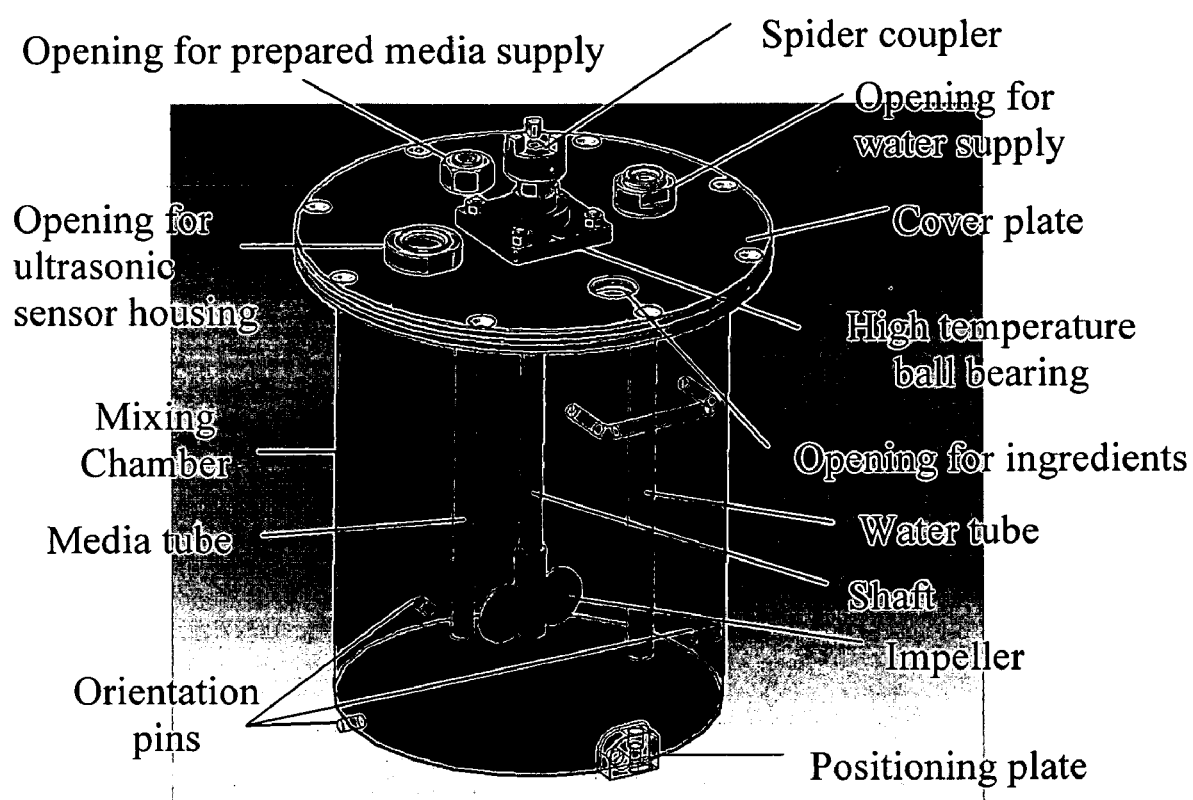
FIG. 12 illustrates a general view of the mixing chamber of the Media Preparation System provided by the invention.
Figure 13:
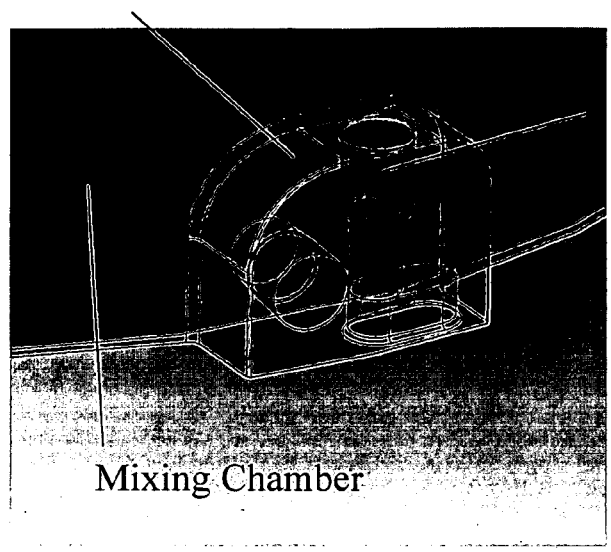
FIG. 13 illustrates a close up view of the mixing chamber, lower end, with positioning plate and quick connect mounting.
Figure 14:
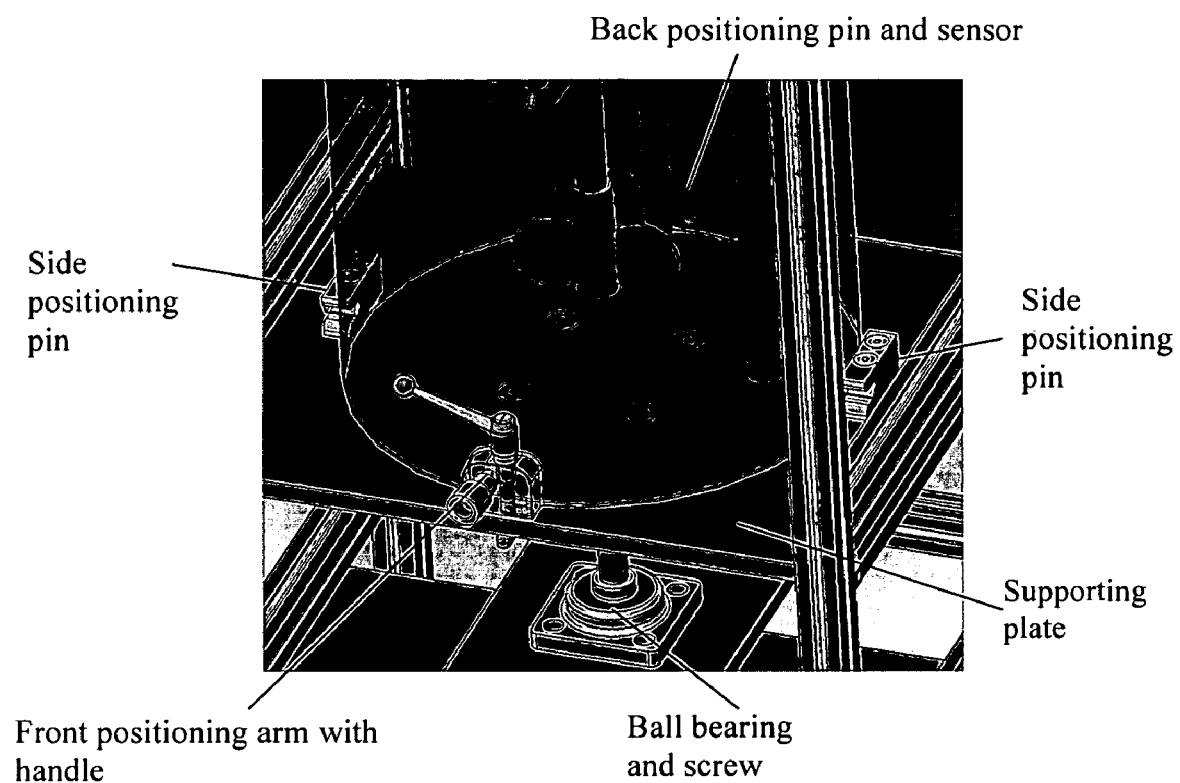
FIG. 14 depicts a close up of the lower end of the mixing chamber, with positioning device and supporting plate.

The MPS comprised a Mixing Chamber (MC) and an MPS Housing (MPSH). The MC is designed to be easily disengageable from the MPSH for easy sterilization by autoclaving. Both the MC and MPSH can be made of any suitable material. Preferably, they are made of a material such as steel or aluminum. As shown in FIGS. 11 and 12, the MC comprises a tank having an upper end and a lower end, a flange that is attached to the upper end of the tank, and a cover plate for covering the upper end and for sealing the mixing chamber. Preferably the tank is sealed with the cover plate by an o-ring provided in the flange. The cover plate is preferably made of 7075 aircraft grade, corrosion resistant aluminum to reduce weight of the mixing chamber. In one embodiment, the tank is provided with three pins at the lower end, each on three sides as shown in FIG. 12, for orienting and positioning the tank on the mixing chamber supporting plate. In a working position, the three pins engage with the three positioning brackets provided on the supporting plate as shown in FIGS. 12 and 14. A positioning plate (FIG. 12, 13) is also provided at the bottom of the tank, at the forth side, for holding the tank in a working position on the mixing chamber supporting plate. Preferably, the positioning plate has a ¼"NPT thread for mounting a quick connector for carrying a position arm with a handle (FIG. 14) in order to fix the mixing chamber on the supporting plate (e.g. FIG. 13).

The cover plate is provided with an opening for inserting a tube for bringing in a liquid such as water for making medium, an opening for inserting a tube for taking out the prepared medium which is connectable a fluid jet apparatus, an opening for inserting a tube for adding medium ingredients, preferably of stainless steel, into the mixing chamber (e.g. FIG. 12). In the working position, separate o-rings seal various tubes with openings. The cover plate is also provided with an opening for inserting a housing containing an ultrasonic sensor for sensing a specified volume of medium that need to be prepared. Preferably, the opening for the ultrasonic sensor housing is provided on one side of the cover plate. In the working position, various openings provided on the cover plate of the mixing chamber are connected to the corresponding tubes provided at the lower surface of the upper platform of the housing (FIG. 11). These tubes are preferably made of steel. The various openings connect to the mixing chamber as shown in FIG. 11, for instance via connecting tubing. The tubing is preferably made of polycarbonate.

Figure 16:
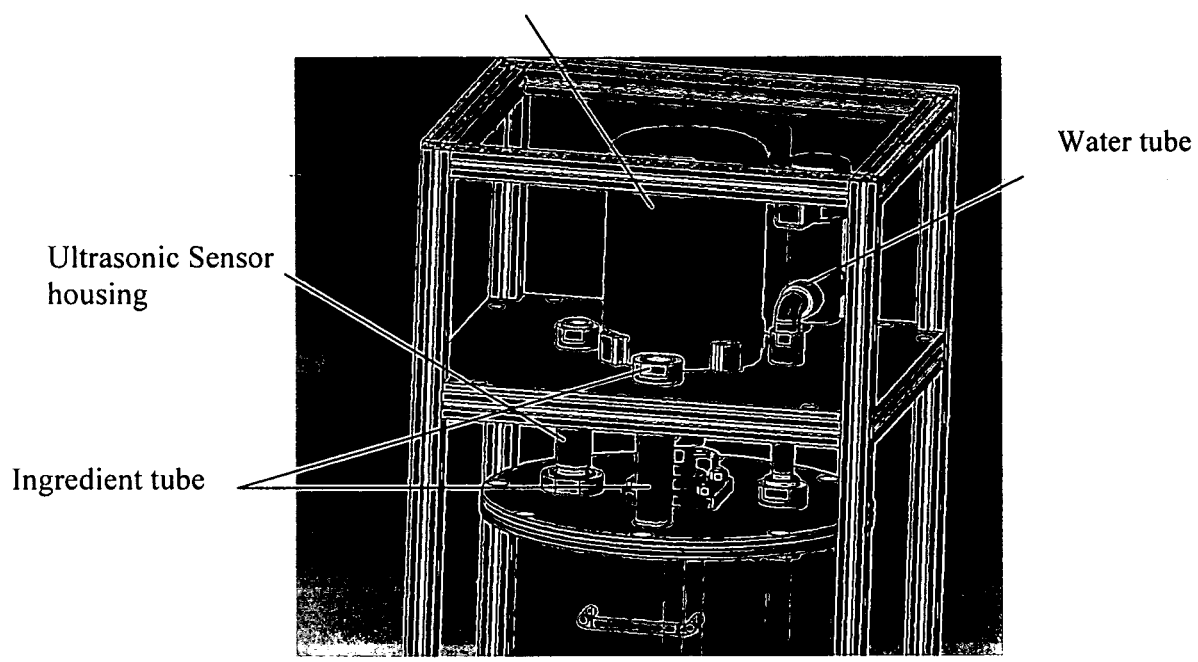
FIG. 16 depicts a close up of the upper portion of the Media Preparation System in work position.

A media mixer assembly is attached to the lower end of the cover plate such that the assembly hangs, preferably in the centre of the tank. The assembly comprises a two blade folding impeller, a stainless steel shaft sealed by an o-ring in the cover plate, a high temperature ball bearing suitable for functioning at a high temperature, such as above 400° F., present during autoclaving and a spider coupler (e.g. FIG. 12) for coupling the assembly with a motor in the MPSH (FIG. 16).

Figure 15:
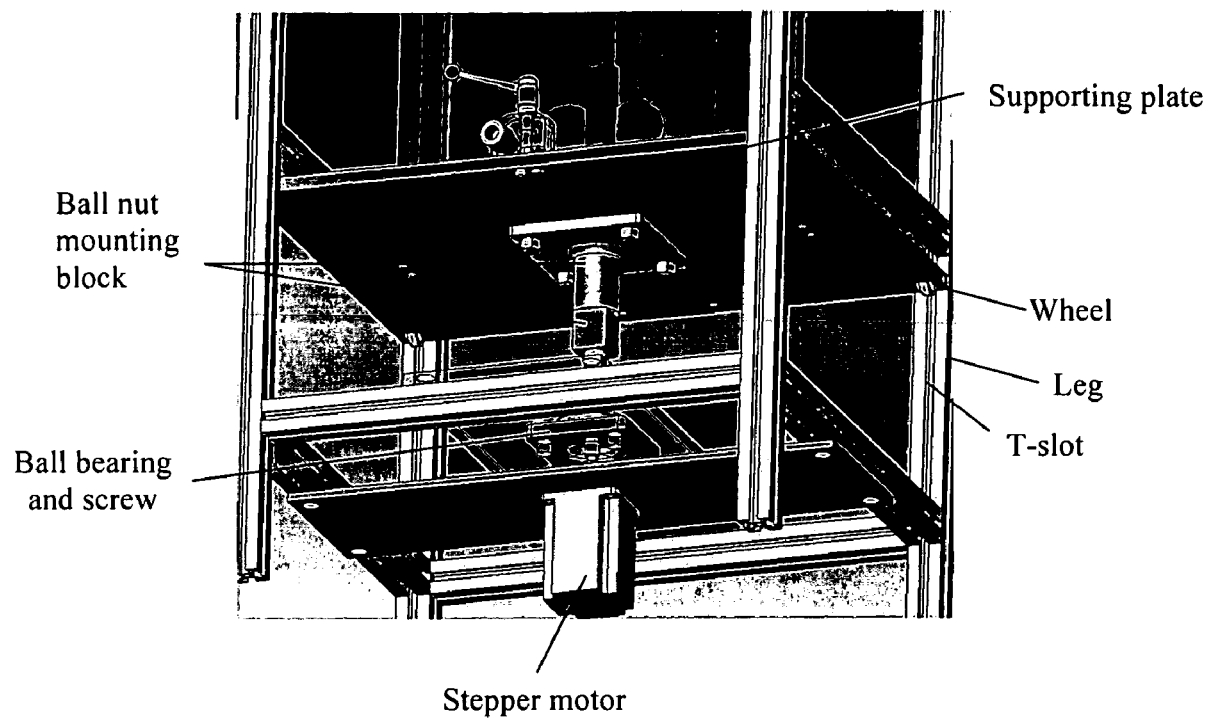
FIG. 15 depicts a close up of the lower portion of the Media Preparation System in work position.

A ball nut-mounting block is mounted on the lower side of the mixing chamber supporting plate and is connectable to a ball screw mounted in a ball bearing provided at the upper surface of the lower platform of the housing. The support plate is also slidably connected via four wheels to four legs of the MPS housing as shown in FIG. 15. The wheels roll along in t-slots of the four legs to facilitate up and down movement of the mixing chamber when the stepper motor provided at the lower surface of the lower platform of the MPSH is turned on.

After autoclaving, the mixing chamber is positioned on the supporting plate by the three pins and the positioning plate. The positioning arm with the handle is inserted in the quick connector. The arm is pushed down and turned 90 degrees clockwise with the help of the handle for positioning and fixing the mixing chamber on the supporting plate. The positioning arm is attached to a cam and mounted on a spring that is welded to the supporting plate. The spring pushes the arm and the cam up. When placed in position, the back pin of the mixing chamber pushes an electrical switch, which sends a signal to a Programmable Logic Controller (PLC). This signal informs the PLC that the mixing chamber is positioned on the mixing chamber supporting plate. The stepper motor provided on the lower platform of the housing then pushes the mixing chamber towards the upper platform of the housing where, in a working position, various openings provided on the cover plate of the mixing chamber become connected to the corresponding tubes provided at the lower surface of the upper platform of the housing (FIG. 16).

Upon receiving an operator signal, the PLC opens an electromagnetic valve connected to a water system for filling the mixing chamber with water. The ultrasonic sensor monitors the water level in the mixing chamber. When the level of water reaches the specified level in the mixing chamber, the PLC closes the water electromagnetic valve and waits for a signal from the operator indicating that the components of the excision medium are in the mixing chamber. When the PLC receives that signal, it actuates a motor provided on the upper surface of the upper platform of the MPSH and operably linked to the mixer assembly. Thus, the mixer assembly starts mixing the medium. Once the medium is ready, it is pumped using a gear pump through a medium outlet tube to the fluid jet apparatus according to a PLC program.

In one embodiment, the prepared medium outlet/supply connected to the fluid jet apparatus is provided with an inline filtration unit such as a 0.2 Micron Absolute FiberFlo® Hollow Fiber Capsule Filter (Minntech Filtration Technologies Group, Minneapolis, Minn.) for sterilizing the medium before its use in the fluid jet apparatus for excising embryos.

Example 17

Embryo Isolation by Phased Excision

This example describes an apparatus for preparing multiple corn embryos suitable for tissue culture from kernels on a corn ear, comprising at least one aperture for guiding a first fluid stream at a first time point for substantially extracting endosperms from the kernels, and a second fluid stream at a second time point for substantially extracting embryos from the kernels, the extracted embryos being suitable for tissue culture. The apparatus further comprises a means for moving at least one corn ear relative to the first and the second fluid streams. The means for moving at least one corn ear relative to the first and the second fluid streams rotates at least one corn ear and the at least one aperture relative to each other. The means for moving at least one corn ear relative to the first and the second fluid streams moves the fluid streams along the longitudinal axis of at least one corn ear. In this particular embodiment of the apparatus, each fluid stream is a liquid stream. The liquid stream may consist, for instance, essentially of mannitol and water at a concentration of about 0.05 M to about 0.5 M mannitol. The fluid stream can alternatively be a gas stream. The apparatus may further comprise a means for detecting excised endosperms or embryos. The apparatus may also further comprise a means for channeling excised endosperms or embryos so as to separate endosperm from embryo. The apparatus further comprising a means for linking the means for detecting excised endosperms and embryos to the means for channeling excised endosperms or embryos electronically, for automation. The apparatus can further comprise at least one separator for separating embryos from non-embryo tissues, wherein the separated embryos comprise corn embryos suitable for tissue culture. The separator can comprise a size-exclusion device. Alternatively, the separator can separate the embryos from the non-embryo tissues by differential hydrophobicity or by density differential.

The present example also describes a method of providing monocot embryos suitable for tissue culture comprising: (a) providing monocot seeds containing embryos having an opening in the pericarp of the seeds; and (b) applying a first force at a first time point to the seeds for substantially extracting endosperms from the seeds and a second force at a second time point for substantially extracting embryos from the seeds, the extracted embryos being suitable for tissue culture. The forces comprise one or more forces selected from fluid jet positive pressure, liquid jet positive pressure, mechanical positive pressure, negative pressure, centrifugal force, linear acceleration, linear deceleration, fluid shear, fluid turbulent flow, and fluid laminar flow. The method further comprises separating embryos from non-embryo tissue by the methods selected from the group consisting of size-exclusion, hydrophobic separation, and density differential separation. The monocot seeds are provided on at least one ear. The monocot may be in the family Poaceae, such as a *Zea* species (e.g. *Zea mays*). The step of tissue culture may include one or more steps of transformation and regeneration, resulting in at least one fertile transformed plant.

Figure 17:
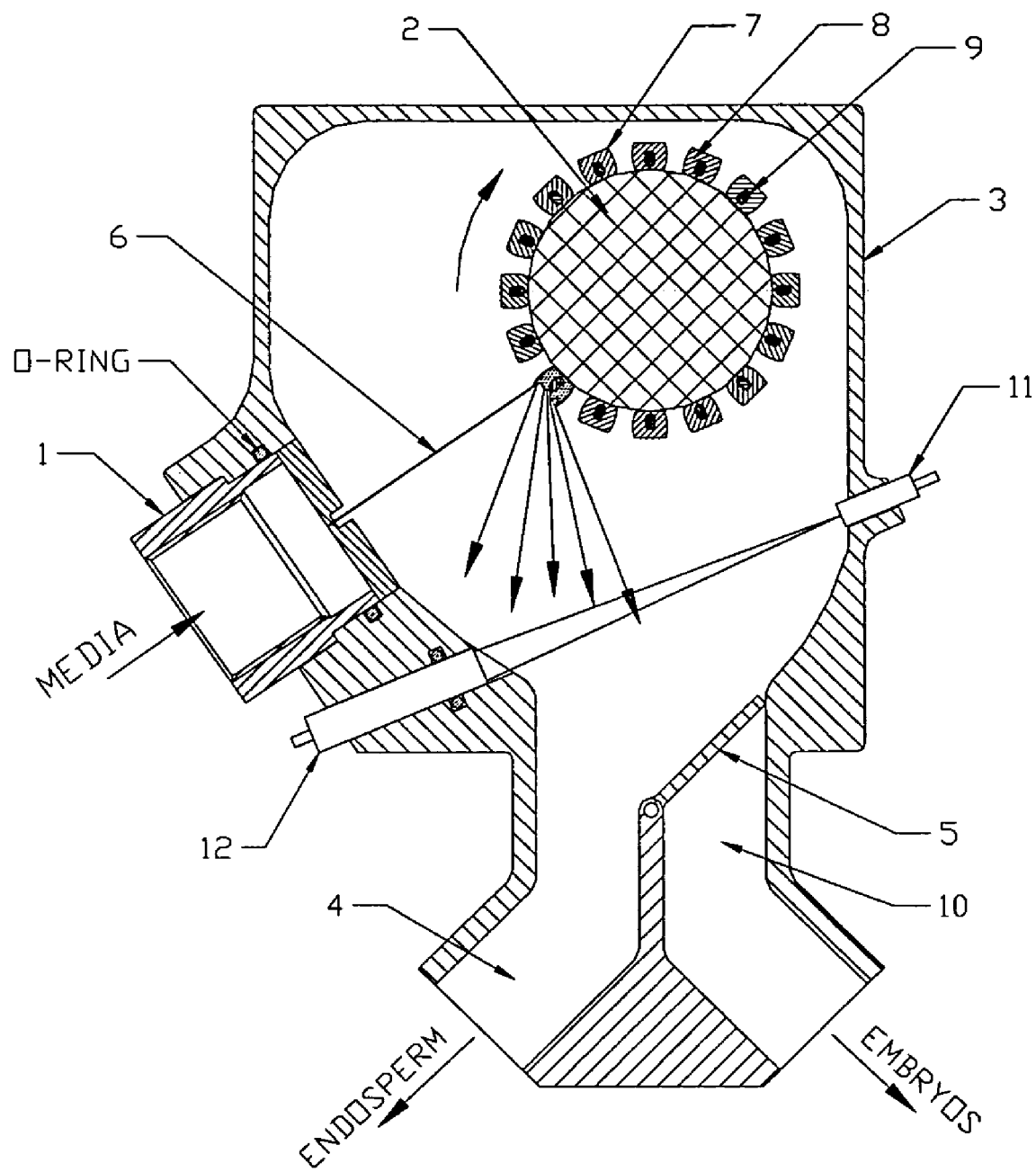
FIG. 17 comprises a cross sectional view of an apparatus for phased separation of corn embryos.

As shown in FIG. 17, the apparatus is provided with a flat jet nozzle (1) for producing a flat laminar flow (6), two stepper motors controlled by a programmable logic controller (PLC), and a digital gear pump. One stepper motor rotates the ear (2), having corn kernels from which crown have been removed to facilitate excision, mounted on a shaft in a hermetic chamber (3) and the second motor advances the ear along the axis such that the flow acts on each kernel for substantially the same amount of time. The digital gear pump forces the liquid medium through the nozzle as specified by the PLC rate and pressure. The nozzle (1) produces a flow of liquid that is about 0.003" wide and about 1" high. Generally, the width of the flow is less than the width of the kernel. In the tested pressure range 30-75 PSI, the laminar flow was stable at a distance up to 2.5-3" from the nozzle (1) and did not fall apart before reaching the ear. The ear (2) may be positioned 1¾"-2" away from the nozzle (1) so that the flow of liquid acts on each kernel in a row with substantially the same force. The amount and duration of force can be manipulated by altering the pressure of liquid in the nozzle, by adjusting the distance of the ear to the nozzle, and the space between the nozzle plates as well as other parameters such as the entry angle of the flow of liquid into the kernel, and the speed of ear rotation.

In the first phase, a PLC according to a PLC program opens a channel (4) by valve (5) for endosperm collection, and sets a pressure and flow rate through the nozzle (1) by sending control signals to the digital gear pump, and rotates and advances the ear (2) by the two stepper motors. The flow of liquid (6) controlled by the PLC first washes out the kernel's (7) endosperm (8) leaving embryos (9) attached to the kernels (7). The amount of time and force necessary to wash out the endosperm may be adjusted depending upon the endosperm size, extent of cut in the crown of the kernel, and differences between ear and kernel sizes, among other parameters. The mixture of liquid medium and endosperms collected in channel (4) can be pumped through a filtration system. After filtration, the liquid medium can be reused in the excision process.

In the second phase, the PLC according to the PLC program closes channel (4) and opens a channel (10) by valve (5) for embryo collection, setting a pressure and flow rate through the nozzle (1), and rotating and advancing the ear. The flow of the liquid (6) washes out embryos (9) and the rest of endosperms (8) out of the kernels (7). Further separation of embryos, if desired, can be done using separators described elsewhere. The amount of time and force necessary to wash out the embryo can be adjusted depending upon the embryo size, extent of cut in the crown of the kernel, and differences between ear and kernel sizes, among other parameters. The mixture of liquid medium and embryos collected in channel (10) is subjected to a separation device (e.g. Example 18) to isolate embryos from debris and liquid, and the liquid can be pumped through a filtration system for reuse in the excision process.

The chamber (3) may optionally be provided with an emitter (11) and through beam sensor (12) for detecting the embryos in exiting liquid medium after excision. During the first phase, the signal confirming appearance of embryos in the exiting media instructs the PLC for completing phase one. During the second phase, the signal confirming disappearance of embryos in the exiting liquid medium alerts the PLC for completing phase two, and may further instruct the PLC to shut down the apparatus.

Corn embryos excised using this apparatus and method were transformed using standard methods known in the art of corn transformation. (e.g. Cai et al; U.S. Patent Application Publication 2004/0244075). All treatments used Lynx # 1986 (0.2M Mannitol, un-sterilized), for excising embryos. Representative transformation frequencies (TF) are shown in Table 5, indicating that embryos produced by this apparatus and method were transformable and yielded transgenic plants.

TABLE 5

Transformation of corn embryos excised by the phased fluid jet apparatus and method.

| Exp. # | Trt # | Experiment Description | TF % |
|---|---|---|---|
| 6778 | 2 | FJ Phase w/ endosperm | 6.0% |
| 6778 | 3 | FJ Phase w/o endosperm | 8.0% |
| 6858 | 2 | FJ Phase w/ endosperm | 4.0% |
| 6858 | 3 | FJ Phase w/o endosperm | 8.0% |

TABLE 5-continued

Transformation of corn embryos excised by the phased fluid jet apparatus and method.

| Exp. # | Trt # | Experiment Description | TF % |
|---|---|---|---|
| 6858 | 5 | FJ Phase w/ endosperm | 2.9% |
| 6858 | 6 | FJ Phase w/o endosperm | 5.7% |
| 6894 | 2 | FJ Phase w/ endosperm | 14.0% |
| 6894 | 3 | FJ Phase w/o endosperm | 16.0% |
| 6894 | 5 | FJ Phase w/ endosperm | 6.7% |
| 6894 | 6 | FJ Phase w/o endosperm | 6.7% |

"FJ (Fluid Jet) Phase w/ endosperm" refers to embryos that, after collection, were inoculated with endosperm and left on the same plate (embryos and endosperm together).
"FJ Phase w/o endosperm" refers to embryos that, after collection, were moved to a fresh plate of media leaving the endosperm behind.

Example 18

Embryo Separation Process

This example describes a flotation process for separating embryos from a mixture produced by a fluid jet excision process. Parameters for efficient separation are described herein. In this process, bubbles of a gas were generated in a fluid and attached to excised corn embryos present in the fluid. The bubbles floated to the surface (i.e. fluid-air interface), allowing the embryos to be preferentially collected while leaving behind endosperm material and other debris.

Figure 18:
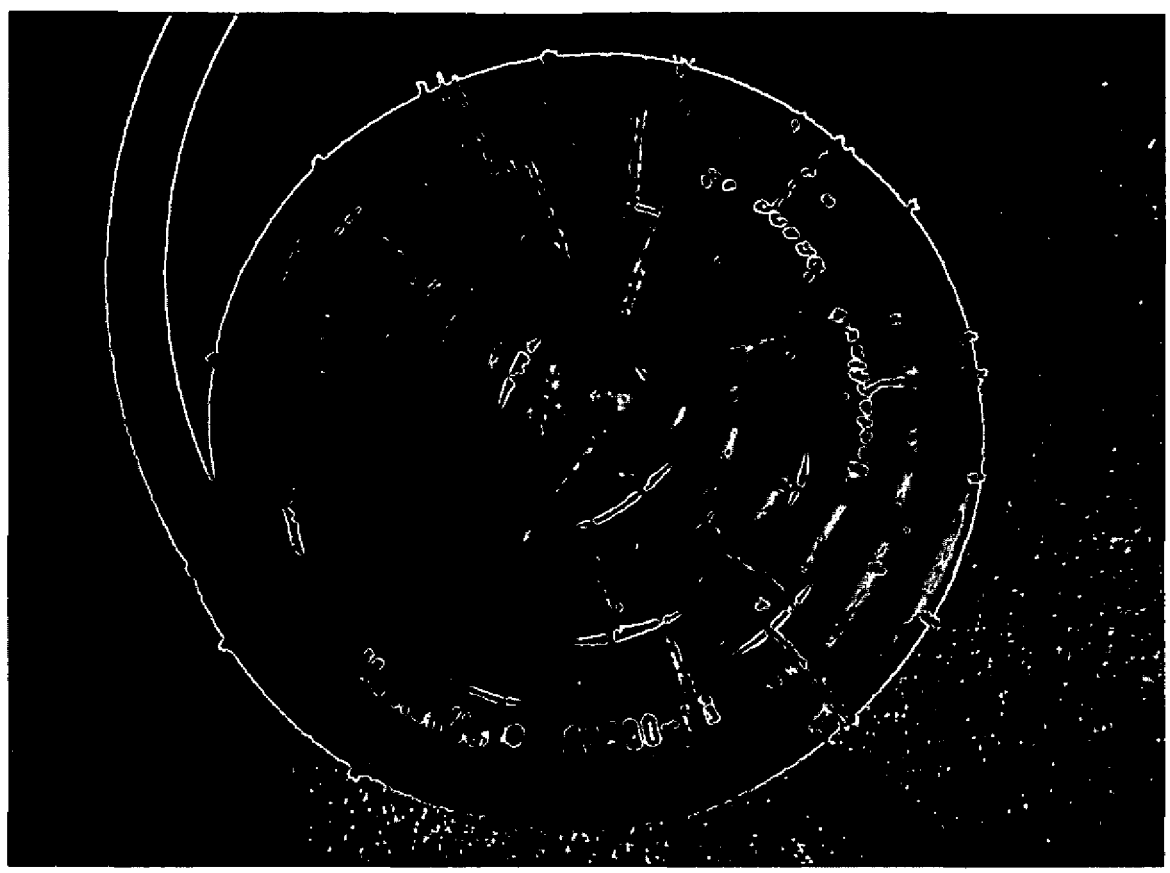
FIG. 18 illustrates a spiral shaped limewood bubble dispersion device.
Figure 19:
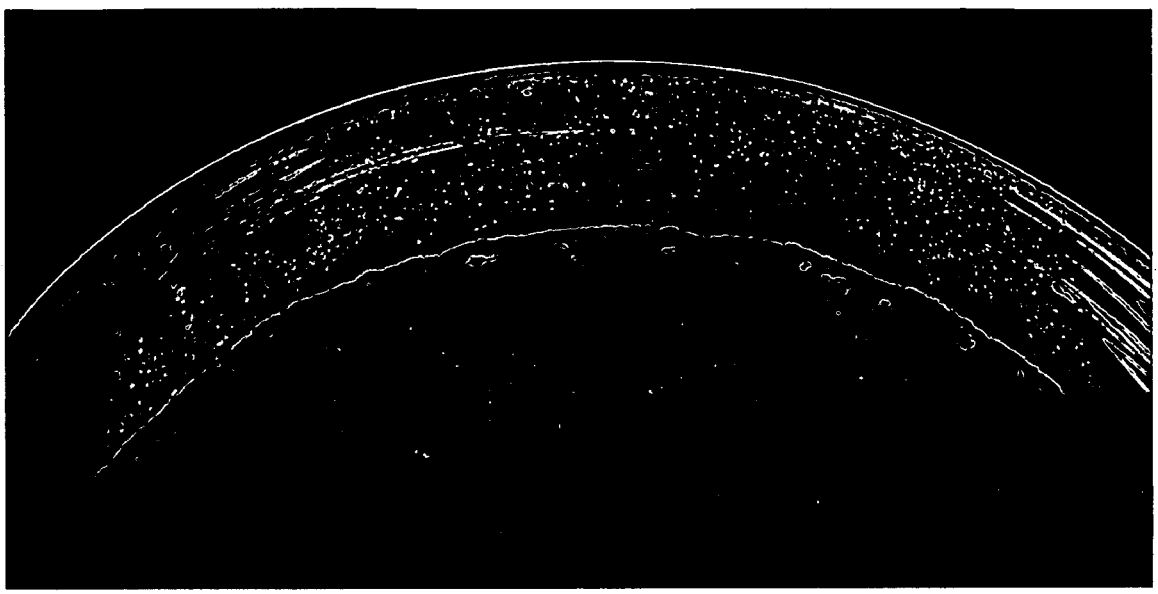
FIG. 19 illustrates embryos floating on top of froth produced by a spiral shaped limewood bubble dispersion device.
Figure 20:
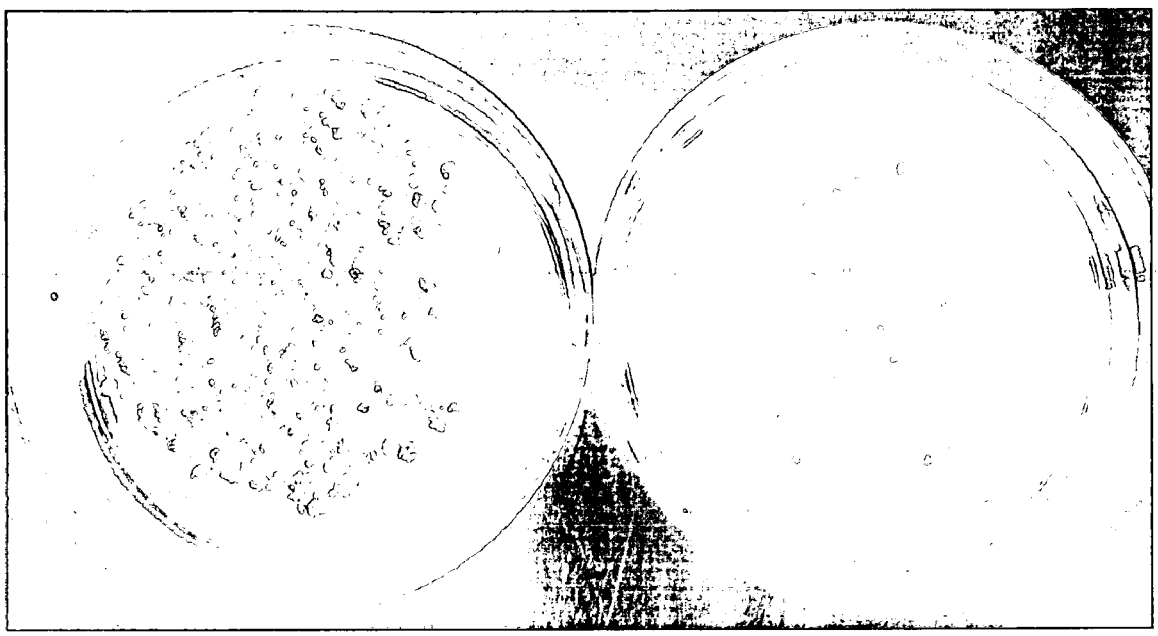
FIG. 20 illustrates separation of embryos from endosperms by use of a floatation process.

To reduce the number of bubbles per unit volume and generate a more uniform field of bubbles so that less shear force was generated, a device was constructed containing multiple point sources of bubbles. The device was constructed by inserting individual splinters of limewood into pre-punched holes in a length of silicone tubing (Masterflex® silicone tubing C-96400-16, Cole-Parmer). After inserting the limewood slivers into silicone tubing, one end of the tubing is plugged with a stainless steel bearing. The tubing is then coiled in a spiral and secured with a metal wire as shown in FIG. 18. The spiral-shaped limewood air dispersion device combined with using PEG as the surfactant has shown 95% embryo purification from nearly all of the endosperm as shown in FIG. 19. FIG. 20 illustrates the amount of endosperm separated from the embryo fraction by bubble flotation using the spiral shaped limewood air dispersion device and PEG. Other limewood-based bubblers may be constructed or purchased from, for instance, aquarium suppliers. The Petri plate on the left in FIG. 20 shows the large amount of endosperms intermixed with embryos when the flotation process was not used. In comparison, the Petri plate on the right shows the reduction in the amount of endosperm co-fractionating with the embryos when the floatation process of the present invention was used. Bubbles can also be produced by ceramic materials having various pore sizes.

Figure 21:
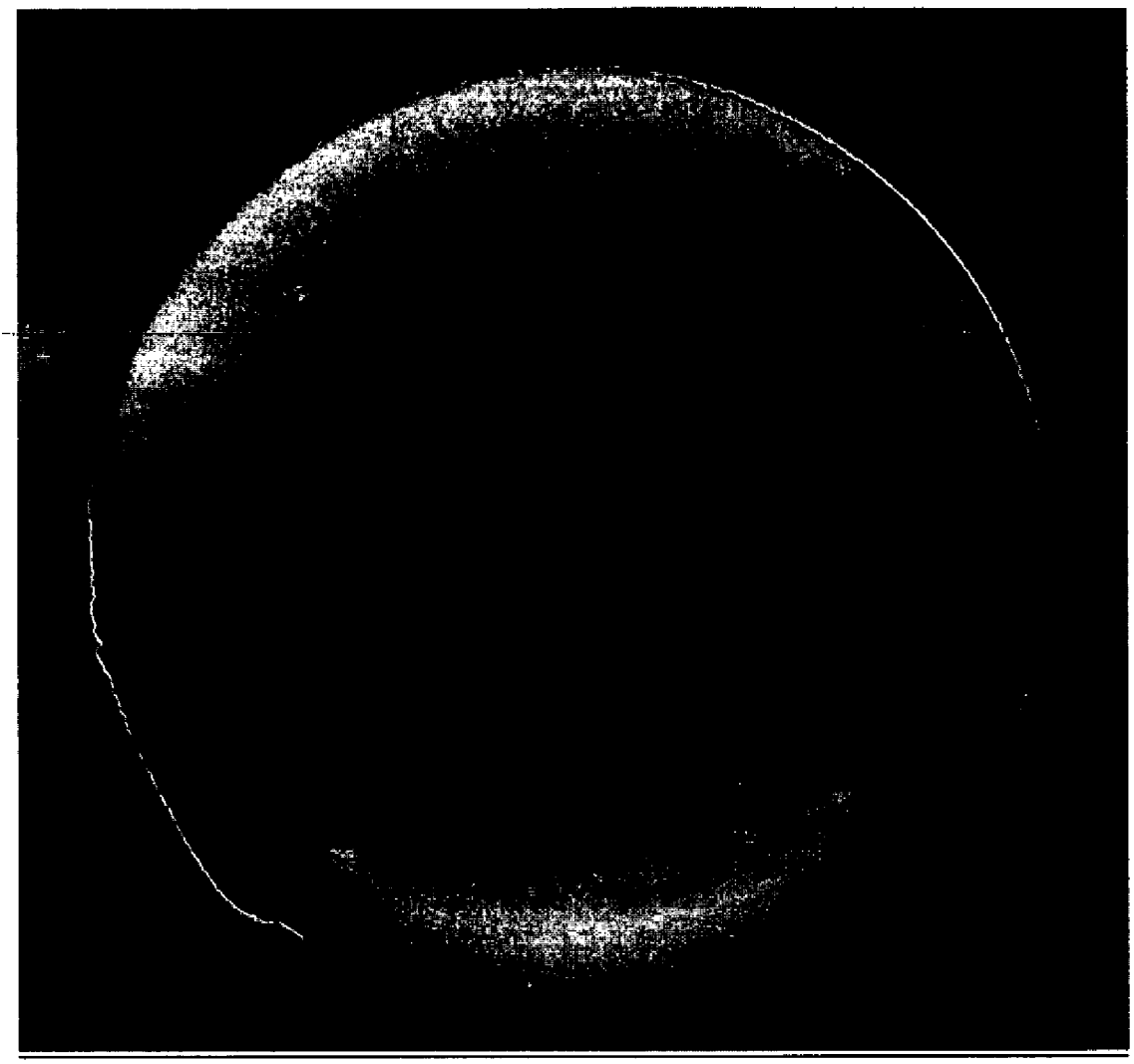
FIG. 21 depicts a vacuum filter device used to harvest embryos from the froth at the surface of an air-fluid interface of an embryo separator.

In order to detach bubbles from the source material generating them, it is desirable that the source material be of an opposite nature to the bubbles, with respect to the degree of polarity (i.e. hydrophobicity). Since the air bubbles are covalent in nature, they will tend to detach readily from a material that is polar in nature. Conversely, bubbles emerging from a surface which is also covalent in nature, like a porous plastic sparger, will tend to adhere to the surface, and coalesce and grow to a larger size before detaching. In this respect, the Chemglass sparger, limewood, and ceramic are all desirable choices. The surface of limewood is composed of cellulose, hemicellulose and lignin which are polar and thus hydrophilic, as are the sintered glass sparger and ceramic materials In one instance, once embryos were carried to the surface by the bubbles and deposited in the froth, they were harvested by skimming off the froth and then rinsed free of the froth. In another experiment, a vacuum filter device (e.g. FIG. 21) was used to harvest embryos off the surface of the froth.

In one experiment, embryos and endosperm were excised from donor ears using the fluid jet (FJ) apparatus and collected on cheesecloth (CC). The mixture of embryos and endosperm was then placed in a graduated cylinder filled with Lynx 1013 and 20 µl of 20% PPG (polypropylene glycol mono-butyl ether—Av. Mol. Wt. 340; Aldrich Cat. No. 438103; Sigma Chemical Co., St. Louis, Mo.), and bubbles were produced by air pumped through a fritted fine pore glass dispersion tube (Chemglass) by an aquarium pump (bubbler). Separated embryos, substantially free of endosperm material and other debris, were collected as outlined above. Separated embryos were used for *Agrobacterium*-mediated transformation of corn by using standard methods known in the art of corn transformation as noted above. Transformation frequencies are shown in Table 6.

TABLE 6

Transformation of corn embryos separated by flotation using air bubbles stabilized by PPG.

| Exp. # | Trt # | Experiment Description | # embryos inoculated | # GFP+ | # Events to Soil | TF % |
|---|---|---|---|---|---|---|
| 6376 | 2 | FJ Bubbler CC | 120 | 32 | 9 | 7.5% |
| 6396 | 2 | FJ Bubbler CC | 223 | 32 | 10 | 4.5% |
| 6419 | 2 | FJ Bubbler CC | 201 | 87 | 17 | 8.5% |

In another experiment, a limewood-based bubbler was used to separate embryos from endosperms excised by the fluid jet apparatus. In general the limewood-based bubbler was placed in a beaker in a sterile laminar flow hood. The tubing of the bubbler was connected to an air filter at one end. The other end of the air filter was connected to the aquarium pump. The separation medium (0.2M Mannitol with 20 µl of 20% PEG (Avg. Mol Wt. 8000, Sigma No. P21390)) was then added to the beaker over the bubbler. The embryo and endosperm from the fluid jet apparatus were collected and transferred to the beaker. The air was bubbled through the bubbler. Floating embryos were transferred to a small Petri dish and used for transformation using standard methods known in the art of corn transformation as noted above. Transformation frequencies are shown in Table 7.

TABLE 7

Transformation of corn embryos separated by flotation using air bubbles stabilized by PEG

| Experiment | # of embryo used | Mean TF (%) | SE (%) |
|---|---|---|---|
| Manual Excision | 1759 | 22.33 | 4.58 |
| Fluid Jet Excision w/o separation | 1700 | 34.85 | 5.62 |
| Fluid Jet Excision with Bubble Separation | 1648 | 35.50 | 5.70 |

Example 19

Apparatus for Separating Embryos by Flotation

Figure 22:
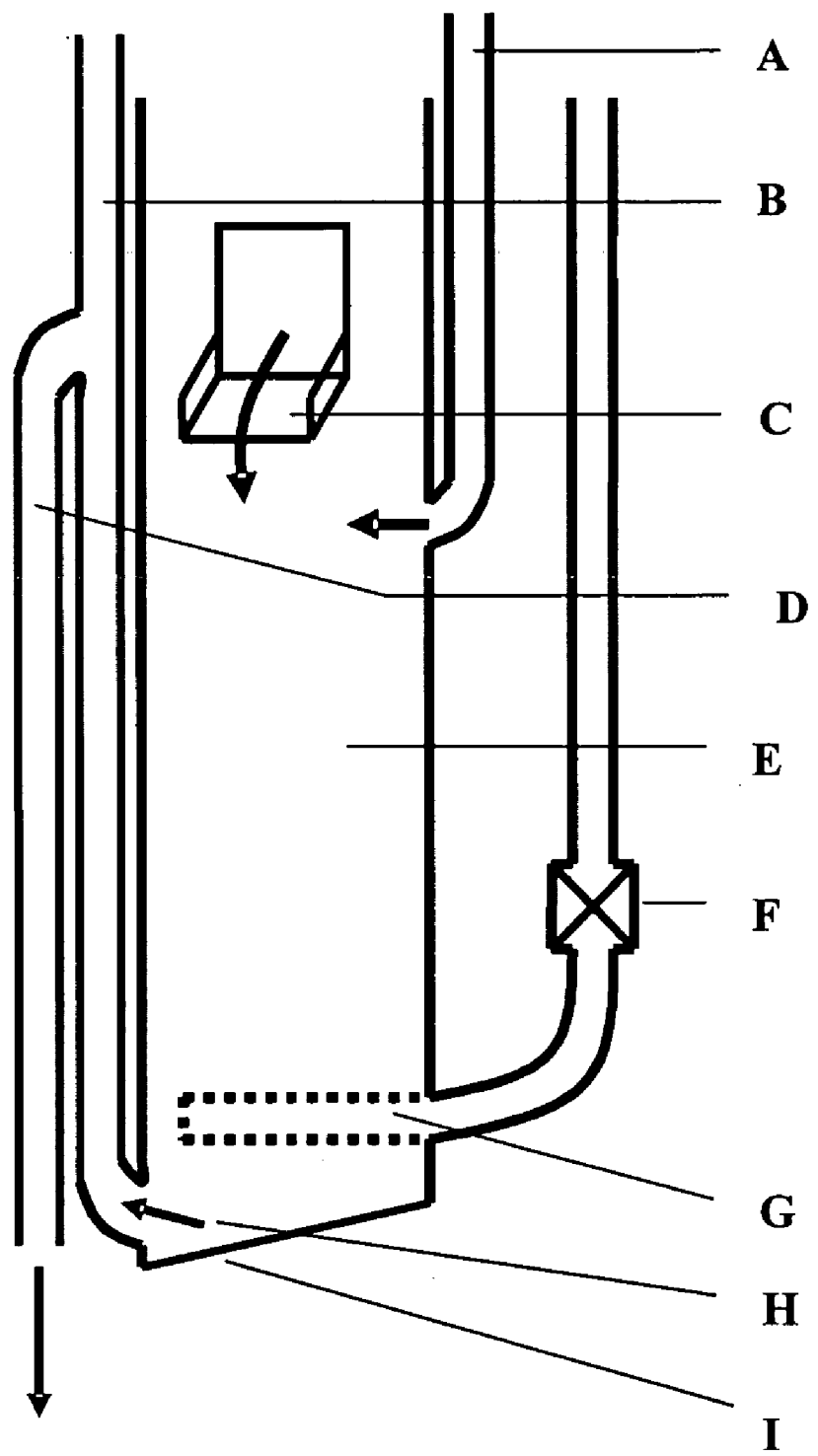
FIG. 22 comprises a schematic diagram of an embryo separation device as described in Example 19.

FIG. 22 shows an apparatus for separating embryos by flotation that comprises a floatation column (E) connected to an inlet tube (A) at the upper end of the column for adding a mixture of embryos, endosperm and other debris, an air dispersion tube (G) at the lower end of the column for producing air bubbles for raising the embryos, and an outlet tube (H) also at the lower end of the column for regulating the liquid level and for removing the debris from the bottom of the column. The bottom of the column is preferably slanted to facilitate removal of the debris that does not float. The floatation column is further provided with an overflow chute (C) for collecting the froth containing the embryos. The air dispersion tube is further provided with a valve (F) to prevent backflow of column liquid into the air dispersion tube.

To operate this apparatus, the flotation column is filled with a liquid medium compatible with subsequent transformation and tissue culturing of the embryos until the level of the liquid reaches the overflow drain (D). The overflow drain has an anti-siphoning tube (B) open to the air at the top. A surfactant is added to the liquid medium to prevent the premature coalescence of the bubbles and stabilize the froth for attaching and raising the embryos to the top of the flotation column.

The next step in operation of the apparatus is to turn on the air supply to the air dispersion tube. The pores in the dispersion tube are small enough to produce bubbles that rise slowly enough that their contact time with the embryo's hydrophobic surface is long enough to allow attachment of the bubbles to the embryos.

Next a mixture of embryos, endosperm, and debris produced by the fluid jet apparatus containing the desired concentration of a surfactant (such as PEG at a concentration of 20 parts per million) is fed into the inlet tube. As the slurry enters the flotation column the suspended particles encounter the column of bubbles from the air dispersion device. Bubbles first attach to the embryos and preferentially raise the embryos to the surface of the flotation column where they become part of the froth. As the froth accumulates it exits the flotation column through the chute (C).

During operation the column can be tilted at a slight angle from vertical toward the chute so that the rising bubbles are concentrated at the back wall of the column and tend to push the froth forward and out the chute. Alternatively, a cover which slants at an upward angle toward the chute can direct the froth to the chute.

The endosperm-rich debris which does not float falls to the bottom of the flotation column and accumulates at the low point of the slanted bottom. These debris are displaced out of the column during the automatic liquid leveling of the column that occurs when the slurry of embryos and endosperm debris is initially fed into the feed funnel at the beginning of column operation, or may be removed at the end of operation of the flotation column.

In another embodiment, the level of liquid in the flotation tank is kept level with an exit chute and the froth rising to the surface is continuously swept into the chute. This action can be facilitated by having more bubbles rising on the side of the tank away form the chute so that there is a circulation produced which rises on the side away form the chute and sinks on the side with the chute.

In another embodiment, the liquid level in the flotation tank can be kept below the level of the chute until a sufficient quantity of froth and embryos have accumulated and then the liquid level is raised so that the froth and embryos spill into the chute.

Example 20

Alternative Apparatus for Separating Embryos by Flotation

This example describes another embodiment of the apparatus designed to separate corn embryos from corn endosperm by means of a flotation process using bubbles and surfactants. The apparatus can be used with an embryo excision apparatus such as a fluid jet apparatus described elsewhere in the application.

Figure 23:
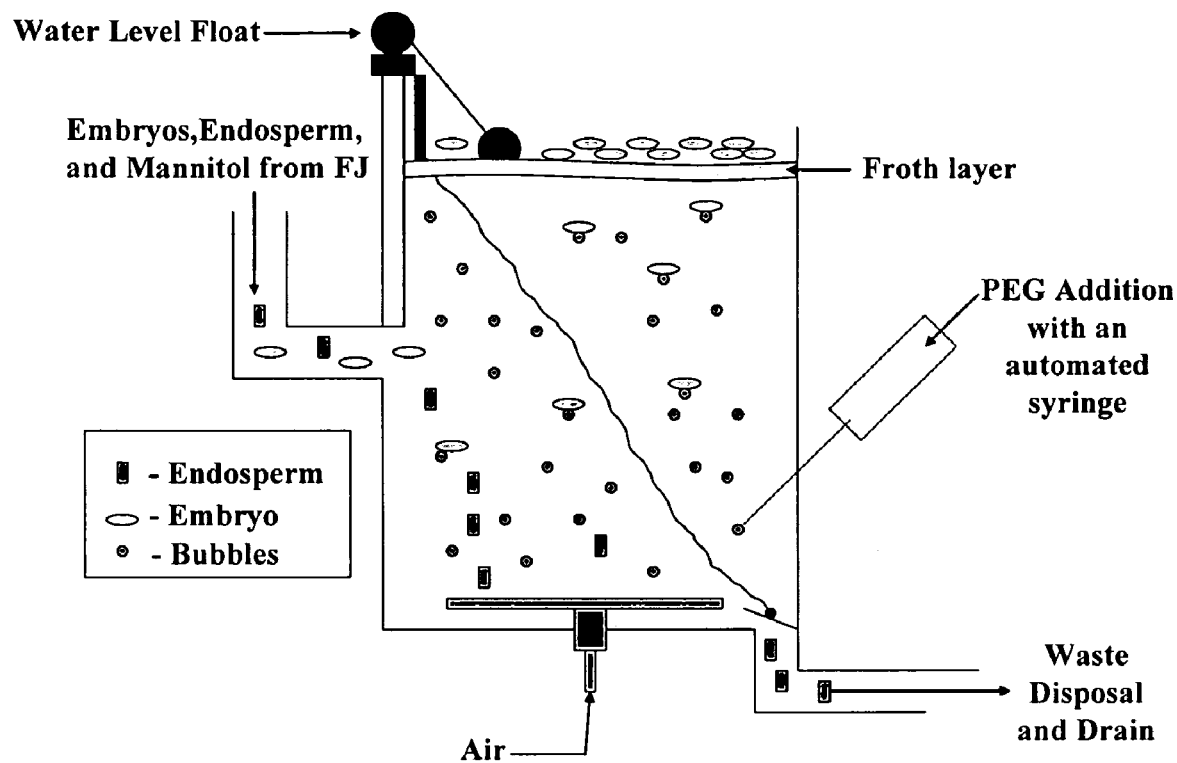
FIG. 23 depicts an alternative apparatus for separating embryos by flotation as described in Example 20.

In this apparatus (FIG. 23), the embryos and endosperms flow into a chamber provided with a means for producing bubbles. The bubbles can be generated by forced air through a sparger. Preferably the bubble size (diameter) is about 100 µm to 500 µm. A bubble stabilizing agent such as polyethylene glycol (PEG) is also added at a concentration of about 1 to about 100 ppm, for instance 20 ppm. The embryos preferentially attach to the bubbles through hydrophobic interaction and the bubbles raise the attached embryos to the surface of the chamber. Addition of PEG enables the bubbles to carry their "load" of embryos to the surface. The PEG also helps to create a froth layer at the top of the surface and embryos collect on top of the froth layer where they are carried into the overflow outlet. A motorized skimmer device can be used to further facilitate flow of the froth containing embryos into the outlet where they pass through an imaging station or a counting device for counting the number of embryos and collected in containers as needed. A switch arm operably linked to the imaging station or the counting device can be provided to dispense desired numbers of embryos into different containers. The containers can be connected to a vacuum manifold device to remove the liquid leaving behind the embryos for further use.

The apparatus is further provided with a means for bringing liquid in and out of the chamber. The liquid level in the chamber can be managed by a liquid leveling device. Endosperms and other debris that are not selectively attached to the bubbles are discarded through the means for taking liquid out at the bottom of the container, such as a waste outflow drain. The same liquid medium that is used for excising the embryos can be used to fill the chamber for separating the embryos. The medium coming out of this apparatus can be recycled for further use during excision and separation processes.

Example 21

Combination Device for Excising and Separating Corn Embryos for Tissue Culture

Figure 24:
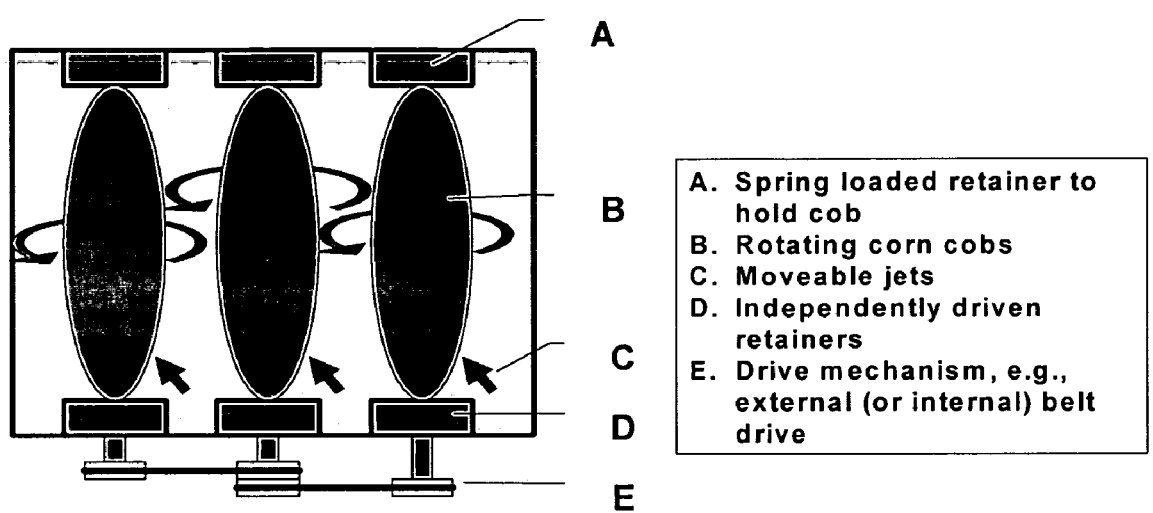
FIG. 24 illustrates a top view of an embryo extractor in a combination device for extracting and separating corn embryo tissue for tissue culture.
Figure 25:
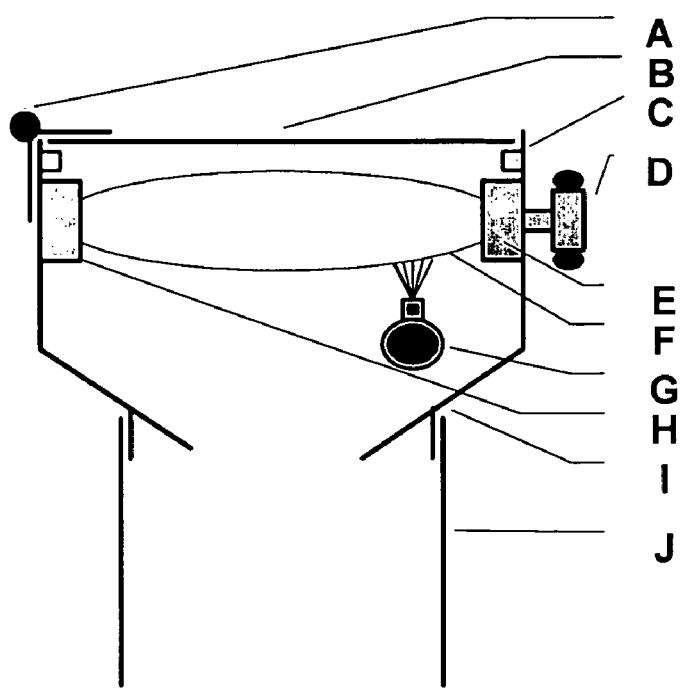
FIG. 25 depicts an end view of an extractor for rotating and extracting embryos from multiple ears.
Figure 26:
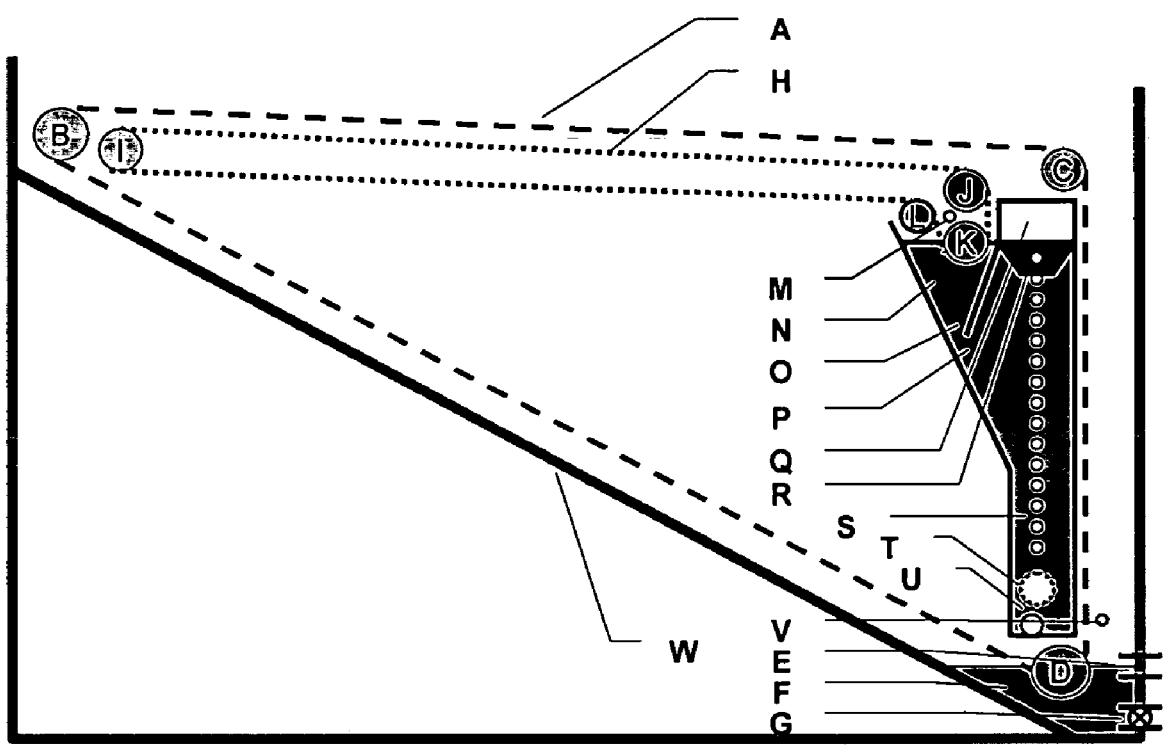
FIG. 26 illustrates a side view of an embryo separator.

This example illustrates a combination device or an integrated device comprising an embryo extractor as shown in FIGS. 24-25 and an embryo separator as shown in FIG. 26. Preferably, the embryo extractor is in communication with the separator. However, the embryo extractor or the separator can be operated separately and the output of the embryo extractor can be the input of the embryo separator.

Referring to FIG. 24 which is a top view, the embryo extractor is provided with at least one fluid jet (C) for extracting embryos from each cob (B). More than one fluid jet may be directed at a single cob. Each cob in FIG. 24 is held in place by spring-loaded retainers (A) at one end of the cobs and a powered retainer (D) at the other end which may be driven by a belt mechanism (E). A side view of the apparatus is shown in FIG. 25. Normally, the crowns of the kernels on the cob are partially or fully removed to facilitate embryo extraction.

Any liquid medium can be used to produce the jet flow (C), for instance as described in Example 15. Sterile water can be used to excise embryos since the time between initial embryo contact with water and immersion in the culture medium in the flotation tank is short. A filter can be used to sterilize the water. Alternatively, the liquid medium comprises mannitol or other solute of suitable osmotic strength as described above.

As shown in FIG. 26, after extraction of the embryos from kernels, the embryos and debris optionally fall onto, or are added onto, an embryo separator comprising a double screen conveyer belt system connected to a flotation chamber. The double screen conveyer belt has a moving coarse screen (A) which catches coarse material, but allows embryos and other fine material to pass through to a fine screen (H) which retains the embryos and similar size material, but allows very fine material and liquid to pass through to the waste liquid chute (W). The material collected on the coarse screen is washed loose in the coarse screen wash tank (F) and is aided by the flow of waste down the waste liquid chute (W) and out a drain through the coarse screen wash tank overflow (E) and wash tank drain (G). The material collected on the fine screen (H) is washed loose in the fine screen wash tank (N) with the help of fresh medium and preferably a frother through inlet (M). If embryos do not dislodge from the fine screen (H) into the fine screen wash tank (N), agitation can be used. For example, embryos captured on the fine screen are dislodged into the floatation medium as they pass around roller (K) and also by impact of make-up medium added via (M). The delivery of fresh media and the frother is adjusted so that debris accumulating in the floatation chamber are continually removed through the liquid level regulator inlet (U) and outlet tubes (V).

Molded thermoplastic meshes, which are not woven, may be preferable to use in this apparatus since they do not unravel. Such meshes are available (e.g. McMaster-Carr, Atlanta, Ga.) in various screen (strand) thicknesses, strand widths and mesh opening sizes. Meshes made of polypropylene are also preferable because they can be autoclaved. The precise mesh dimensions may be empirically selected by the operator depending on the expected sizes of embryos and debris that are introduced to the separator.

Referring to FIG. 26, the coarse screen (A) and the fine screen (H) can be supported by rollers. Preferably, the coarse screen (A) is supported by a powered roller (B), an idler roller (C), and a wash roller (D). The fine screen (H) is supported by a powered roller (I), idler roller (J), a wash roller (K), and a lifter roller (L). The rollers may be straight cylindrical, or other than straight cylindrical, preferably concave-cylindrical since these allow troughed belts to be used which typically have less loss of product along their edges than flat belts. Troughed belts may allow higher belt speeds and inclines. One or more of the rollers may be powered, for example roller (B), and may have their surfaces textured to more firmly grasp the screen. It may be desirable to power only one roller directly and have the other powered, for example roller (C), from the first as with a belt or gear. Lateral and central supports or guides under the coarse and fine screens may be desirable to prevent sagging and loss of liquid along the edges of the screens. Additional support rollers may also be desirable.

After the material collected on the fine screen (H) dislodges in the fine screen wash tank (N) it falls past the bubble deflector (O) and enters the flotation chamber (P) where it encounters rising bubbles of air (S) produced by, for example, by an air dispersion tube (T). At this point bubbles of air attach preferentially to the hydrophobic surfaces of the embryos, carrying them to the surface where they are deposited in a froth through a flotation chamber side opening (Q) and embryo delivery (froth) chute (R). If the embryos descending in the flotation chamber (P) are not exposed adequately to the bubbles, a mixing device such as a magnetic stirrer can be provided in the lower portion of the chamber (P) to improve exposure.

Figure 27:
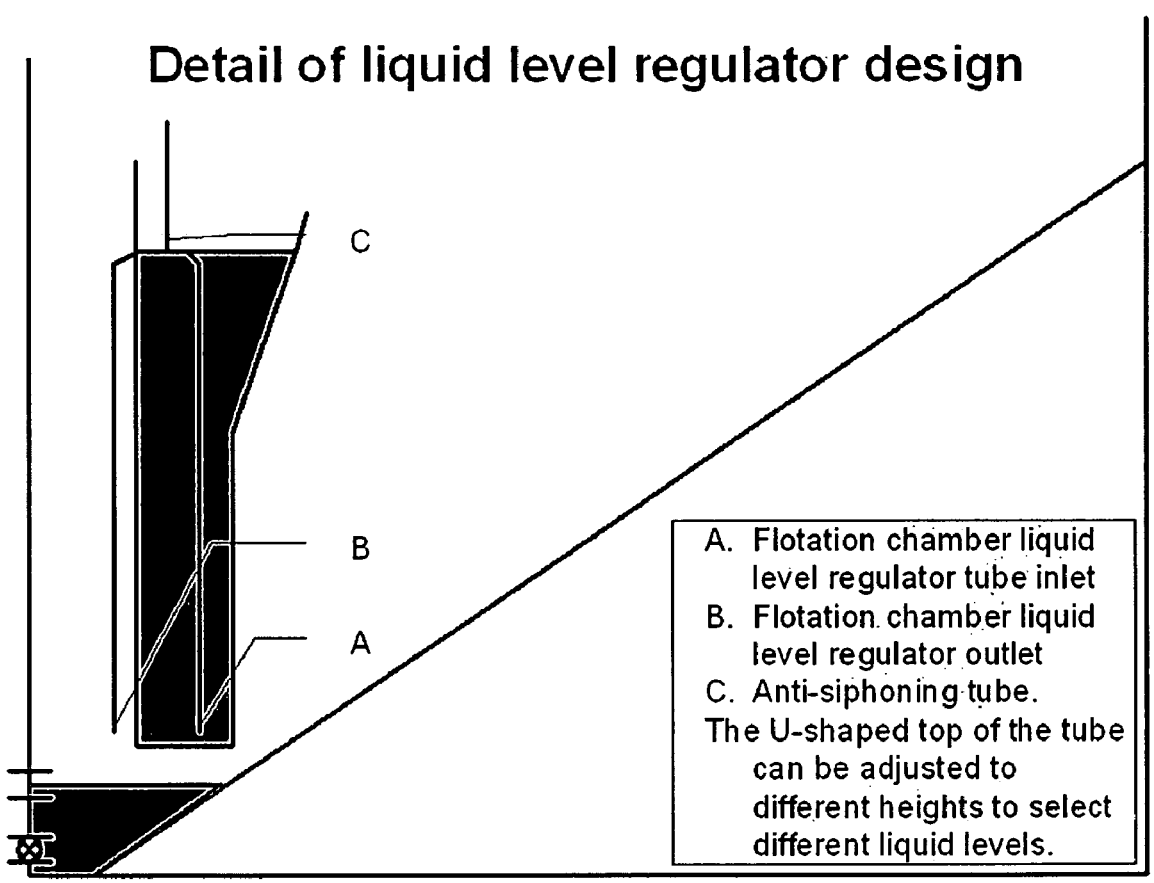
FIG. 27 illustrates an exemplary liquid level regulator.

The liquid level in the flotation tank is regulated by the entering fresh medium and the frother from the inlet (M) and by the liquid leveling system (e.g. FIG. 27) comprising an inlet tube U and outlet tube (V) in which excess liquid along with debris enters the tube U and exits the tube (V). A U-shaped tube connects (U) and (V) with the highest level in the tube reaching the level at which the liquid is to be maintained. The top of the U-tube is also provided with an anti-siphoning opening. Other liquid leveling device such as those float-based, optics-based, conductivity-based, and electric-based can be envisioned to regulate the level of liquid in this device.

Example 22

Apparatus for Isolating Transformable Tissues from Seeds and Fruits

The compositions, methods, and apparatuses of the present invention can be used to isolate transformable tissue, for example, embryos from seeds and fruits of other monocot and dicot plants, including, without limitation, corn, wheat, barley, soybean, sunflower, cotton, canola, peppers, tomatoes, raspberry, and strawberry, among others.

Figure 28:
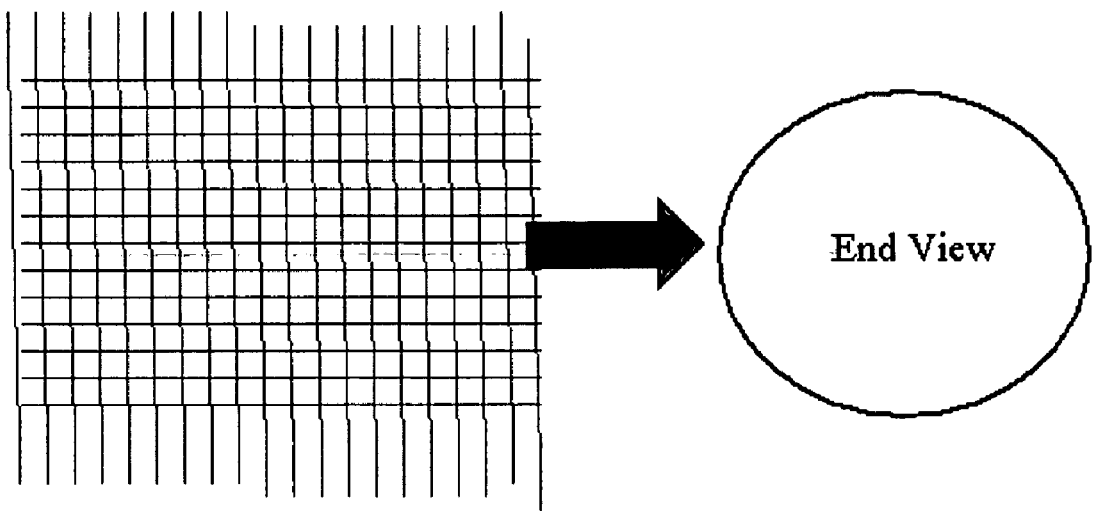
FIG. 28 illustrates exemplary mesh and slot holders for seed and/or fruit tissue.
Figure 28:
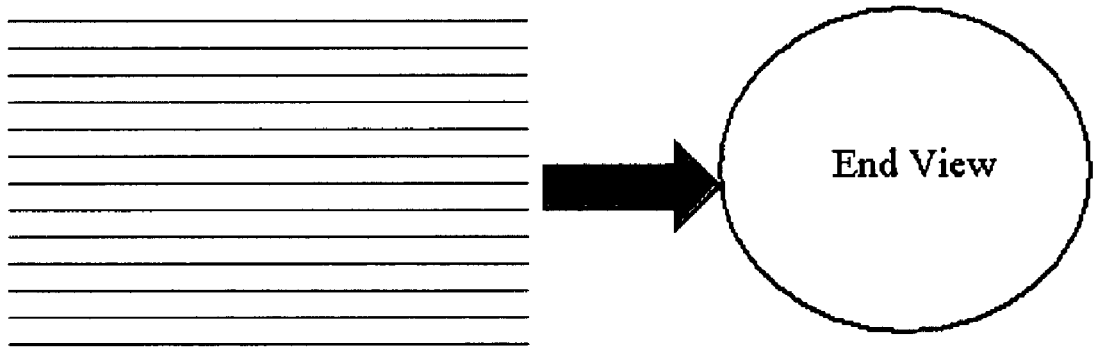
Figure 29:
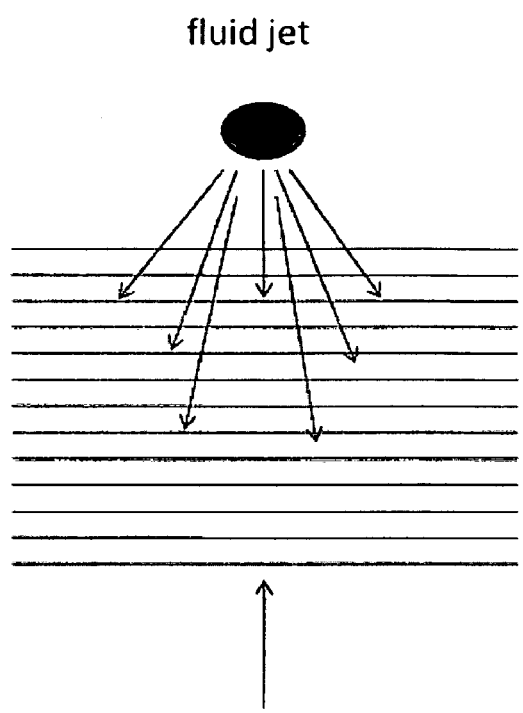
FIG. 29 depicts a sheet and a cylindrical embodiment of a seed or fruit holder.
Figure 29:
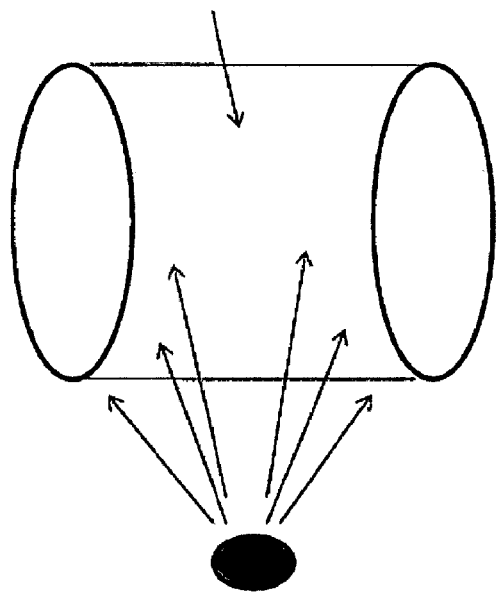

A suitable holder, for example, a sheet having holes and/or slots suitable for holding seeds or fruits of various shapes and sizes is provided (e.g. FIG. 28). The holder can be made from a suitable material such as plastic or metal. The holder can be a flat sheet or rolled into a cylinder as shown in FIG. 29, and suspended in a gaseous phase such as an air or liquid phase or may be partially suspended in the gaseous and the liquid phases. The seeds and fruits can be held onto the holder by a suitable force, such as a mechanical and/or suction force. The holder can be fixed relative to a fluid force, for example a liquid stream of the medium described in Example 15 or movable relative to the fluid force.

Figure 30:
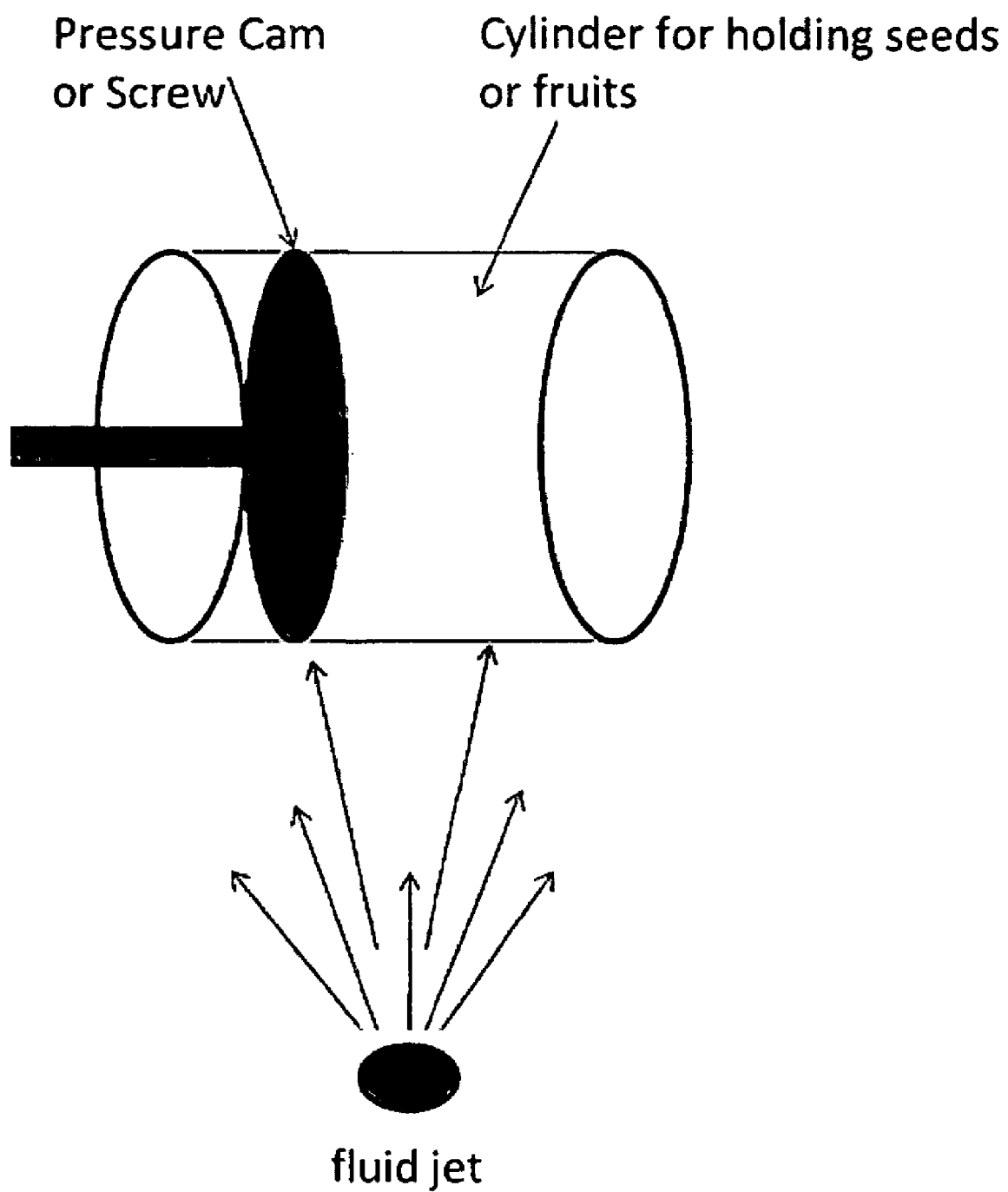
FIG. 30 illustrates an embodiment of a seed or fruit holder comprising a pressure cam or screw.

In another embodiment shown in FIG. 30, a pressure Cam or Screw, for example an auger, is inserted at one end of the cylinder to apply pressure on the seeds and fruits to further facilitate the isolation of embryos. The isolated embryos can be separated from debris by several methods described elsewhere in the specification.

In another embodiment of the present invention, the sheet or cylinder may be centrifuged in a container to apply forces on the retained seeds or fruits to isolate embryos.

The embryos can be separated from other tissues as described in Examples 18-20 and used for transforming and regenerating various plant species. For instance, soybean embryos can be transformed using methods described in U.S. Pat. No. 7,002,058. Transformation methods for other plants are known in the art.

Example 23

Methods for Separating Cotton and Soybean Embryos

Figure 31:
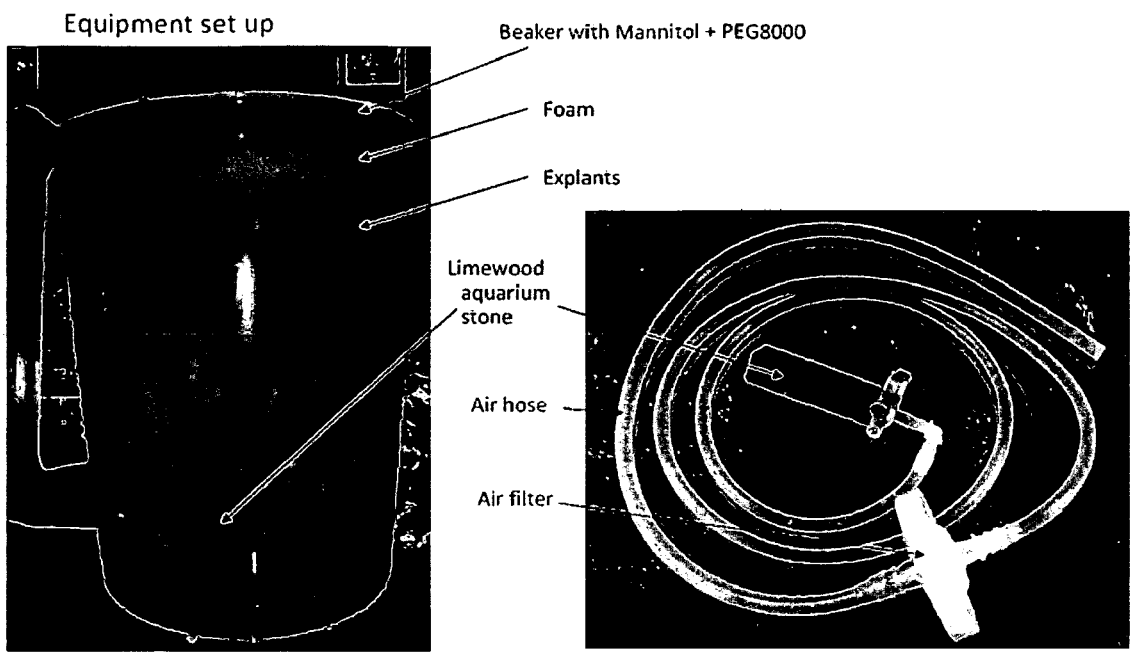
FIG. 31 illustrates an explant separator comprising a limewood bubble dispersion device utilized for separation of cotton embryogenic tissue.
Figure 32:
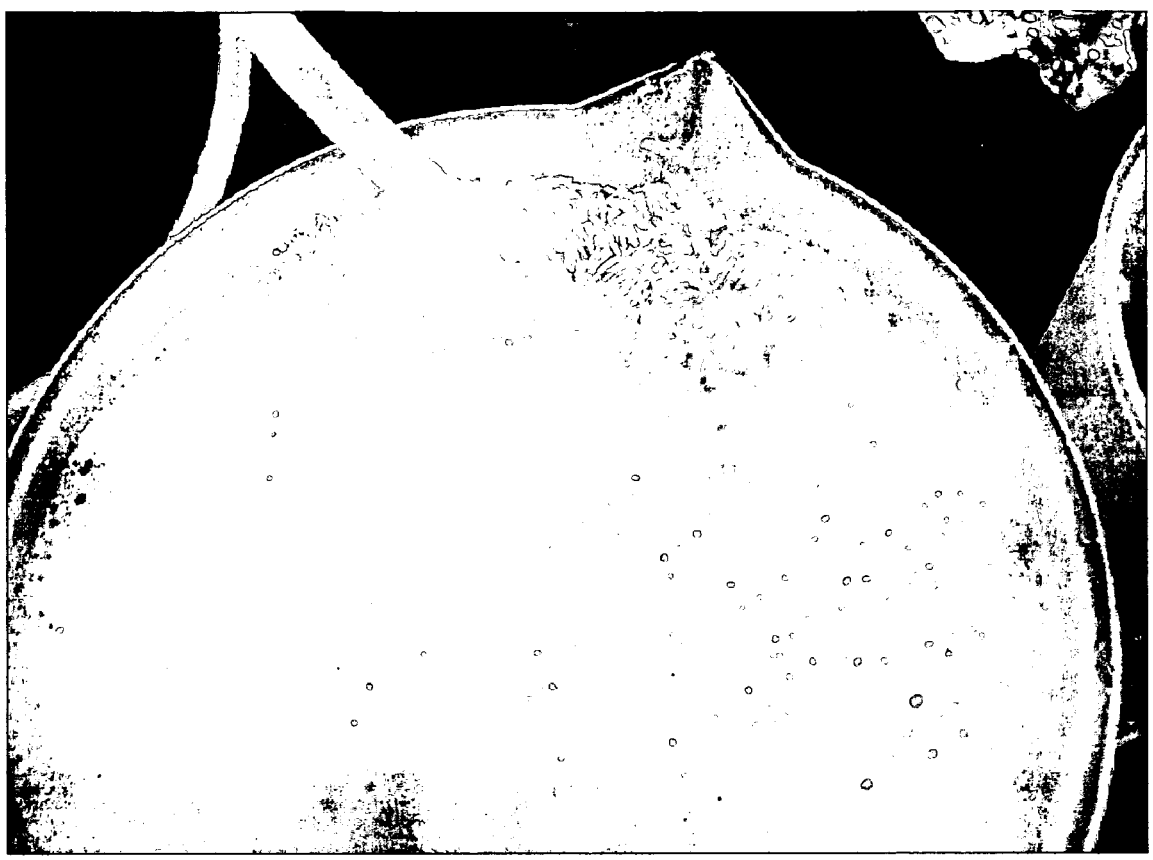
FIG. 32 depicts cotton explants floating atop the froth produced in the microbubble dispersion device shown in FIG. 31.
Figure 33:
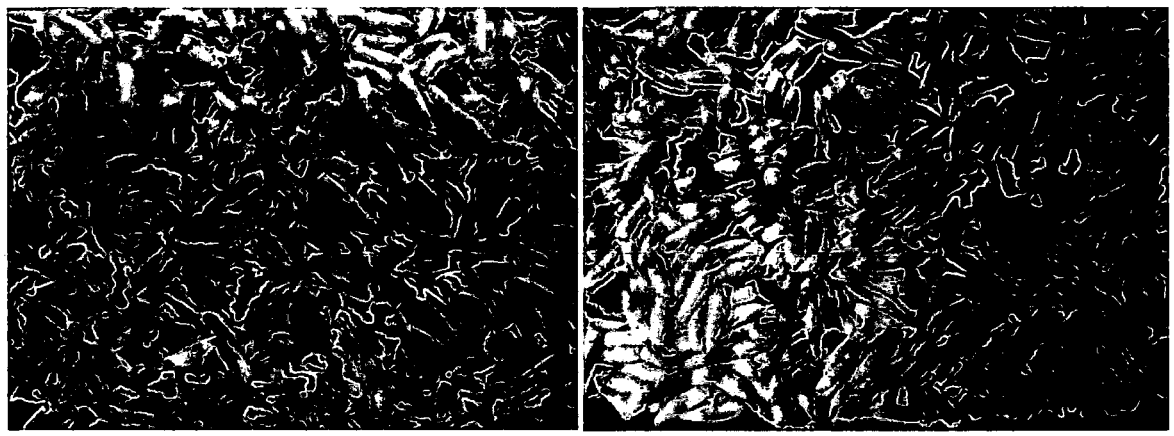
FIG. 33 shows a comparison of the purity of cotton explants produced either via excision and sieving (left) or excision, sieving, and then additionally purified using microbubble technology (right).

This example illustrates the utility of compositions, methods, and apparatuses of the present invention in separating cotton and soybean embryos from seed tissue, thus demonstrating wider utility. Cotton and soybean seeds were crushed by the method and apparatus described in U.S. patent application Ser. No. 12/045,502, filed Mar. 10, 2008, and U.S. Patent Application Publication 20050005321 and added to a solution of 0.2M Mannitol with 0.0012% PEG 8000 for isolation of cotton embryos and about 0.003% PEG 8000 for isolation of soybean embryos, using the apparatus shown in FIG. 31. Bubbles were produced for instance as described in Example 18. Most of the cotton embryonic axes were found to accumulate with the bubbles as shown in FIGS. 32-33. The cotton embryos were prepared for transformation using the methods described in U.S. patent application Ser. No. 12/045, 502. In the case of soybean, the broken embryos (embryonic axis and cotyledons) were found to be at the bottom of the container while most of the seed coats floated to the top with the bubbles. The embryonic axes and cotyledons were then further separated by density differential methods. For example, in a 6.5% Ficoll solution in 20% sucrose embryonic axes rose to the surface while cotyledons sank to the bottom of the container. The soybean embryos can be transformed using the method described in U.S. Pat. No. 7,002,058.

Example 24

Development of a Co-Culture Medium for Enhancing Transformation Frequency

In some experiments, use of co-culture medium 1233 (U.S. Patent Applic. Publn. 2004/00244075) in the corn transformation process, utilizing embryos prepared by a fluid jet method and separated by a flotation method, resulted in lower transformation frequencies (TFs). In order to maintain or enhance transformation frequency, a new co-culture medium, termed "1898," was tested and unexpectedly found to enhance TFs.

Several set of experiments were conducted to compare co-culture medium 1233 and co-culture medium 1898. Among other compositional differences (see Table 9), co-culture medium 1898 has a lower level of 2,4-D and has Carbenicillin. Immature embryos from corn ears were excised and separated as described in Examples above. Separated embryos were split into two treatments. Embryos in both treatments were inoculated with plant transformation vector pMON97367 comprising a gus and a CP4 expression cassette. The embryos for treatment 1 were co-cultured on medium 1233 and the embryos for treatment 2 were co-cultured on the medium 1898. After overnight co-culture, embryos were processed by the method described in the US Patent Application Publication 2004/00244075.

Table 8 shows that the use of co-culture medium 1898 resulted in improvements in all key performance indicators such as culture response, events created, events transferred to phytatrays, events transferred to soil, and % TF in comparison to the use of the co-culture medium 1233. Table 9 gives compositions of media used.

TABLE 8

Enhancement of transformation frequency by co-culture medium 1898.

| Co-culture Medium | Total # Embryos Tested | % Embryos with Embryogenic Response | # Events Created | % Transferred to Phytatrays | % Transferred to Soil | % TF |
| --- | --- | --- | --- | --- | --- | --- |
| 1233 | 660 | 53.0 | 107 | 16.2 | 11.7 | 10.6% |
| 1898 | 628 | 79.3 | 263 | 43.5 | 31.5 | 30.9% |

TABLE 9

Media compositions used in the present invention. Media 1233, 1278, 1073, 1071, 1084 are from Cai et al.; U.S. patent application Publn. 2004/00244075. Medium 1898 is from U.S. patent application Publn. 2008/0124727.

| Media Components/ L (Suppliers) | 1233 (co-culture) | 1898 (co-culture) | 1278 (MSW 50 + BAP) (selection) | 1073 (MS/6BA) (1st regeneration) | 1071 (MSOD) (2nd regeneration) | 1084 (rooting) |
|---|---|---|---|---|---|---|
| MS Basal Salts (Phytotech) | 2.165 g | 4.33 g | 4.33 g | 4.33 g | 4.33 g | 2.165 g |
| MS Vitamins (100X) (Phytotech) | 10 mL | 10 mL | 10 mL | 0 | 0 | 0 |
| MS Fromm Vitamins (1000X)* | 0 | 0 | 0 | 1 mL | 1 mL | 0 |
| BAP (Sigma) | 0 | 0 | 0.01 mg | 3.5 mg | 0 | 0 |
| Thiamine HCL (Sigma) | 0.5 mg | 0.5 mg | 0.5 mg | 0 | 0 | 0 |
| 2,4-D (Phytotech) | 3 mg | 0.5 mg | 0.5 mg | 0 | 0 | 0 |
| NAA (Sigma) | 0 | 0 | 0 | 0 | 0 | 0.5 mg |
| IBA (Sigma) | 0 | 0 | 0 | 0 | 0 | 0.75 mg |
| Sucrose (Phytotech) | 20 g | 30 g | 30 g | 30 g | 0 | 20 g |
| Glucose (Phytotech) | 10 g | 0 | 0 | 0 | 10 g | 0 |
| Maltose (Phytotech) | 0 | 0 | 0 | 0 | 20 g | 0 |
| Proline (Sigma) | 115 mg | 1.38 g | 1.38 g | 1.38 g | 0 | 0 |
| Casamino Acids (Difco) | 0 | 0.5 g | 0.5 g | 0.05 g | 0.5 | 0 |
| Asparagine monohydrate (Sigma) | 0 | 0 | 0 | 0 | 0.15 | 0 |
| Myo-inositol (Sigma) | 0 | 0 | 0 | 0 | 0.1 g | 0 |
| Low EEO Agarose (Sigma) | 5.5 g | 5.5 g | 0 | 0 | 0 | 0 |
| Phytagel (Sigma) | 0 | 0 | 3 g | 3 g | 3 g | 3 g |
| Acetosyringone (Aldrich) | 200 uM | 200 uM | 0 | 0 | 0 | 0 |
| Carbenicillin (Phytotech) | 0 | 50 mg | 500 mg | 250 mg | 250 mg | 0 |
| Glyphosate (Gateway Chemical) | 0 | 0 | 0.1 mM | 0.1 mM | 0.1 mM | 0.1 mM |
| Silver Nitrate (Sigma) | 3.4 mg | 3.4 mg | 3.4 mg | 0 | 0 | 0 |
| pH | 5.2 | 5.8 | 5.8 | 5.8 | 5.8 | 5.8 |

*Comprising 1250 mg/L nicotinic acid (Sigma), 250 mg/L pyridoxine HCl (Sigma), 250 mg/L thiamine HCl (Sigma), and 250 mg/L calcium pantothenate (Sigma).

All of the materials and methods disclosed and claimed herein can be made and used, as instructed by the above disclosure, and without undue experimentation, by a person of ordinary skill in the art. Although the materials and methods of this invention have been described in terms of preferred embodiments and illustrative examples, it will be apparent to those of skill in the art that variations may be applied to the materials and methods described herein without departing from the concept, spirit, and scope of the invention. All such similar substitutes and modifications apparent to those skilled in the art are deemed to be within the concept, spirit, and scope of the invention as further defined by the appended claims.

REFERENCES

The following references, to the extent that they provide exemplary procedural or other details supplementary to those set forth herein, are specifically incorporated herein by reference.

U.S. Pat. No. 5,550,318
U.S. Pat. No. 5,780,708
U.S. Pat. No. 6,194,636
U.S. Pat. No. 6,232,526
U.S. Pat. No. 7,002,058
U.S. Pat. No. 7,150,993
U.S. patent application Ser. No. 10/710,067
U.S. patent application Ser. No. 11/613,031
U.S. patent application Ser. No. 12/045,502
U.S. Patent Publn. 2003/0024014
U.S. Patent Publn. 2004/0016030
U.S. Patent Publn. 2004/0126845
U.S. Patent Publn. 2004/0210958
U.S. Patent Publn. 2004/0216189
U.S. Patent Publn. 2004/0244075
U.S. Patent Publn. 2005/0246786
U.S. Patent Publn. 2008/0124727

U.S. Prov. Patent Appln. 60/894,096
U.S. Prov. Patent Appln. 60/915,066

What is claimed is:

1. A method for obtaining embryos suitable for tissue culture and/or genetic transformation, comprising at least partially excising an embryo from a plant seed in a liquid medium consisting essentially of water and/or an osmotic agent with an osmolality of about 0 mOsm/kg to about 600 mOsm/kg, wherein the embryo remains viable for tissue culture and/or genetic transformation following excising the embryo from the plant seed; further comprising the step of genetically transforming the embryo, wherein the step of transforming comprises use of a co-culture medium comprising a bactericide, and wherein the co-culture medium comprises about 0.5-1.5 mg/L of 2,4-D.

2. The method of claim 1, wherein the osmotic agent is selected from the group consisting of mannitol, sorbitol, glucose, and sucrose.

3. The method of claim 2, wherein the medium consists essentially of water and mannitol in a concentration of from about 0.05 M to about 0.5 M.

4. The method of claim 2, wherein the medium consists essentially of water and sucrose in a concentration of from about 0.05 M to about 0.5 M.

5. The method of claim 1, wherein the bactericide is carbenicillin.

6. The method of claim 1, further comprising regenerating a transgenic plant from the transformed embryo.

7. The method of claim 1, further comprising at least partially excising a plurality of embryos from a population of plant seeds or ears in the liquid medium.

8. The method of claim 1, wherein the embryo is a maize embryo, a millet embryo, a soybean embryo, or a cotton embryo.

* * * * *